(12) United States Patent
Wilson et al.

(10) Patent No.: US 10,864,080 B2
(45) Date of Patent: Dec. 15, 2020

(54) DISTAL ANCHOR APPARATUS AND METHODS FOR MITRAL VALVE REPAIR

(71) Applicant: Harpoon Medical, Inc., Baltimore, MD (US)

(72) Inventors: Peter Wilson, Killingworth, CT (US); Stephen Epstein, Baltimore, MD (US); Stephen Cournane, Severn, MD (US)

(73) Assignee: Harpoon Medical, Inc., Baltimore, MD (US)

( * ) Notice: Subject to any disclaimer, the term of this patent is extended or adjusted under 35 U.S.C. 154(b) by 283 days.

(21) Appl. No.: 15/937,582

(22) Filed: Mar. 27, 2018

(65) Prior Publication Data

US 2018/0214269 A1   Aug. 2, 2018

Related U.S. Application Data

(63) Continuation of application No. PCT/US2016/055170, filed on Oct. 3, 2016.
(Continued)

(51) Int. Cl.
*A61F 2/24*     (2006.01)
*A61B 17/04*   (2006.01)
(Continued)

(52) U.S. Cl.
CPC ........ *A61F 2/2457* (2013.01); *A61B 17/0401* (2013.01); *A61B 17/0469* (2013.01);
(Continued)

(58) Field of Classification Search
CPC ............ A61B 17/0401; A61B 17/0469; A61B 2017/00234; A61B 2017/00243;
(Continued)

(56) References Cited

U.S. PATENT DOCUMENTS 3,752,516 A   8/1973   Mumma
4,403,797 A   9/1983   Ragland, Jr.
(Continued)

FOREIGN PATENT DOCUMENTS

CN   104873307 A   9/2015
EP   0791330 A3   11/1997
(Continued)

OTHER PUBLICATIONS

Barbero-Marcial, M. et al., "Transxiphoid Approach Without Median Sternotomy for the Repair of Atrial Septal Defects," (1998) Ann. Thorne. Surg., 65(3):771-774.
(Continued)

*Primary Examiner* — Kathleen S Holwerda
*Assistant Examiner* — Kankindi Rwego
(74) *Attorney, Agent, or Firm* — Chang & Hale

(57) ABSTRACT

In some embodiments, an apparatus includes a handle, an actuator, a pusher device, and a puncture member. A distal anchor is disposed at a distal end portion of an artificial chorda, or suture, and is in a delivery configuration. The artificial chorda, or suture, is coupled to the actuator and extends through a lumen of the puncture member. The actuator can be actuated to move the puncture member distally a preset distance, and to move the pusher device distally such that at least a portion of the distal anchor is moved distal to the distal end of the puncture member and the distal anchor is moved from its delivery configuration to a deployed configuration.

21 Claims, 69 Drawing Sheets

Related U.S. Application Data

(60) Provisional application No. 62/315,879, filed on Mar. 31, 2016, provisional application No. 62/236,225, filed on Oct. 2, 2015.

(51) Int. Cl.
    *A61B 17/00*     (2006.01)
    *A61F 2/95*     (2013.01)
    *A61B 17/06*     (2006.01)

(52) U.S. Cl.
    CPC .. *A61F 2/2466* (2013.01); *A61B 2017/00243* (2013.01); *A61B 2017/00247* (2013.01); *A61B 2017/00783* (2013.01); *A61B 2017/00986* (2013.01); *A61B 2017/0409* (2013.01); *A61B 2017/0417* (2013.01); *A61B 2017/0419* (2013.01); *A61B 2017/06052* (2013.01); *A61B 2217/005* (2013.01); *A61B 2217/007* (2013.01); *A61F 2/9517* (2020.05); *A61F 2230/0039* (2013.01); *A61F 2230/0052* (2013.01)

(58) Field of Classification Search
    CPC ........... A61B 2017/00247; A61B 2017/00783; A61B 2017/00986; A61B 2017/0409; A61B 2017/0417; A61B 2017/0419; A61B 2017/06052; A61B 2217/005; A61B 2217/007; A61F 2/2457; A61F 2/2466; A61F 2002/9517; A61F 2230/0039; A61F 2230/0052
    See application file for complete search history.

(56) References Cited

U.S. PATENT DOCUMENTS

| | | | |
|---|---|---|---|
| 4,662,376 | A | 5/1987 | Belanger |
| 4,807,625 | A | 2/1989 | Singleton |
| 5,144,961 | A | 9/1992 | Chen et al. |
| 5,147,316 | A | 9/1992 | Castillenti |
| 5,312,423 | A | 5/1994 | Rosenbluth et al. |
| 5,391,176 | A | 2/1995 | de la Torre |
| 5,405,352 | A | 4/1995 | Weston |
| 5,454,821 | A | 10/1995 | Harm et al. |
| 5,472,446 | A | 12/1995 | de la Torre |
| 5,507,754 | A | 4/1996 | Green et al. |
| 5,527,323 | A | 6/1996 | Jervis et al. |
| 5,554,184 | A | 9/1996 | Machiraju |
| 5,626,614 | A | 5/1997 | Hart |
| 5,643,293 | A | 7/1997 | Kogasaka et al. |
| 5,681,331 | A | 10/1997 | de la Torre et al. |
| 5,716,368 | A | 2/1998 | de la Torre et al. |
| 5,727,569 | A | 3/1998 | Benetti et al. |
| 5,728,109 | A | 3/1998 | Schulze et al. |
| 5,746,752 | A | 5/1998 | Burkhart |
| 5,769,862 | A | 6/1998 | Kammerer et al. |
| 5,797,928 | A | 8/1998 | Kogasaka |
| 5,824,065 | A | 10/1998 | Gross |
| 5,931,868 | A | 8/1999 | Gross |
| 5,957,936 | A | 9/1999 | Yoon et al. |
| 5,971,447 | A | 10/1999 | Steck, III |
| 6,010,531 | A | 1/2000 | Donlon et al. |
| 6,074,417 | A | 6/2000 | Peredo |
| 6,269,819 | B1 | 8/2001 | Oz et al. |
| 6,332,893 | B1 | 12/2001 | Mortier et al. |
| 6,562,051 | B1 | 5/2003 | Bolduc et al. |
| 6,626,930 | B1 | 9/2003 | Allen et al. |
| 6,629,534 | B1 | 10/2003 | St Goar et al. |
| 6,752,810 | B1 | 6/2004 | Gao et al. |
| 6,840,246 | B2 | 1/2005 | Downing |
| 6,921,408 | B2 | 7/2005 | Sauer |
| 6,940,246 | B2 | 9/2005 | Mochizuki et al. |
| 6,978,176 | B2 | 12/2005 | Lattouf |
| 6,991,635 | B2 | 1/2006 | Takamoto et al. |
| 6,997,950 | B2 | 2/2006 | Chawla |
| 7,112,207 | B2 | 9/2006 | Allen et al. |
| 7,291,168 | B2 | 11/2007 | Macoviak et al. |
| 7,294,148 | B2 | 11/2007 | McCarthy |
| 7,309,066 | B2 | 12/2007 | Carrier |
| 7,316,706 | B2 | 1/2008 | Bloom et al. |
| 7,373,207 | B2 | 5/2008 | Lattouf |
| 7,431,692 | B2 | 10/2008 | Zollinger et al. |
| 7,513,908 | B2 | 4/2009 | Lattouf |
| 7,534,260 | B2 | 5/2009 | Lattouf |
| 7,608,091 | B2 | 10/2009 | Goldfarb et al. |
| 7,618,449 | B2 | 11/2009 | Tremulis et al. |
| 7,632,308 | B2 | 12/2009 | Loulmet |
| 7,635,386 | B1 | 12/2009 | Gammie |
| 7,666,196 | B1 | 2/2010 | Miles |
| 7,744,609 | B2 | 6/2010 | Allen et al. |
| 7,837,727 | B2 | 11/2010 | Goetz et al. |
| 7,871,368 | B2 | 1/2011 | Zollinger et al. |
| 7,871,433 | B2 | 1/2011 | Lattouf |
| 7,959,650 | B2 | 6/2011 | Kaiser et al. |
| 8,029,518 | B2 | 10/2011 | Goldfarb et al. |
| 8,029,565 | B2 | 10/2011 | Lattouf |
| 8,043,368 | B2 | 10/2011 | Crabtree |
| 8,147,542 | B2 | 4/2012 | Maisano et al. |
| 8,226,711 | B2 | 7/2012 | Mortier et al. |
| 8,241,304 | B2 | 8/2012 | Bachman |
| 8,252,050 | B2 | 8/2012 | Maisano et al. |
| 8,292,884 | B2 | 10/2012 | Levine et al. |
| 8,303,622 | B2 | 11/2012 | Alkhatib |
| 8,333,788 | B2 | 12/2012 | Maiorino |
| 8,382,829 | B1 | 2/2013 | Call et al. |
| 8,439,969 | B2 | 5/2013 | Gillinov et al. |
| 8,454,656 | B2 | 6/2013 | Tuval |
| 8,465,500 | B2 | 6/2013 | Speziali |
| 8,475,525 | B2 | 7/2013 | Maisano et al. |
| 8,500,800 | B2 | 8/2013 | Maisano et al. |
| 8,608,758 | B2 | 12/2013 | Singhatat et al. |
| 8,663,278 | B2 | 3/2014 | Mabuchi et al. |
| 8,771,296 | B2 | 7/2014 | Nobles et al. |
| 8,828,053 | B2 | 9/2014 | Sengun et al. |
| 8,852,213 | B2 | 10/2014 | Gammie et al. |
| 8,688,791 | B2 | 11/2014 | Jaramillo et al. |
| 8,940,008 | B2 | 1/2015 | Kunis |
| 9,131,884 | B2 | 9/2015 | Holmes et al. |
| 9,192,287 | B2 | 11/2015 | Saadat et al. |
| 2002/0013571 | A1 | 1/2002 | Goldfarb et al. |
| 2003/0023254 | A1 | 1/2003 | Chiu |
| 2003/0094180 | A1 | 5/2003 | Benetti |
| 2003/0105519 | A1 | 6/2003 | Fasol et al. |
| 2003/0120264 | A1 | 6/2003 | Lattouf |
| 2003/0120341 | A1 | 6/2003 | Shennib et al. |
| 2004/0044365 | A1 | 3/2004 | Bachman |
| 2004/0093023 | A1 | 5/2004 | Allen et al. |
| 2004/0199183 | A1 | 10/2004 | Oz et al. |
| 2005/0004667 | A1 | 1/2005 | Swinford et al. |
| 2005/0075654 | A1 | 4/2005 | Kelleher |
| 2005/0121042 | A1* | 6/2005 | Belhe ................. A61B 17/0057 128/887 |
| 2005/0149067 | A1 | 7/2005 | Takemoto et al. |
| 2005/0149093 | A1 | 7/2005 | Pokorney |
| 2005/0154402 | A1 | 7/2005 | Sauer et al. |
| 2005/0216036 | A1 | 9/2005 | Nakao |
| 2005/0216077 | A1 | 9/2005 | Mathis et al. |
| 2005/0261710 | A1 | 11/2005 | Sakamoto et al. |
| 2005/0267493 | A1 | 12/2005 | Schreck et al. |
| 2006/0030866 | A1 | 2/2006 | Schreck |
| 2006/0100698 | A1 | 5/2006 | Lattouf |
| 2006/0111739 | A1 | 5/2006 | Staufer et al. |
| 2006/0167541 | A1 | 7/2006 | Lattouf |
| 2006/0190030 | A1 | 8/2006 | To et al. |
| 2006/0282088 | A1 | 12/2006 | Ryan |
| 2007/0001857 | A1 | 1/2007 | Hartmann et al. |
| 2007/0049952 | A1 | 3/2007 | Weiss |
| 2007/0055292 | A1 | 3/2007 | Ortiz et al. |
| 2007/0112422 | A1 | 5/2007 | Dehdashtian |
| 2007/0112425 | A1 | 5/2007 | Schaller et al. |
| 2007/0118151 | A1 | 5/2007 | Davidson |
| 2007/0118154 | A1 | 5/2007 | Crabtree |
| 2007/0149995 | A1 | 6/2007 | Quinn et al. |

(56) References Cited

U.S. PATENT DOCUMENTS

| | | |
|---|---|---|
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St Goar et al. |
| 2008/0188893 A1 | 8/2008 | Selvitelli et al. |
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2009/0005863 A1 | 1/2009 | Goetz et al. |
| 2009/0043153 A1 | 2/2009 | Zollinger et al. |
| 2009/0105729 A1 | 4/2009 | Zentgraf |
| 2009/0105751 A1 | 4/2009 | Zentgraf |
| 2009/0276038 A1 | 11/2009 | Tremulis et al. |
| 2010/0023117 A1 | 1/2010 | Yoganathan et al. |
| 2010/0023118 A1 | 1/2010 | Medlock et al. |
| 2010/0042147 A1 | 2/2010 | Janovsky et al. |
| 2010/0174297 A1 | 7/2010 | Speziali |
| 2010/0179574 A1 | 7/2010 | Longoria et al. |
| 2010/0210899 A1 | 8/2010 | Schankereli |
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketai et al. |
| 2011/0106106 A1 | 5/2011 | Meier et al. |
| 2011/0144743 A1 | 6/2011 | Lattouf |
| 2011/0264208 A1 | 10/2011 | Duffy et al. |
| 2011/0270278 A1 | 11/2011 | Overes et al. |
| 2011/0288637 A1 | 11/2011 | De Marchena |
| 2011/0307055 A1 | 12/2011 | Goldfarb et al. |
| 2012/0004669 A1 | 1/2012 | Overes et al. |
| 2012/0143215 A1 | 6/2012 | Corrao et al. |
| 2012/0150223 A1 | 6/2012 | Manos et al. |
| 2012/0179184 A1 | 7/2012 | Orlov |
| 2012/0184971 A1 | 7/2012 | Zentgraf et al. |
| 2012/0203072 A1 | 8/2012 | Lattouf et al. |
| 2012/0226294 A1 | 9/2012 | Tuval |
| 2012/0226349 A1 | 9/2012 | Tuval et al. |
| 2013/0018459 A1 | 1/2013 | Maisano et al. |
| 2013/0035757 A1 | 2/2013 | Zentgraf et al. |
| 2013/0116710 A1* | 5/2013 | Ziniti ............... A61B 17/0469 606/144 |
| 2013/0253641 A1 | 9/2013 | Lattouf |
| 2013/0282059 A1 | 10/2013 | Ketai et al. |
| 2013/0345749 A1 | 12/2013 | Sullivan et al. |
| 2014/0031926 A1 | 1/2014 | Kudlik et al. |
| 2014/0039607 A1 | 2/2014 | Kovach |
| 2014/0067052 A1 | 3/2014 | Chau et al. |
| 2014/0114404 A1 | 4/2014 | Gammie et al. |
| 2014/0214152 A1 | 7/2014 | Bielefeld |
| 2014/0243968 A1 | 8/2014 | Padala |
| 2014/0364938 A1 | 12/2014 | Longoria et al. |
| 2015/0032127 A1 | 1/2015 | Gammie et al. |
| 2015/0045879 A1 | 2/2015 | Longoria et al. |
| 2015/0250590 A1 | 9/2015 | Gries et al. |

FOREIGN PATENT DOCUMENTS

| | | |
|---|---|---|
| JP | 2013517110 A | 5/2013 |
| WO | 9747246 A1 | 12/1997 |
| WO | 2004037463 A1 | 5/2004 |
| WO | 2006127509 A2 | 11/2006 |
| WO | 2007119057 A1 | 10/2007 |
| WO | 2008013869 A2 | 1/2008 |
| WO | 2007100268 A3 | 10/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |

OTHER PUBLICATIONS

Braunberger, E. et al., "Very long-term results (more than 20 years) of valve repair with Carpentier's echniques in nonheumatic mitral valve insufficiency," (2001) Circulation, I 04:1-8-1-11.

Carpenter, Alain, "Cardiac valve surgery—the 'French coffection'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," (1991) J. Thorne. Cardiovasc. Surg., 101 (3 ):495-50 I.

David, T. E. et al., "Replacement of chordae tendineae with Gore-Tex sutures: a ten-year experience," (1996) J. Heart Valve Dis., 5(4):352-355.

Doty, D. B. et al., "Full-Spectrum Cardiac Surgery Through a Minimal Incision: Mini-Sternotomy (Lower Half) Technique," (1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitrnl valve prolapse," (1997) J. Heal1 Valve Dis., 6(6):594-598.

Frater, R. W. M. ct al., "Chordal replacement in mitral valve repair," (1990) Circulation, 82(suppl. IV):IV-125-IV-130.

Frater, R. W. M., "Anatomical rules for the plastic repair of a diseased mitral valve," (1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitral Repair in Patients With Ischernic Left Ventricular Dysfunction and Functional Mitral Regurgitation," (2003) Ann. Thorne. Surg., 75:809-811.

Kasegawa, H. ct al., "Simple method for detennining proper length of al1ificial chordae in mitral valve repair," (1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European Journal of Cardio-thorncic Surgery, 17(3):201-205.

Merendino, K. A. et al., "The open con-ection of rheumatic mitral regurgitation and/or stenosis with special reference to regurgitation treated by posterornedial annuloplasty utilizing a pump-oxygenator," (1959) Annals of Surgery, 150(1 ):5-22.

Minatoya, K. et al., "Pathologic aspects of polytetrafluoroethylene sutures in human heart," (1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *Iiniversity of Maryland, Baltimore*, Case No. IPR2016-00208, Petition for inter ParlesReview of U.S. Pat. No. 7,635,386, dated Nov. 18, 2015, 65 pages.

(56) References Cited

OTHER PUBLICATIONS

*Neochord, Inc. v. University of Maryland, Bal Tim Ore*, Case No. JPR2016-00208, Decision on Institution of Inter Faries Review,37 CFR §42. I 08, Paper 6, Entered May 24, 2016, 28 pages.
*Neochord, Inc. v. University of Maryland, Baltimore*, Case No. IPR2016-00208, Declaration of Dr. Lishan Aklog, dated Nov. 17, 2015, 91 pages.
Nigro, J. J. et al., "Neochordal repair of the posterior mitral leaflet," (2004) J. Thorne. Cardiovasc. Surg., 127(2):440-447.
Phillips, M. R. et al., "Repair of anterior leaflet mitral valve prolapse: chordal replacement versus chordal shrntening," (2000) Ann. Thorac. Surg., 69(1 ):25-29.
Russo, M. J. ct al. Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet <URL: http://dx.doi.org/J 0.1155/2013/92531 O> Apr. 11, 2013, 4 pages.
Sarsam, M.A. I., "Simplified technique for determining the length of artificial cl1ordae in milral valve repair," (2002) Ann. Thorac. Surg., 73(5): 1659-1660.
Savage, E. B. et al., Use of mitral valve repair: analysis of contemporary United States experience reported to the society of thoracic surgeons national cardiac database, .. (2003) Ann. Thorne. Surg., 75:820-825.

Speziali, G. et al., "Colrection of Mitral Valve Regurgitation by Off-Pump, Transapical Placement of Artificial Chordae Tendinae, Results of the European TACT Trial," AATS 93rd Annual Meeting 2013, www.aats.org, 26 pages.
Suematsu, Y. et al., "Three-dimensional echo-guided beating heaii surgery without cardiopulmonary bypass: Atrial septal defect closure in a swine model," (2005) J. Thorne. Cardiovasc. Surg., 130: 1348-1357.
Von Oppell, U. 0. et al., "Chordal replacement for both minimally invasive and conventional mitral valve surgery using prcrncasurcd Gore-Tex loops," (2000) Ann. Thorne. Surg., 70(6):2166-2168.
Zussa, C. et al., Artificial mitral valve chordae: experimental and clinical experience; ( 1990) Ann. Thorne. Sum., 50(3):367-373.
Zussa, C. et al., "Seven-year experience with chordal replacement with expanded polytetrafluoroethylene in floppyrnitral valve," (1994)1. Thorac. Cardiovasc. Surg., 108(1):37-41.
Zussa, C. et al., "Surgical technique for artificial mitral chordae implantation," ( 1991) Journal of Cardiac Surgery, 6(4):432-438.
Zussa, C., "Artificial chordae," (1995) J. Heart Valve Dis., 4(2):S249-S256.
Alfieri, 0. el al.; "The double-orifice technique in mitral valve repair: a simple solution for complex problems," (2001) J. Thorne. Cardiovasc. Surg., 122(4):674-681.

* cited by examiner

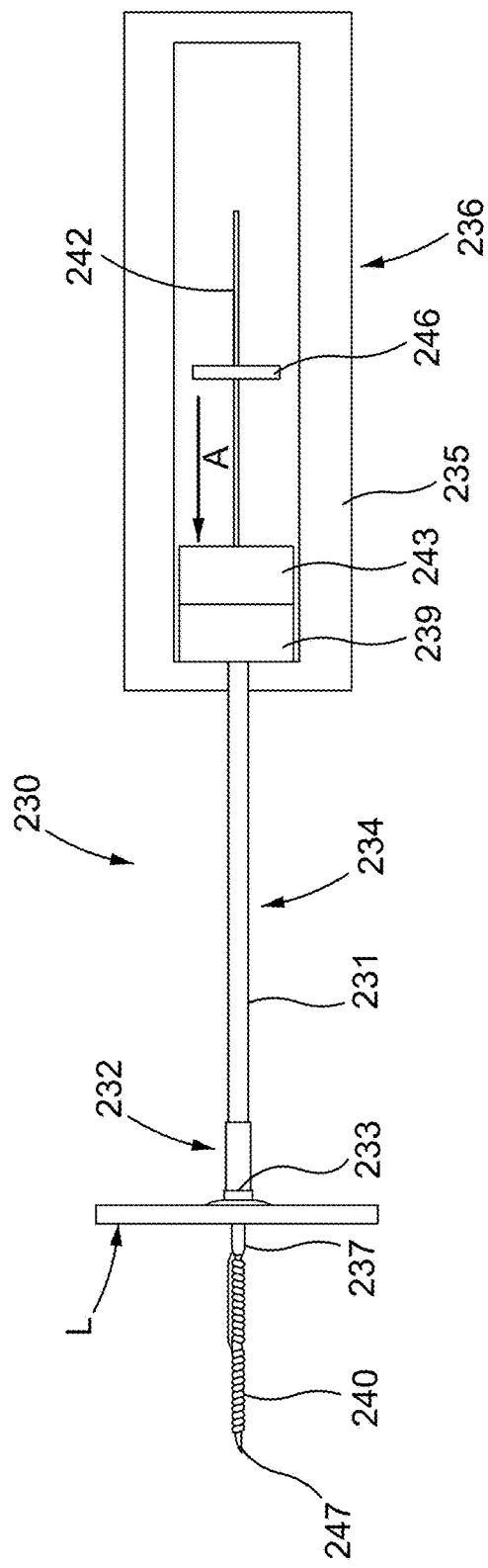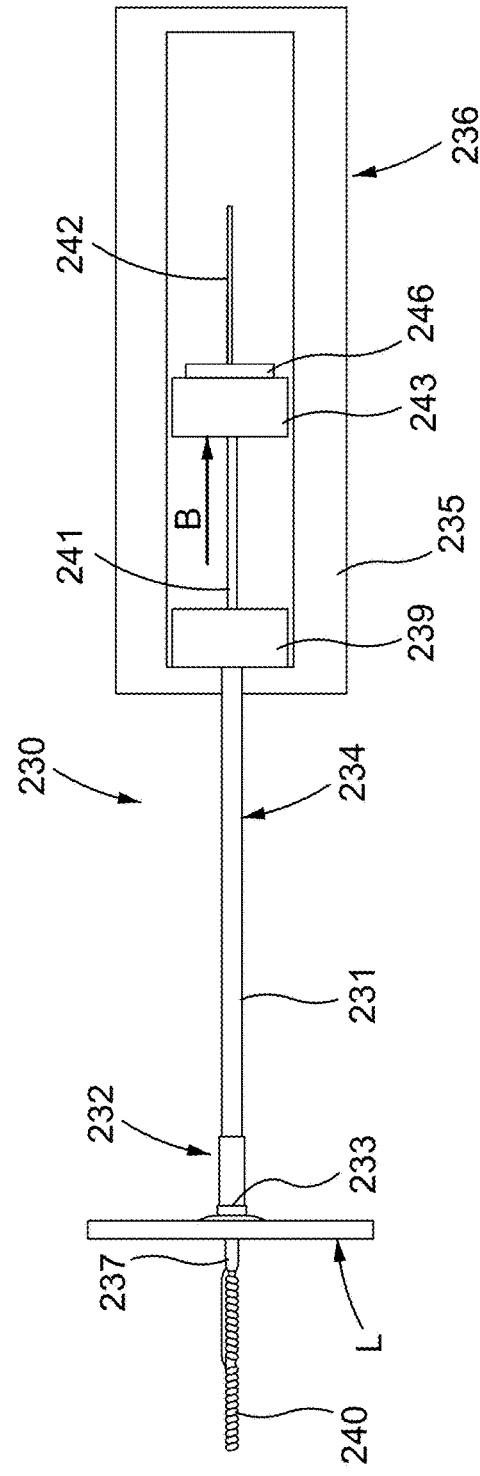

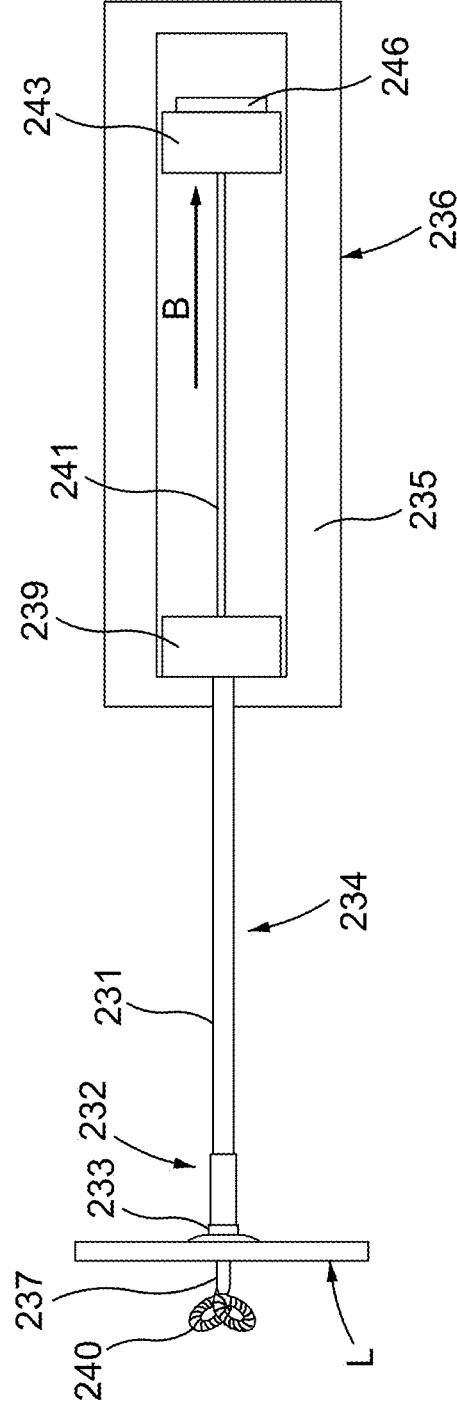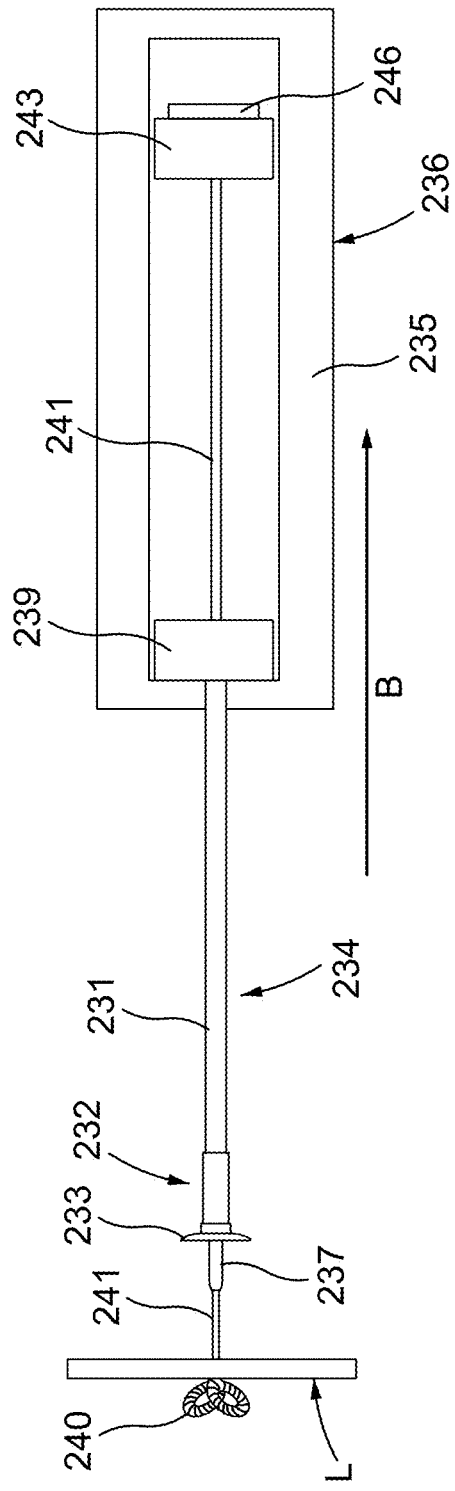

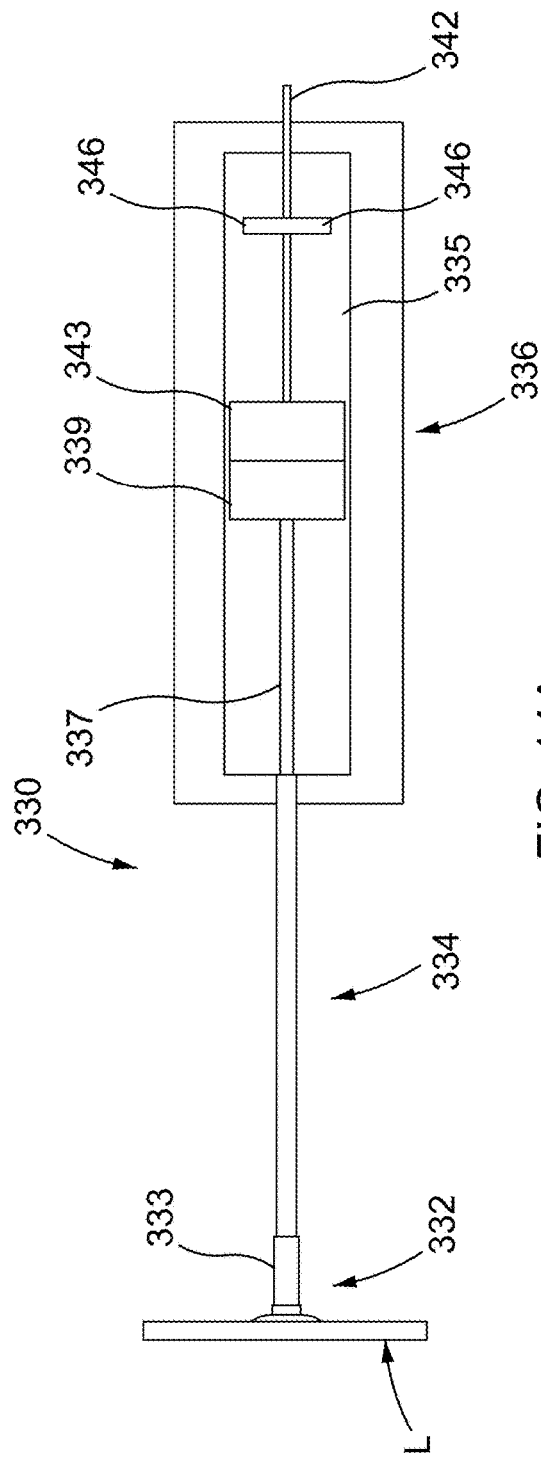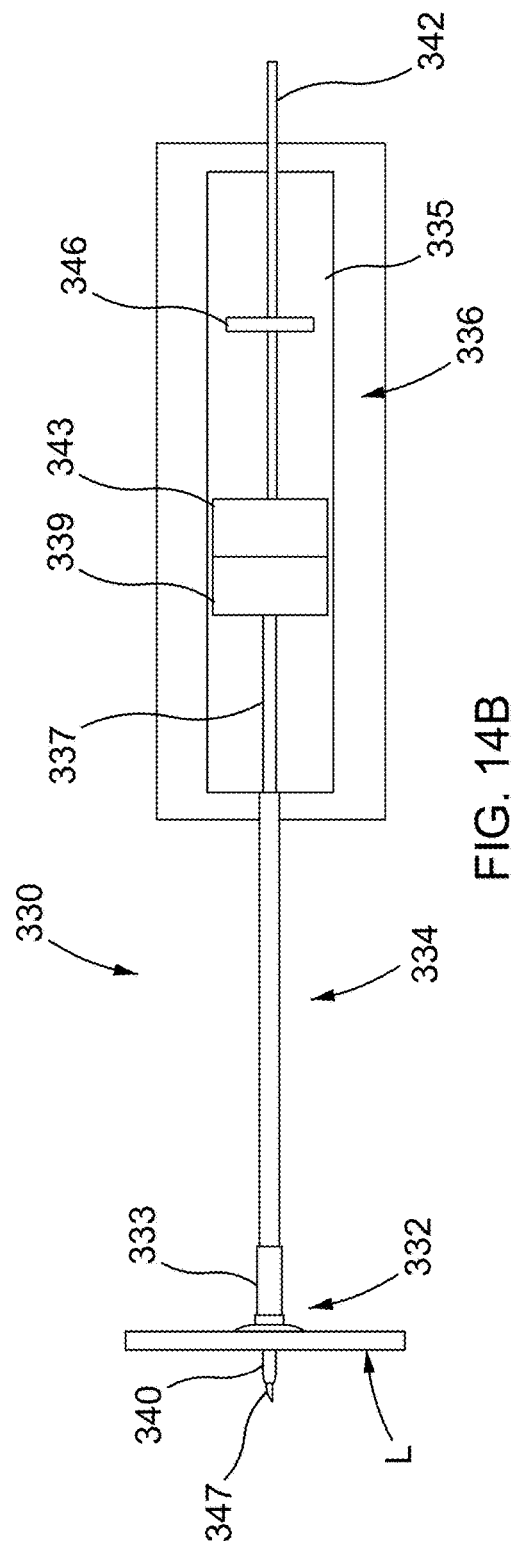
FIG. 14A
FIG. 14B

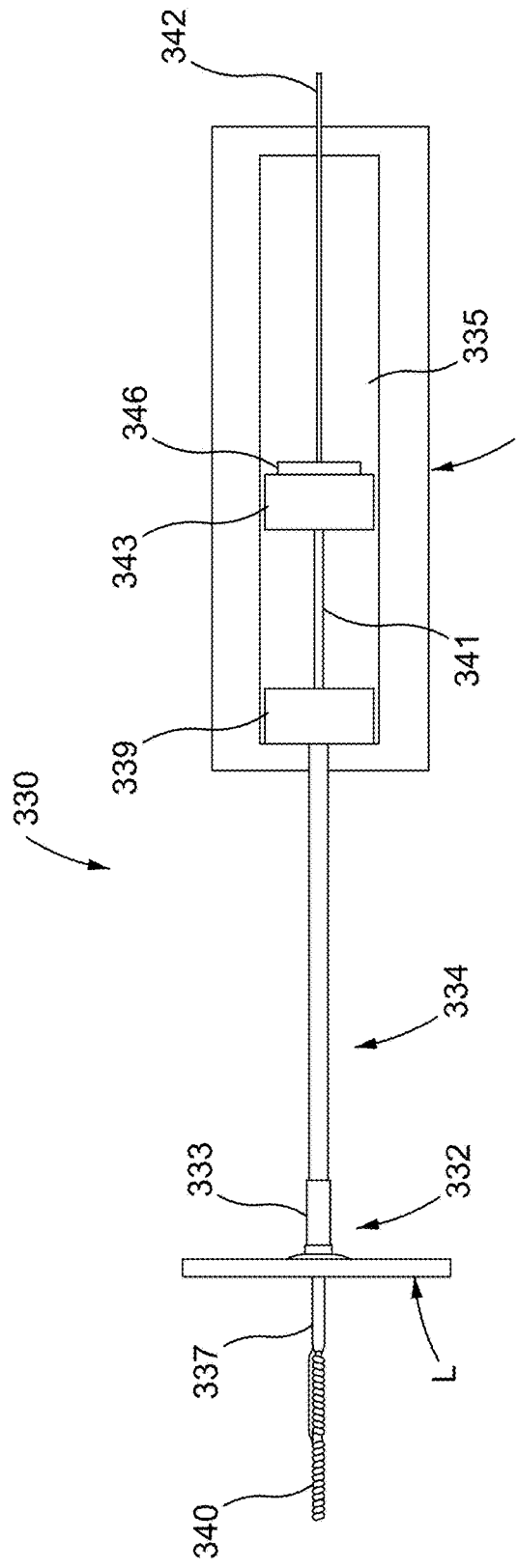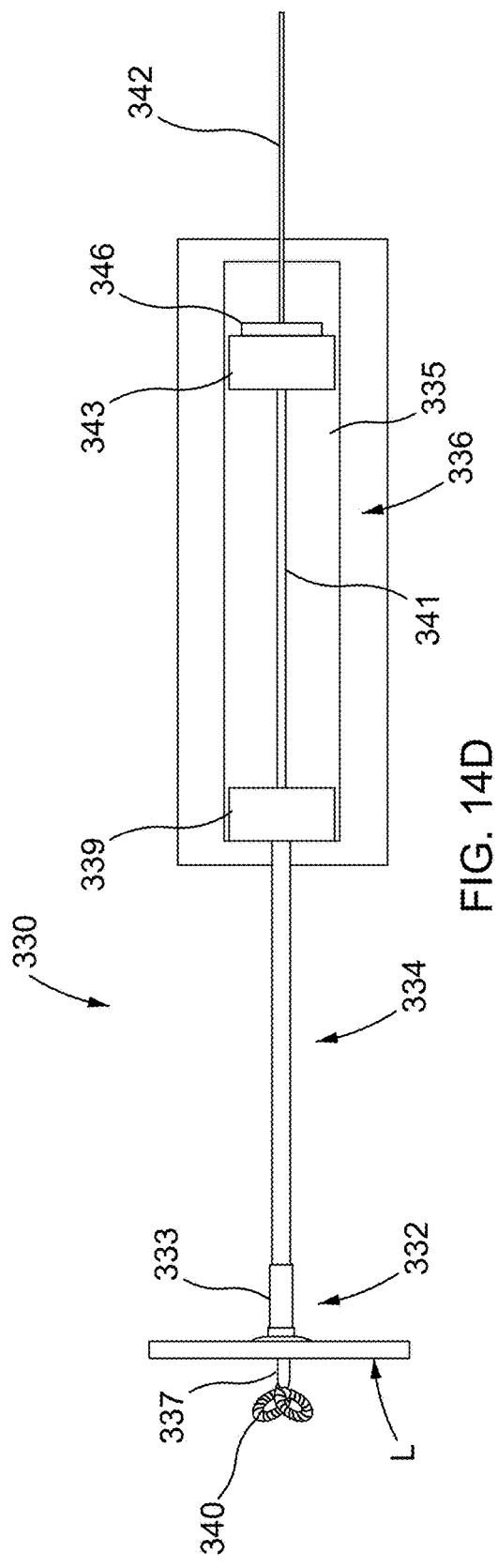

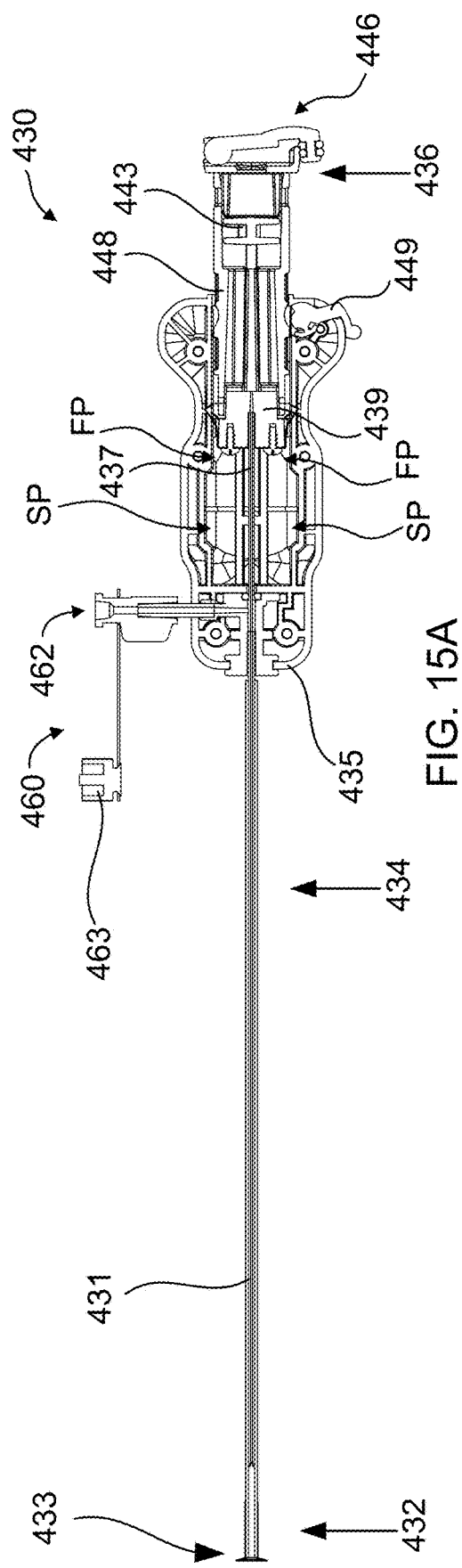
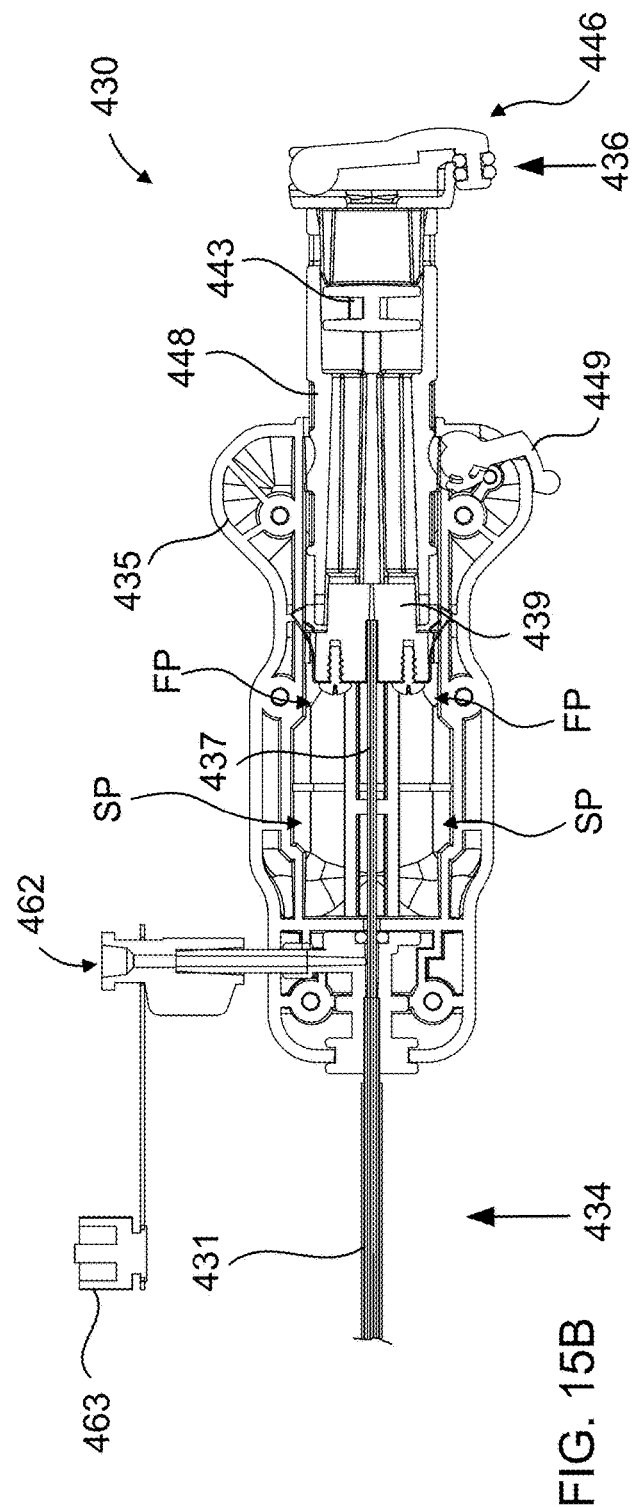
FIG. 15A
FIG. 15B

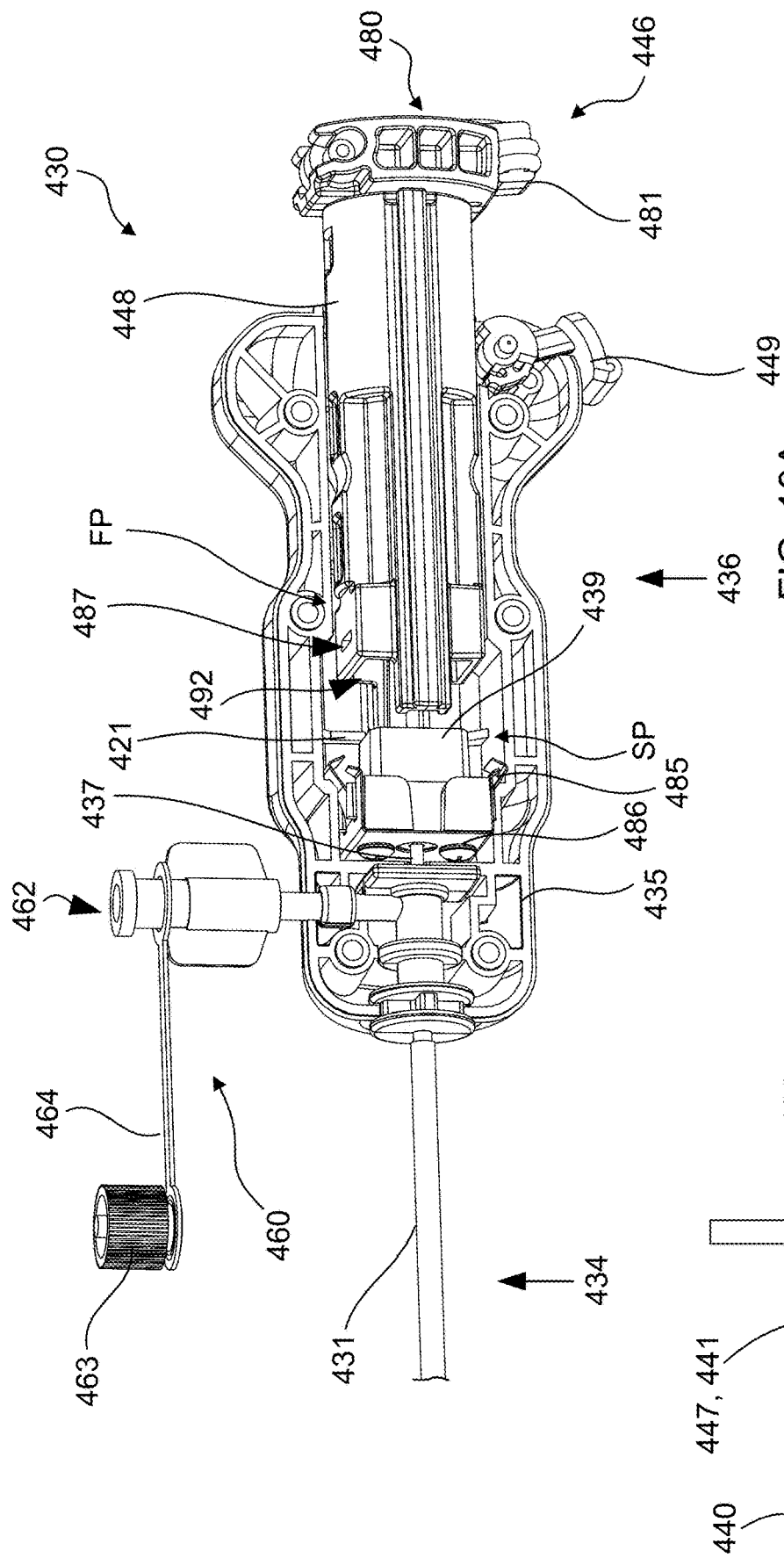
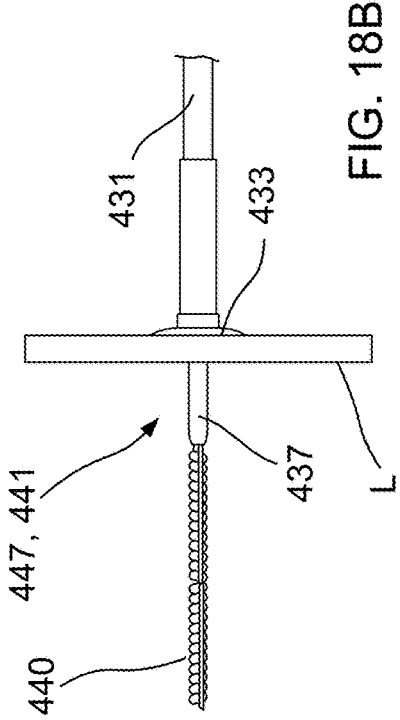
FIG. 18A
FIG. 18B

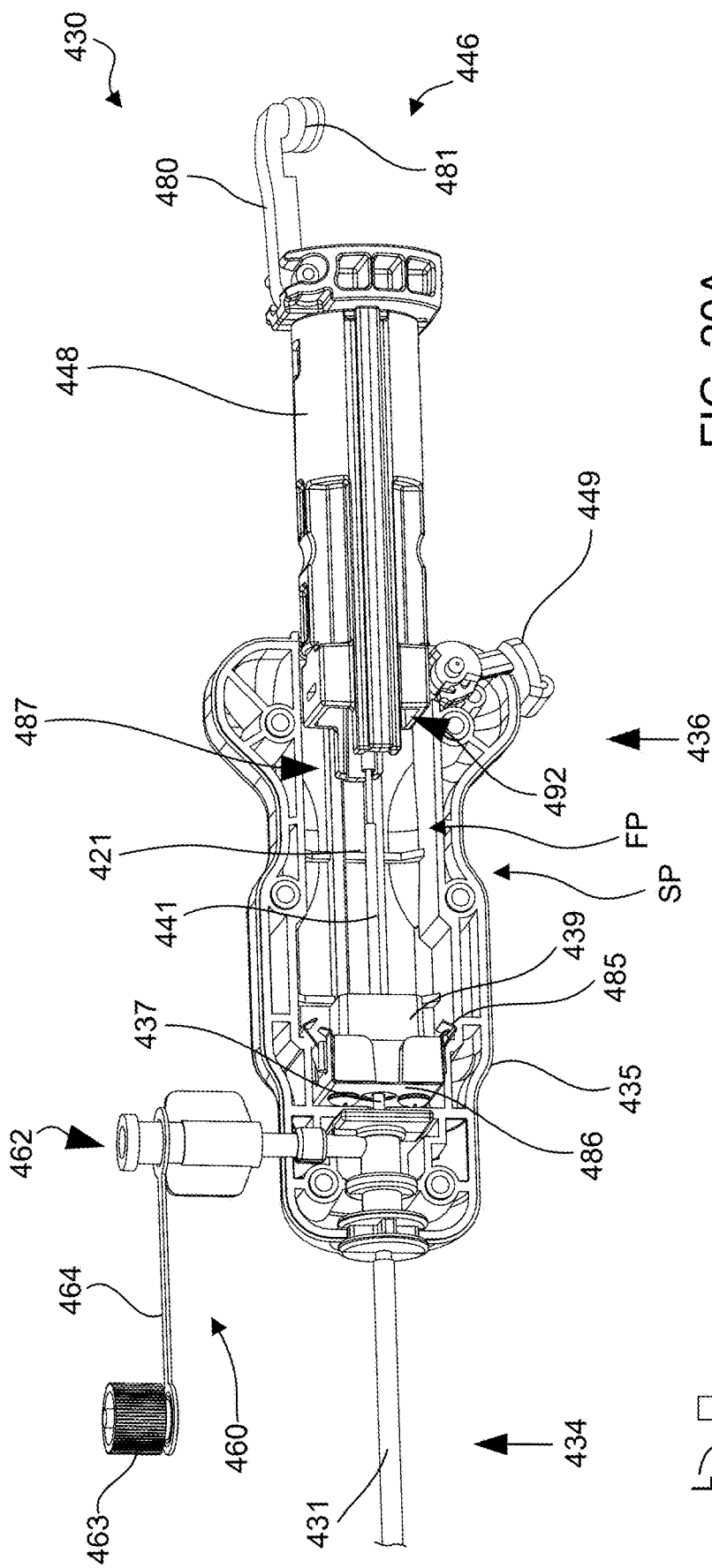
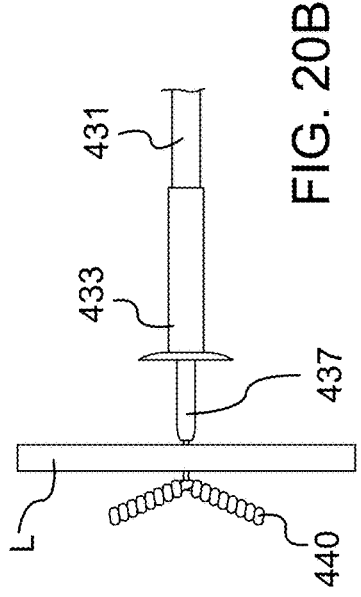
FIG. 20A
FIG. 20B

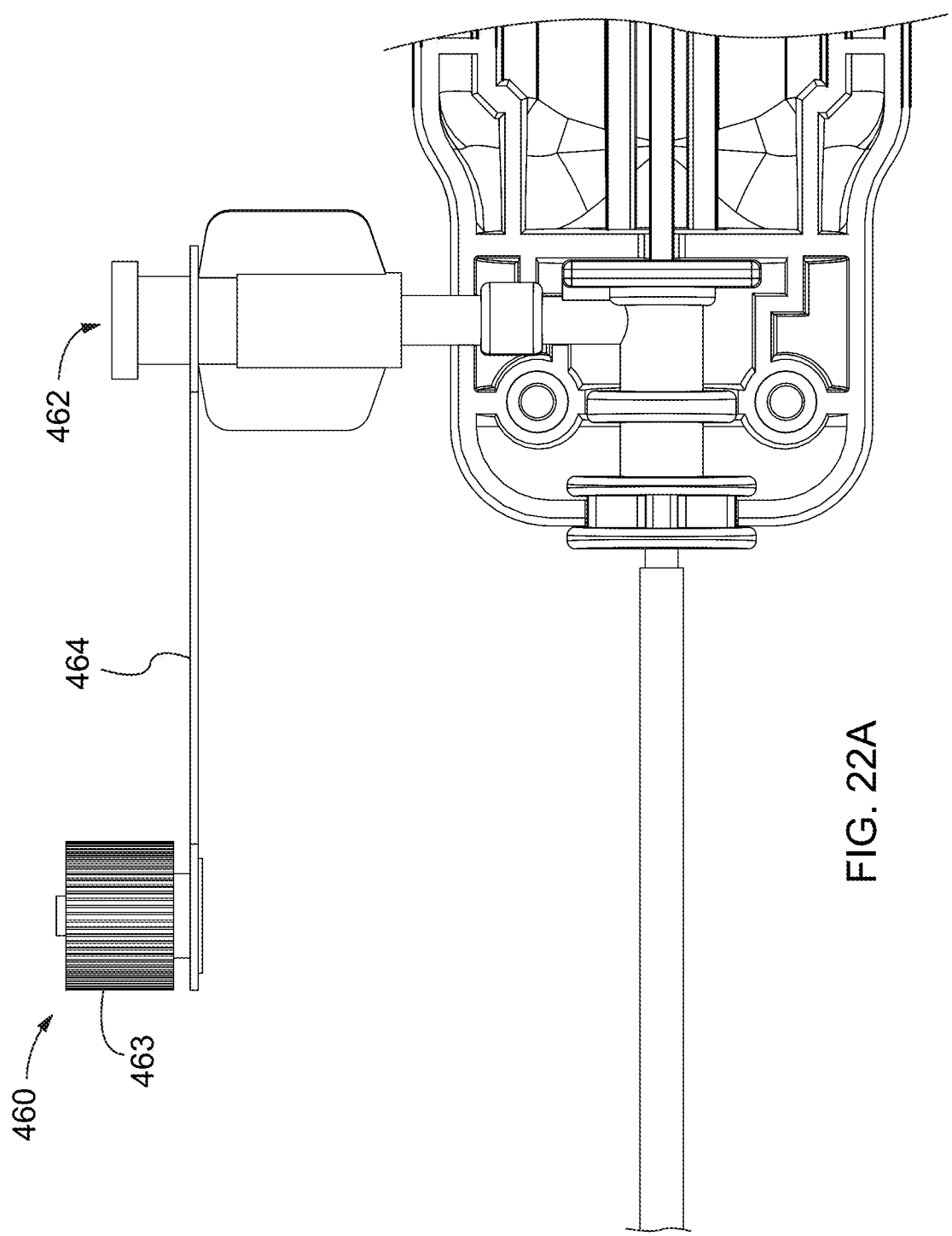

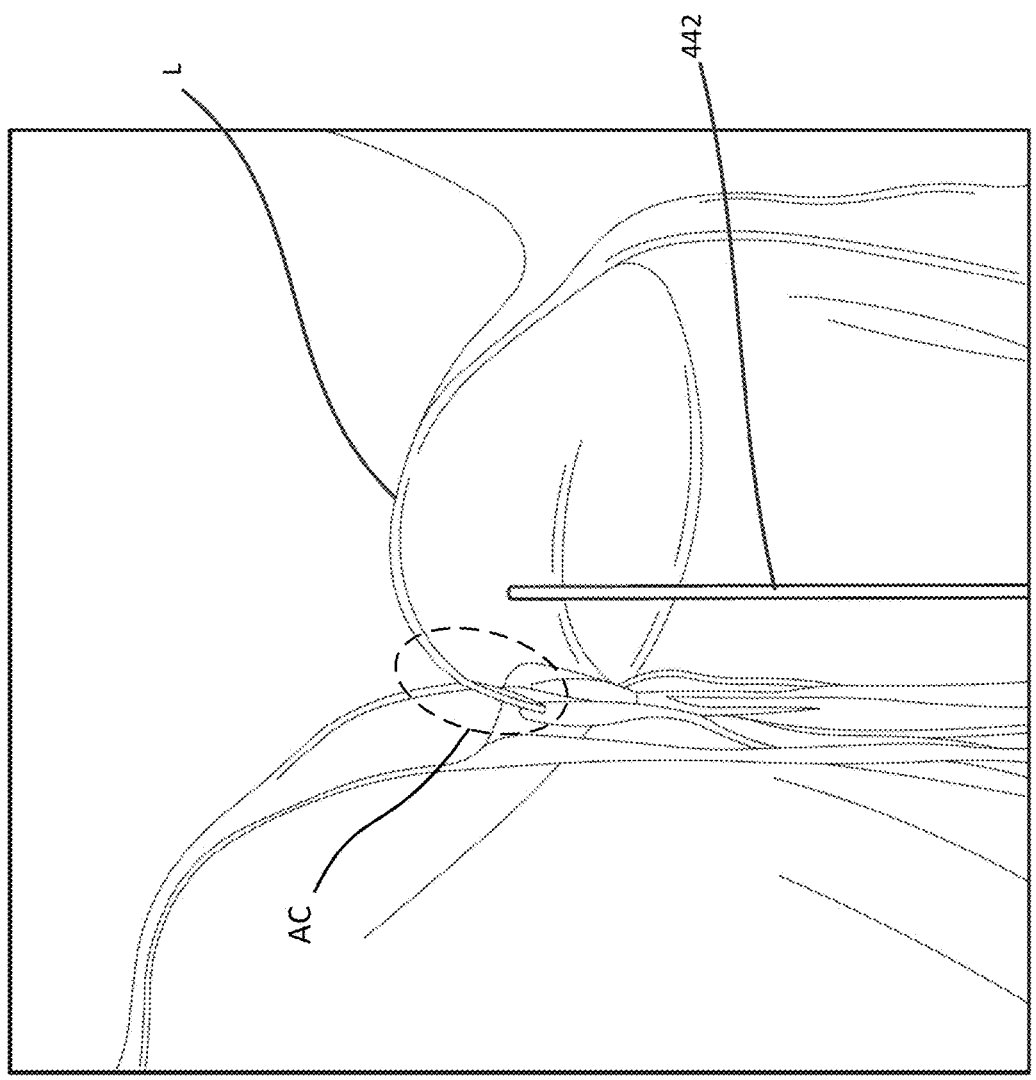

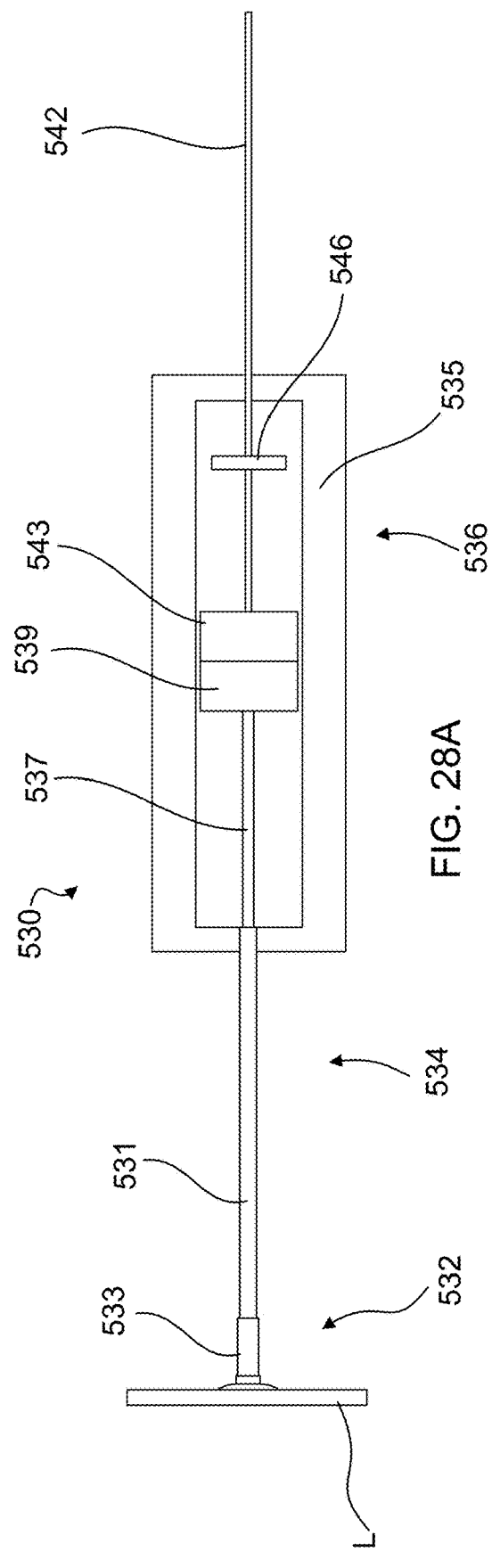
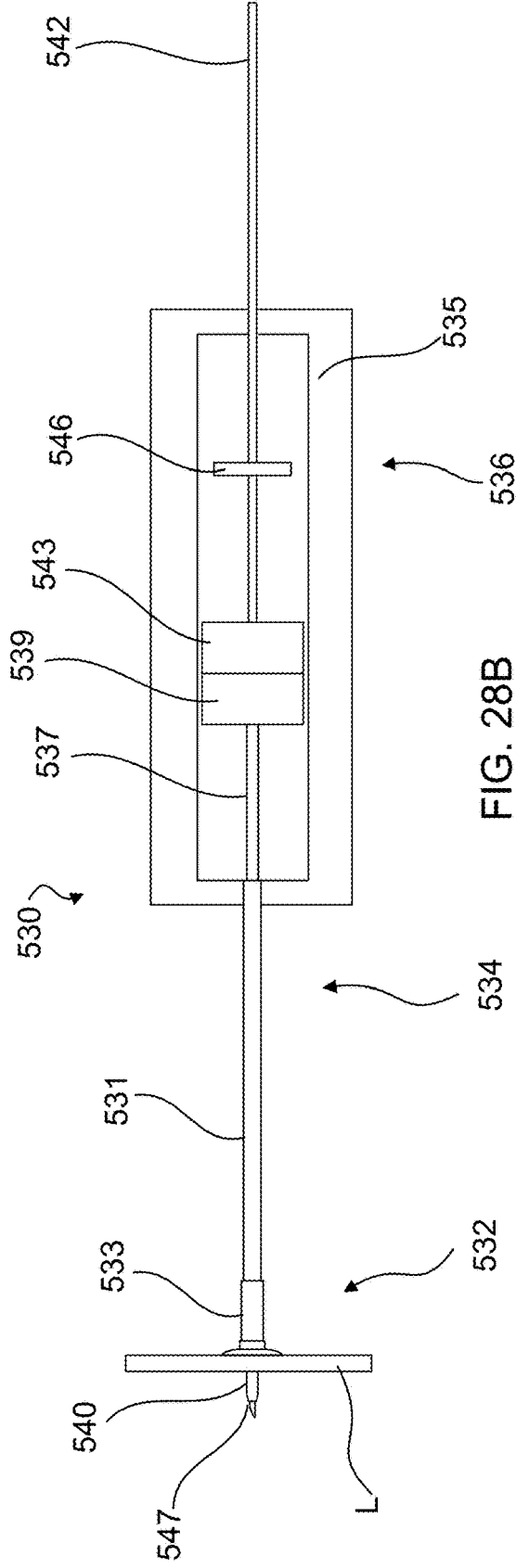

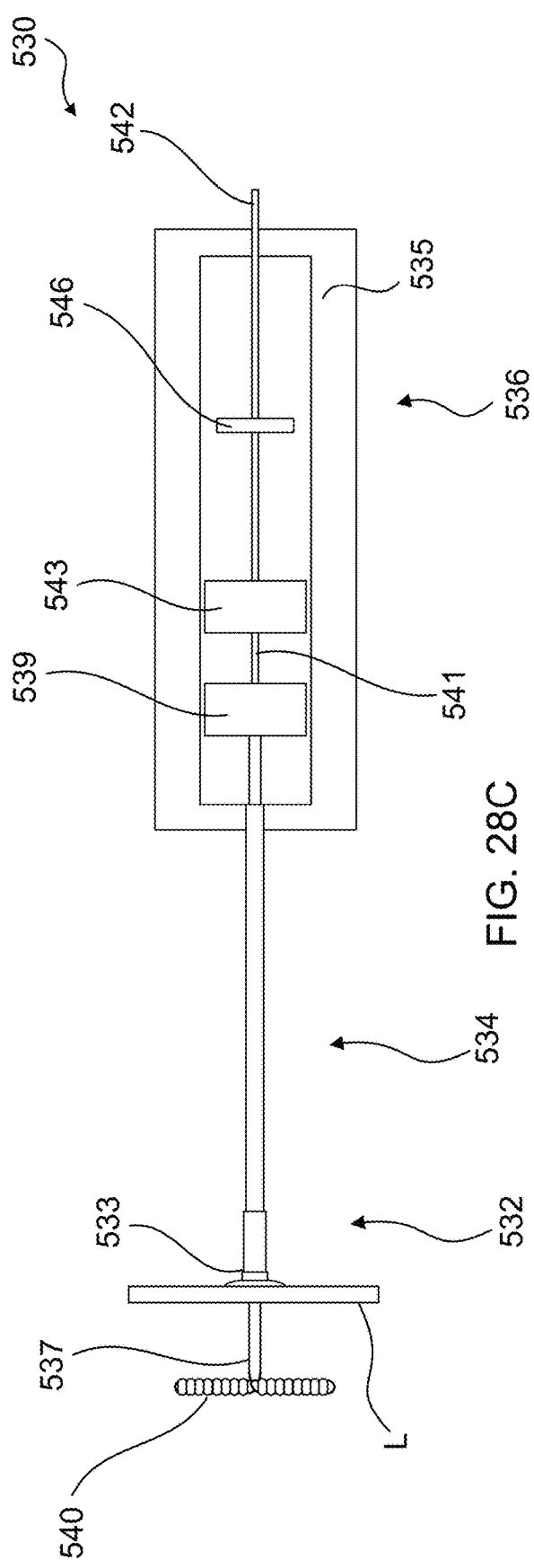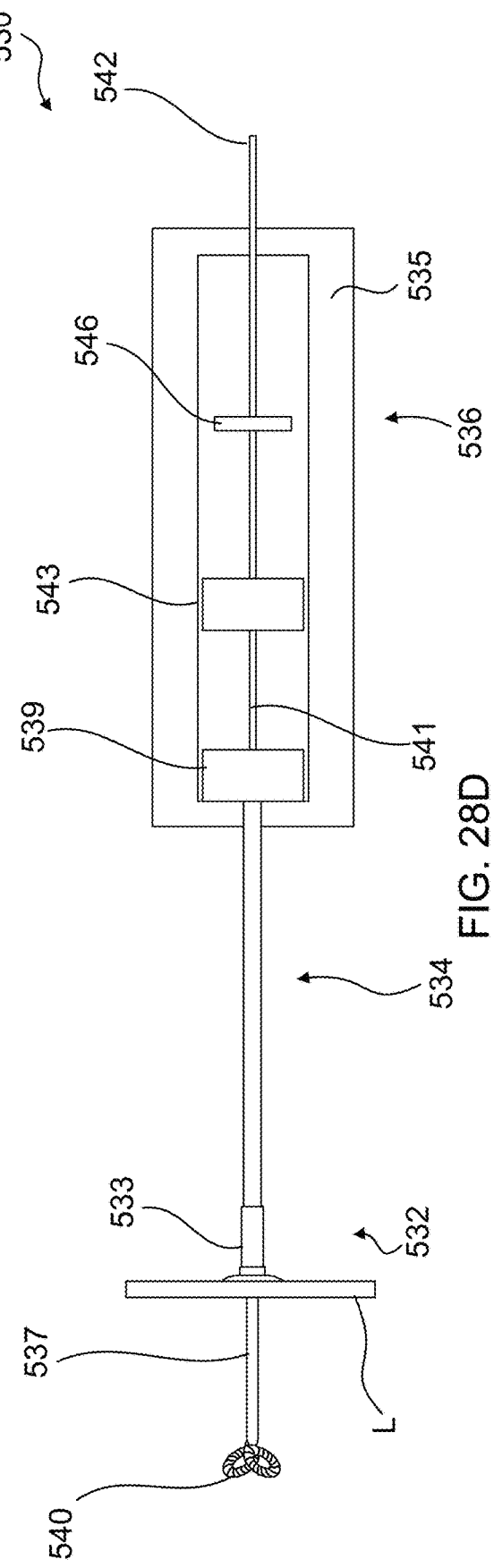

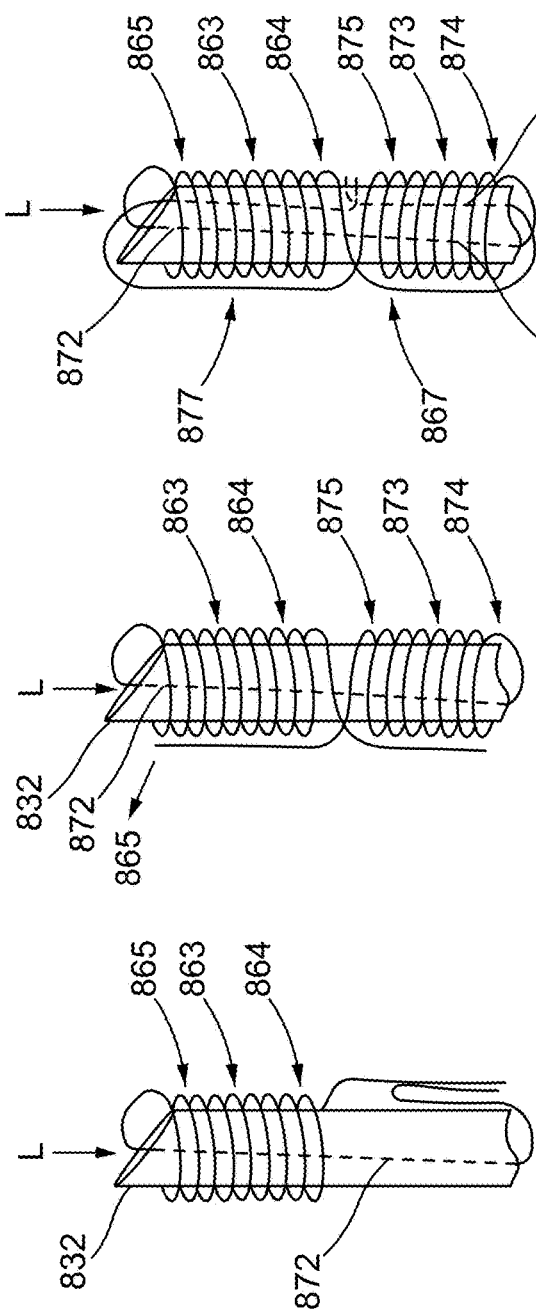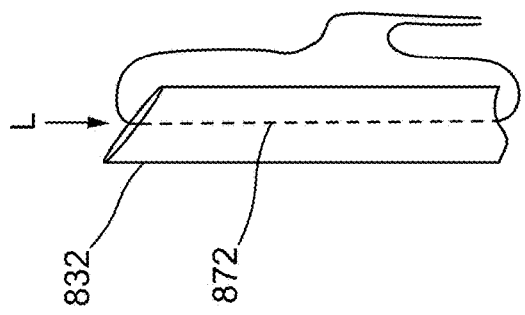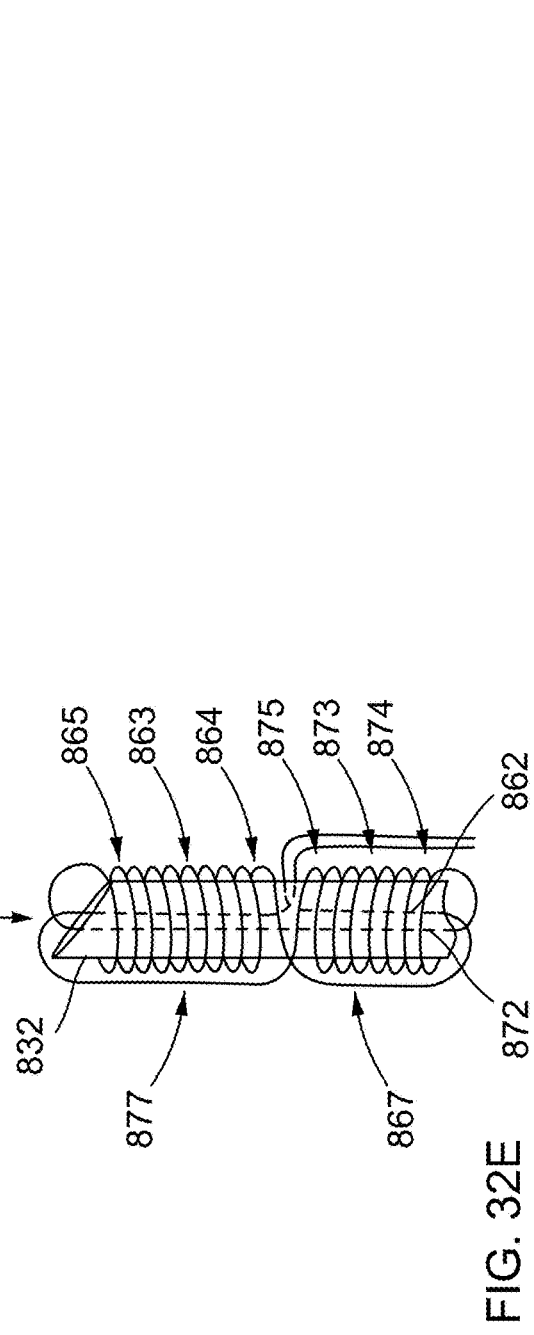

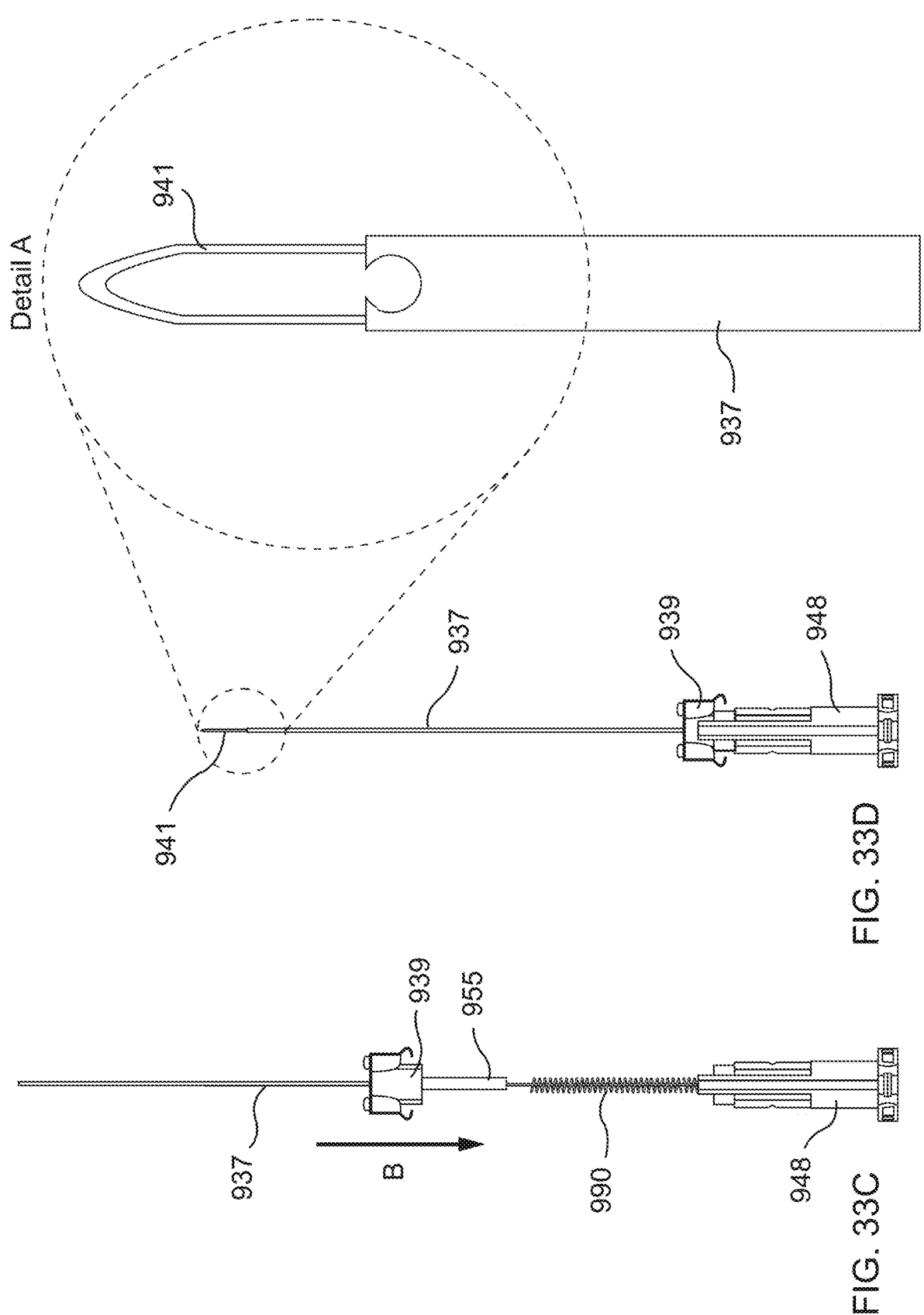

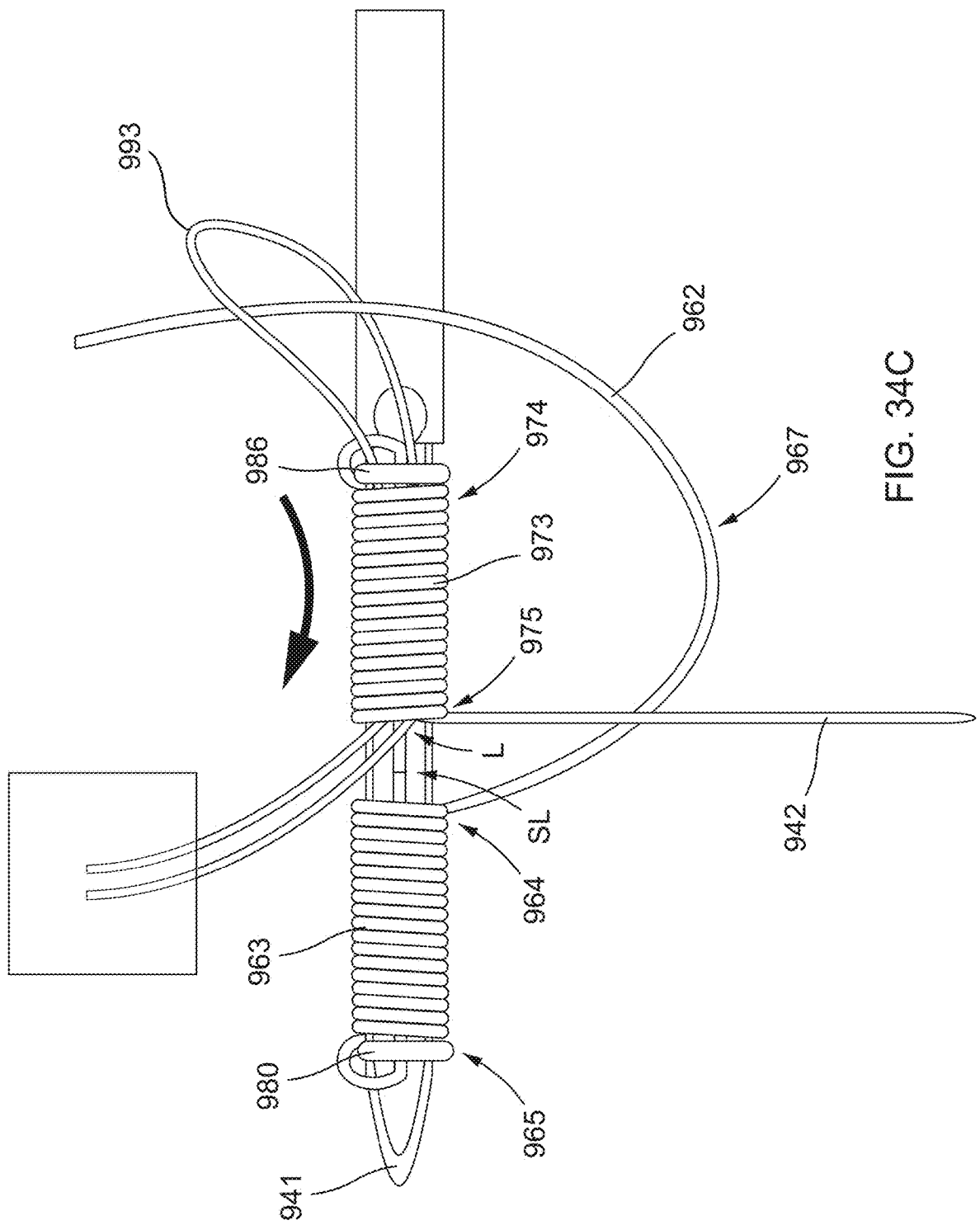

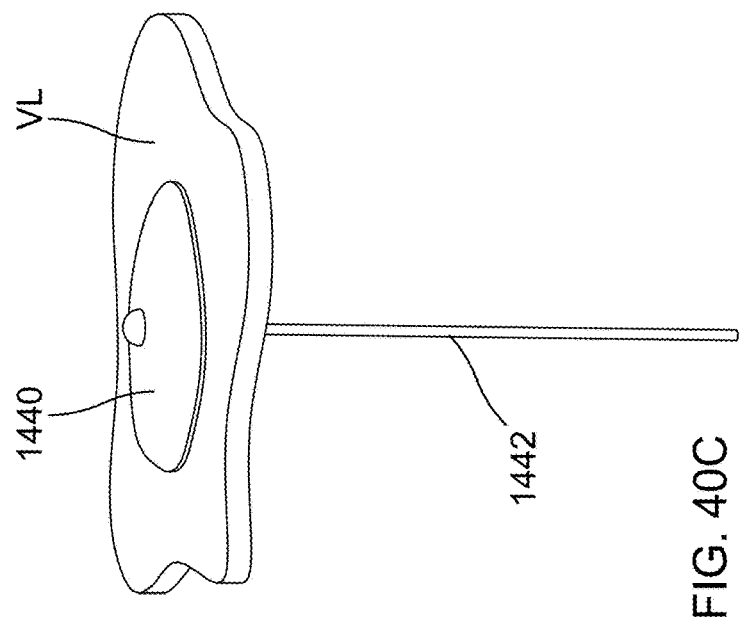
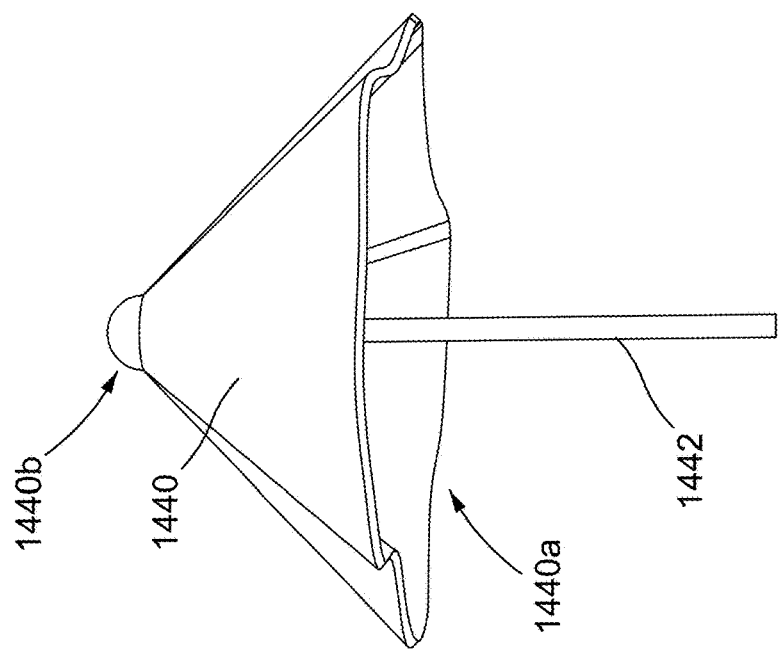
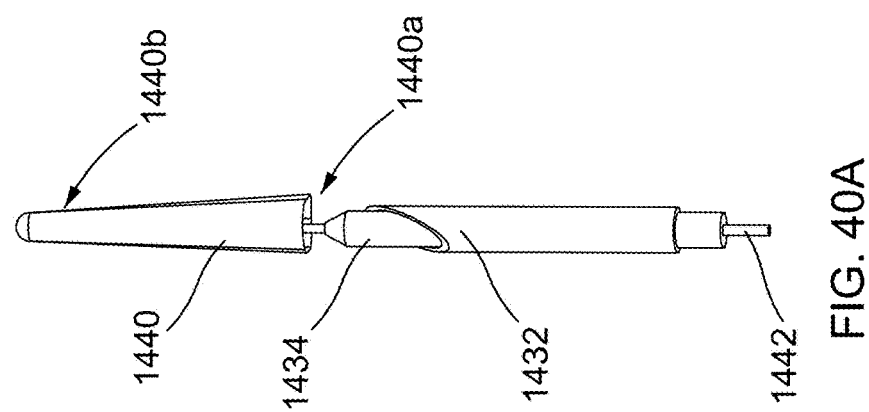

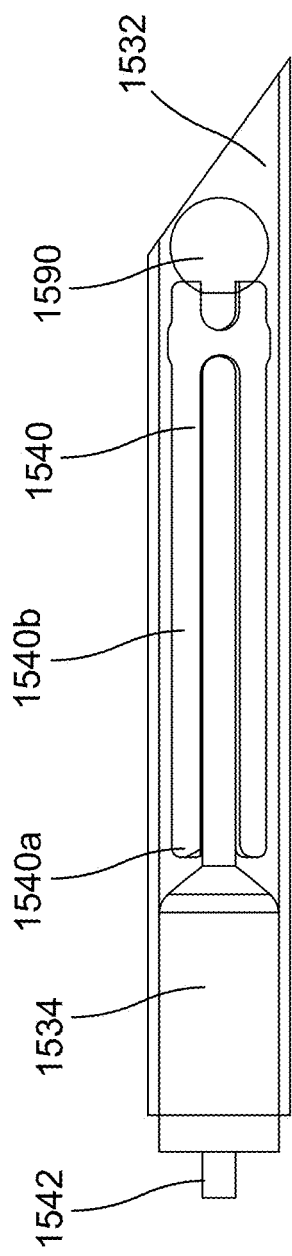
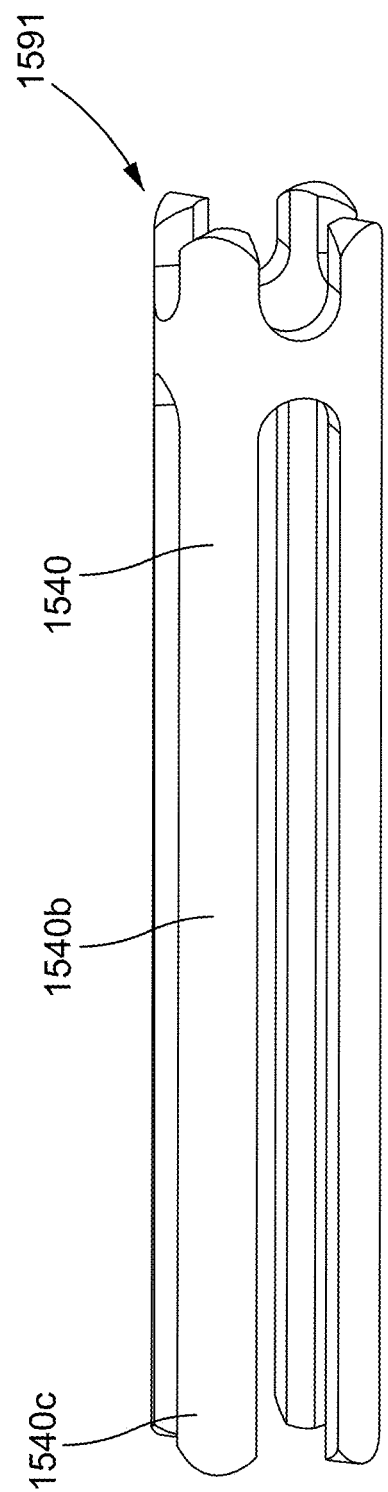
FIG. 41A
FIG. 41B

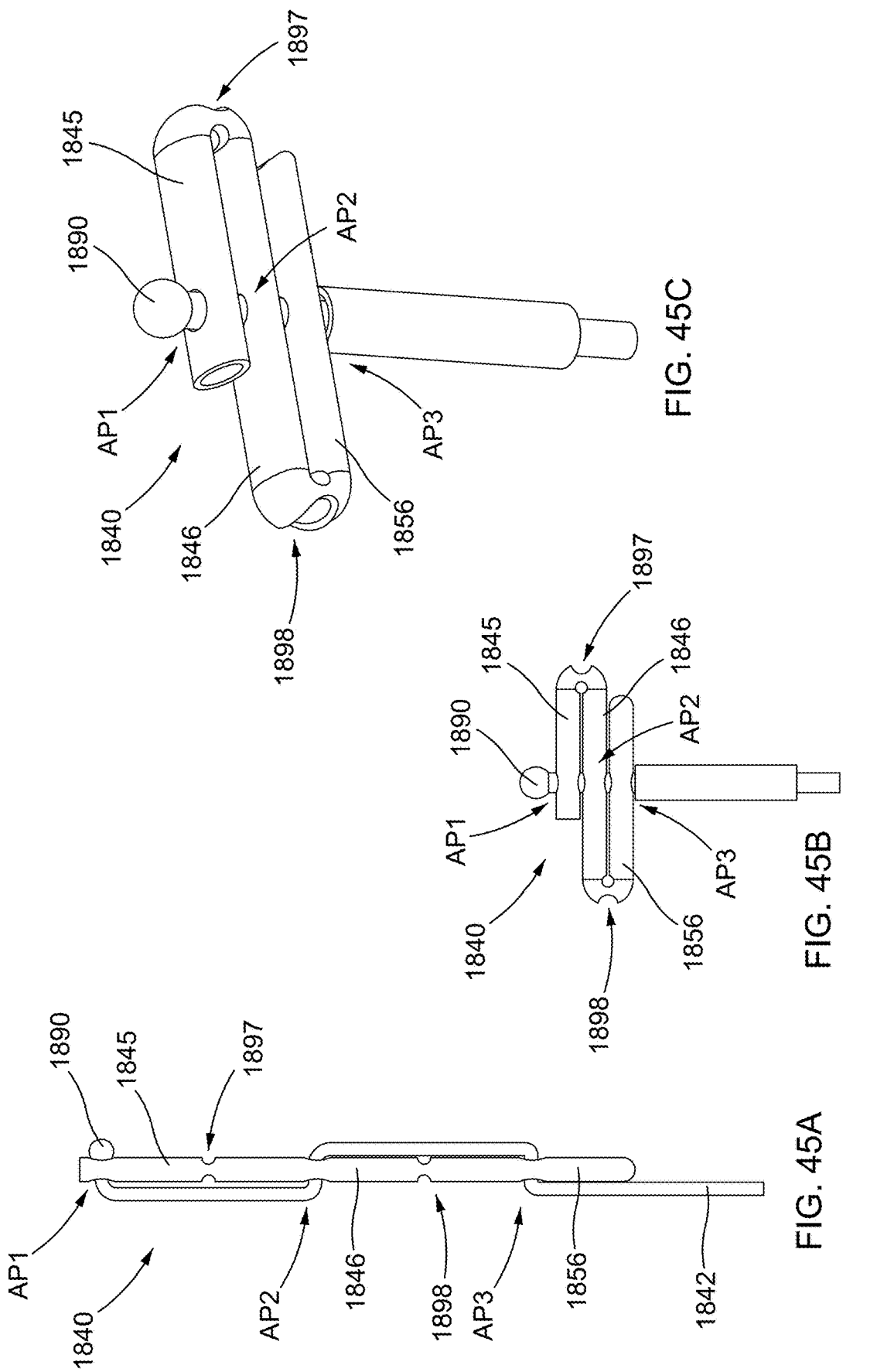

DISTAL ANCHOR APPARATUS AND METHODS FOR MITRAL VALVE REPAIR

CROSS-REFERENCE TO RELATED APPLICATIONS

This application is a continuation of International Application No. PCT/US2016/055170, filed on Oct. 3, 2016, which claims the benefit of U.S. Application No. 62/315,879, filed on Mar. 31, 2016; and U.S. Application No. 62/236,225, filed on Oct. 2, 2015, all of the disclosures of which are incorporated herein by reference in their entireties.

BACKGROUND

Some embodiments described herein relate to methods and apparatus for performing cardiac valve repairs, and more particularly, methods and apparatus for performing minimally invasive mitral or tricuspid valve repairs.

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease), and infectious processes (e.g., endocarditis). Additionally, damage to the ventricle from prior heart attacks (i.e., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in a leaflet of the valve, which results in prolapse and regurgitation.

Generally, a heart valve may malfunction in two different ways. One possible malfunction, valve stenosis, occurs when a valve does not open completely and thereby causes an obstruction of blood flow. Typically, stenosis results from buildup of calcified material on the leaflets of the valves causing them to thicken and thereby impairing their ability to fully open and permit adequate forward blood flow.

Another possible malfunction, valve regurgitation, occurs when the leaflets of the valve do not close completely thereby causing blood to leak back into the prior chamber. There are three mechanisms by which a valve becomes regurgitant or incompetent; they include Carpentier's type I, type II and type III malfunctions. A Carpentier type I malfunction involves the dilation of the annulus such that the area of the valve orifice increases. The otherwise normally functioning leaflets do not have enough surface area to cover the enlarged orifice and fail to form a tight seal (i.e., do not coapt properly) causing regurgitation. Included in a type I mechanism malfunction are perforations of the valve leaflets, as in endocarditis. A Carpentier's type II malfunction involves prolapse of a segment of one or both leaflets above the plane of the annulus. This is the most common cause of mitral regurgitation, and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

Mitral valve disease is the most common valvular heart disorder, with nearly 4 million Americans estimated to have moderate to severe mitral valve regurgitation ("MR"). MR results in a volume overload on the left ventricle which in turn progresses to ventricular dilation, decreased ejection performance, pulmonary hypertension, symptomatic congestive heart failure, atrial fibrillation, right ventricular dysfunction and eventually death. Successful surgical mitral valve repair restores mitral valve competence, abolishes the volume overload on the left ventricle, improves symptom status, prevents adverse left ventricular remodeling and dramatically improves life expectancy, often returning it to that of a normal member of the population.

Malfunctioning valves may either be repaired or replaced. Repair typically involves the preservation and correction of the patient's own valve. Replacement typically involves replacing the patient's malfunctioning valve with a biological or mechanical substitute. Typically, replacement is preferred for stenotic damage sustained by the leaflets because the stenosis is irreversible. The mitral valve and tricuspid valve, on the other hand, are more prone to deformation. Deformation of the leaflets, as described above, prevents the valves from closing properly and allows for regurgitation or back flow from the ventricle into the atrium, which results in valvular insufficiency. Deformations in the structure or shape of the mitral valve or tricuspid valve are often repairable.

In mitral valve regurgitation, repair is preferable to valve replacement. Mitral valve replacement operations have a 2× higher risk of operative mortality (Risk Standardized Mortality 1.65% vs 2.96%), 2× higher risk of stroke per year (1.15%±0.1% vs 2.2%±0.4%) and a 10× higher risk of infection per year (0.1% vs 1.0%). Patients who receive a quality mitral valve repair operation do not require anticoagulation and rarely require reoperation. This is in stark contrast to mechanical valve replacement which mandates lifelong anticoagulation and bioprosthetic valve replacement with the eventual certainty of prosthetic valve dysfunction and reoperation. Compared to mitral valve replacement, mitral valve repair results in improved left ventricular function and has superior long term survival. Therefore, an improperly functioning mitral valve or tricuspid valve is ideally repaired, rather than replaced. However, because of the complex and technical demands of the repair procedures, the mitral valve is still replaced in approximately one third of all mitral valve operations performed in the United States.

Studies suggest that Carpentier type II malfunction, often referred to as "Degenerative," "Primary" or "Organic" MR, accounts for as much as 60% of MR. Resectional mitral valve repair techniques, initially described by Dr. Carpentier, involve cutting out (resecting) a section of the prolapsed leaflet tissue, stitching the remaining tissue together and implanting an annuloplasty ring around the annulus. More recently many surgeons have moved to a "non-resectional" repair technique where artificial chordae tendineae ("neochords") made of ePTFE suture, or another suitable material, are placed in the prolapsed leaflet and secured to the heart in the left ventricle, normally to the papillary muscle. Because the native leaflet tissue is maintained in non-resectional repairs, they often result in a larger surface of coaptation between the posterior and anterior mitral valve leaflets, but properly sizing the neochords on a flaccid heart can be very challenging, especially for the low volume mitral valve surgeon.

Carpentier type I malfunction, sometimes referred to as "Secondary" or "Functional" MR, is associated with heart failure and affects between 1.6 and 2.8 million people in the United States alone. Studies have shown that mortality doubles in patients with untreated mitral valve regurgitation after myocardial infarction. Unfortunately, there is no gold standard surgical treatment paradigm for functional MR and most functional MR patients are not referred for surgical intervention due to the significant morbidity, risk of complications and prolonged disability associated with cardiac surgery. Surgeons use a variety of approaches ranging from valve replacement to insertion of an undersized mitral valve annuloplasty ring for patients suffering from functional MR and the long term efficacy is still unclear. Dr. Alfieri has demonstrated the benefit of securing the midpoint of both leaflets together creating a double orifice valve in patients with MR known as an "Edge-to-Edge" repair or an Alfieri procedure. The ability to combine a neochordal repair with an edge-to-edge repair in degenerative MR patients with a dilated annulus and who do not receive an annuloplasty ring because the repair is done in a minimally-invasive, off-pump procedure, has particular promise.

Regardless of whether a replacement or repair procedure is being performed, conventional approaches for replacing or repairing cardiac valves are typically invasive open-heart surgical procedures, such as sternotomy or thoracotomy, which require opening up of the thoracic cavity so as to gain access to the heart. Once the chest has been opened, the heart is bypassed and stopped. Cardiopulmonary bypass is typically established by inserting cannulae into the superior and inferior vena cavae (for venous drainage) and the ascending aorta (for arterial perfusion), and connecting the cannulae to a heart-lung machine, which functions to oxygenate the venous blood and pump it into the arterial circulation, thereby bypassing the heart. Once cardiopulmonary bypass has been achieved, cardiac standstill is established by clamping the aorta and delivering a "cardioplegia" solution into the aortic root and then into the coronary circulation, which stops the heart from beating. Once cardiac standstill has been achieved, the surgical procedure may be performed. These procedures, however, adversely affect almost all of the organ systems of the body and may lead to complications, such as strokes, myocardial "stunning" or damage, respiratory failure, kidney failure, bleeding, generalized inflammation, and death. The risk of these complications is directly related to the amount of time the heart is stopped ("cross-clamp time") and the amount of time the subject is on the heart-lung machine ("pump time").

Thus, there is a significant need to perform mitral valve repairs using less invasive procedures while the heart is still beating. Accordingly, there is a continuing need for new procedures and devices for performing cardiac valve repairs, such as mitral valve repair, which are less invasive, do not require cardiac arrest, and are less labor-intensive and technically challenging.

SUMMARY

Apparatus and methods for performing a non-invasive procedure to repair a cardiac valve are described herein. In some embodiments, devices to deliver a distal anchor within the atrium of the heart are described herein. Such a device can include a handle, an actuator operably coupled to the handle, a pusher device, a puncture member coupled to the actuator and at least partially disposed within a lumen defined by the pusher device, and a distal anchor. The distal anchor is disposed at a distal end portion of an artificial chorda and disposed in a delivery configuration. The artificial chorda has a proximal end portion coupled to the actuator. The proximal end portion of the artificial chorda extends through a lumen defined by the puncture member. The actuator can be actuated to move the puncture member distally a preset distance, and to move the pusher device distally such that at least a portion of the distal anchor is moved distal to the distal end of the puncture member and the distal anchor is moved from its delivery configuration to a deployed configuration.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIG. 7 is a schematic illustration of the distal anchor delivery device of FIG. 6, shown in a first configuration during deployment of a distal anchor through a mitral leaflet of a heart.

FIG. 8 is a schematic illustration of the distal anchor delivery device of FIG. 6, shown in a second configuration during deployment of a distal anchor.

FIG. 9 is a schematic illustration of the distal anchor delivery device of FIG. 6, shown in a third configuration showing formation of the distal anchor during deployment.

FIG. 10 is a schematic illustration of the distal anchor delivery device of FIG. 6, shown in a fourth configuration showing the delivery device being retracted after deployment of the distal anchor.

FIG. 14A is a schematic illustration of a side view of a distal anchor delivery device according to another embodiment, shown in a first configuration prior to deployment of a distal anchor through a mitral leaflet of a heart.

FIG. 14B is a schematic illustration of a side view of the distal anchor delivery device of FIG. 14A, shown in a second configuration during deployment of a distal anchor through a mitral leaflet of a heart.

FIG. 14C is a schematic illustration of a side view of the distal anchor delivery device of FIG. 14A, shown in a third configuration during deployment of a distal anchor.

FIG. 14D is a schematic illustration of a side view of the distal anchor delivery device of FIG. 14A, shown in a fourth configuration during deployment of the distal anchor.

FIG. 15A is a cross-sectional side view of a distal anchor delivery device, according to another embodiment.

FIG. 15B is an enlarged cross-sectional side view of a portion of the distal anchor delivery device of FIG. 15A.

FIG. 18A is a perspective view shown partially in cross-section of the delivery device of FIG. 15A, shown during deployment of a distal anchor.

FIG. 18B is a side view of a distal end portion of the delivery device of FIG. 15A, shown with the distal anchor in a first configuration.

FIG. 20A is a perspective view shown partially in cross-section of the anchor delivery device of FIG. 15A, shown in a fourth configuration showing the delivery device being retracted after deployment of the distal anchor.

FIG. 20B is a side view of a distal end portion of the delivery device of FIG. 15A, showing the delivery device being retracted after deployment of the distal anchor.

FIGS. 22A-22C are a side view, a top view in cross-section, and a side view in cross-section, respectively, of a fluid transfer system of the distal anchor delivery device of FIG. 15A.

FIGS. 23-27 illustrate delivery and deployment of a distal anchor using the delivery device of FIG. 15A.

FIG. 28A is a schematic illustration of a side view of a distal anchor delivery device according to another embodiment, shown in a first configuration prior to deployment of a distal anchor through a mitral leaflet of a heart.

FIG. 28B is a schematic illustration of a side view of the distal anchor delivery device of FIG. 28A, shown in a second configuration during deployment of the distal anchor.

FIG. 28C is a schematic illustration of a side view of the distal anchor delivery device of FIG. 28A, shown in a third configuration during deployment of the distal anchor.

FIG. 28D is a schematic illustration of a side view of the distal anchor delivery device of FIG. 28A, shown in a fourth configuration during deployment of the distal anchor.

FIGS. 32A-32E illustrate in sequence the formation of the distal anchor of FIG. 31 about an exterior of a distal end portion of a delivery device, shown in an elongated configuration.

FIGS. 33A-33D illustrate an example procedure for preparing a delivery device to deliver a distal anchor, according to an embodiment.

FIGS. 34A-34H illustrate an example method of forming a distal anchor about an exterior of a needle.

FIG. 40A is a side view of a distal anchor according to another embodiment shown in a delivery configuration; FIG. 40B is a side view of the distal anchor of FIG. 40A shown in a partially deployed configuration; and FIG. 40C is a side view of the distal anchor of FIG. 40A in a deployed configuration.

FIG. 41A is a side view of a distal anchor according to another embodiment, shown in a delivery configuration and disposed within a lumen of a delivery device.

FIG. 41B is illustrates the distal anchor of FIG. 41A in the delivery configuration.

FIGS. 45A and 45B are side views of a distal anchor according to another embodiment, shown in a delivery configuration and a deployed configuration, respectively.

FIG. 45C is a perspective view of the distal anchor of FIGS. 45A and 45B, shown in the deployed configuration.

DETAILED DESCRIPTION

Figure 1:
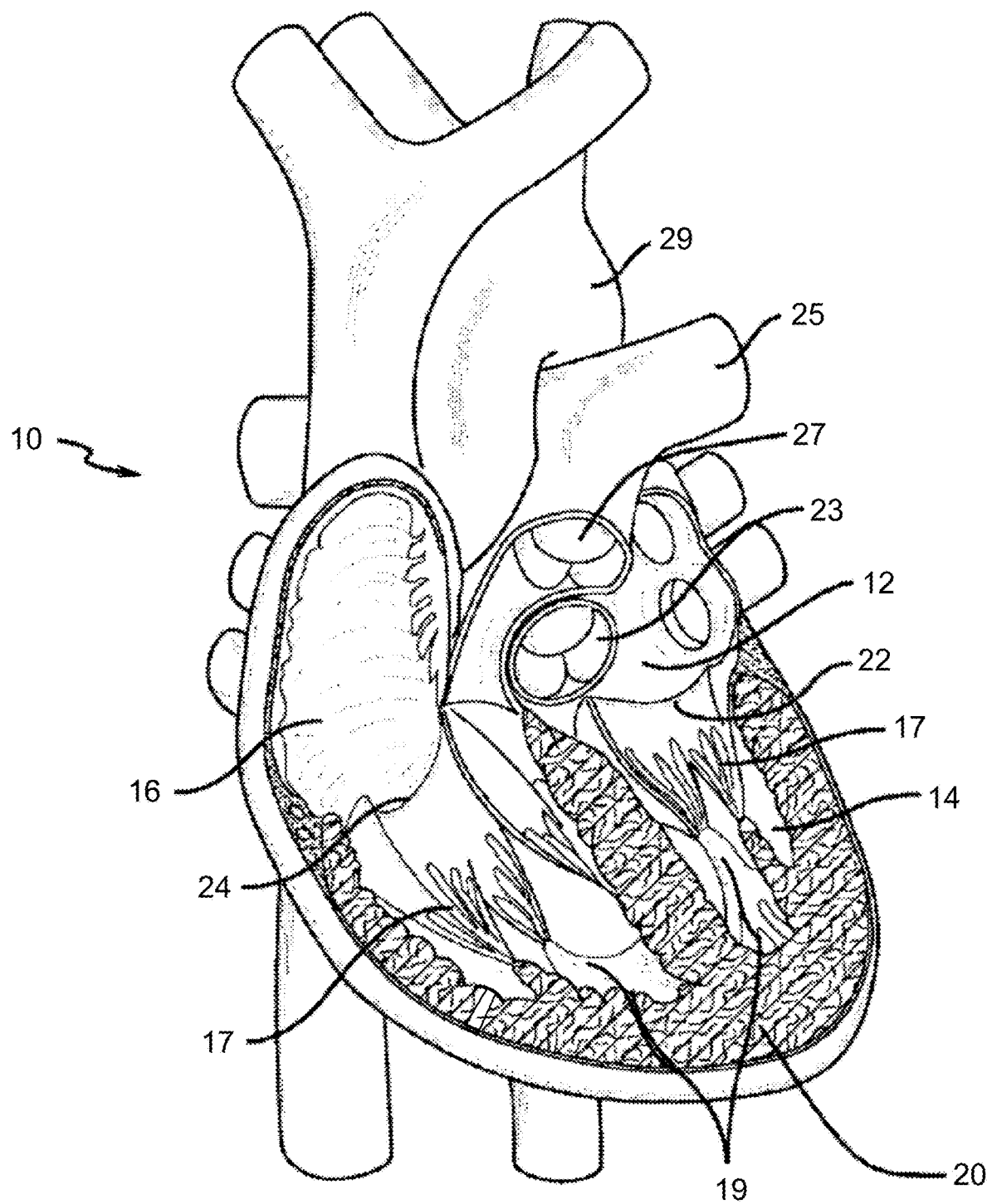
FIG. 1 is a cut-away anterior view of a heart, showing the internal chambers, valves and adjacent structures.

The headings provided herein, if any, are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Apparatus and methods for performing a non-invasive procedure to repair a cardiac valve, such as a mitral valve or tricuspid valve, are described herein. In some embodiments, a method for repairing a mitral valve includes inserting a delivery device through an apex region of a heart and extending a distal end of the delivery device to the proximal side of a leaflet of the mitral valve. A piercing portion of the delivery device can be used to form an opening in the leaflet, through which the distal end of the delivery device can be inserted. The delivery device can be used to form or deliver a distal anchor to the distal side of the leaflet. The location of the opening in the leaflet and the placement of the distal anchor can be anywhere in the leaflet from the free edge up to the base of the mitral valve leaflet and even in the mitral-annular curtain or annulus of the valve. The delivery device can then be withdrawn and a tether coupled to the distal anchor can be secured to an outer surface of the heart at the apex region with, for example, a proximal anchor. The combined distal anchor, tether and proximal anchor is also referred to herein as an anchor-tether apparatus. Before the proximal anchor of the anchor-tether apparatus is fixed to the heart, the length of the tether portion can be adjusted so that the distal movement during systole of the prolapsed segment of the prolapsed leaflet to which the tether portion is coupled by the distal anchor is limited by the tether apparatus during systole. Properly adjusting the length of the anchor-tether apparatus while the heart is beating allows the operator to precisely titrate the position of the prolapsed segment of the prolapsed leaflet in real time to prevent the leaflet from extending above the plane of the annulus (prolapsing), but so that the prolapsed segment of the prolapsed leaflet can move distally during systole a sufficient distance to coapt properly with the other leaflet(s). This adjustment can involve shortening or lengthening the tether portion between the distal and proximal anchors of the anchor-tether apparatus. The same procedure can be repeated on the same leaflet to deliver one or more additional anchor-tether apparatuses to the leaflet, and or can be performed on the other leaflet of the mitral valve to deliver one more anchor-tether apparatuses to the other leaflet (or to both of the other leaflets, in the case of a tricuspid valve). In the case of multiple anchor-tether apparatuses, the tether adjustment procedure can be done one at a time or all at once with the goal of maximizing the surface of coaptation between the leaflets, and eliminating MR.

In some embodiments, a delivery device is provided to perform the above repair procedure. Such a delivery device can include, for example a distal end portion that includes a piercing portion and a support portion, an elongate member coupled to the distal end portion, and an actuating handle coupled to a proximal end portion of the elongate member. The piercing portion of the distal end portion of the delivery device can be used to form the opening in the leaflet of the mitral valve. The support portion of the distal end portion can be used to deliver or form the distal anchor. The handle can include a tether control device that can be used to hold the tether extending from the distal anchor and secure the tether to the apex region with the proximal anchor.

In some embodiments, an apparatus includes a handle, an actuator operably coupled to the handle, a pusher device defining a lumen, a puncture member coupled to the actuator and at least partially disposed within the lumen defined by the pusher device, and a distal anchor. The distal anchor is disposed at a distal end portion of an artificial chorda and disposed in a delivery configuration. The artificial chorda has a proximal end portion coupled to the actuator. The proximal end portion of the artificial chorda extends through a lumen defined by the puncture member. The actuator can be actuated to move the puncture member distally a preset distance and to move the pusher device distally to move the distal anchor distal to the distal end of the puncture member and to move the distal anchor from the delivery configuration to a deployed configuration.

In some embodiments, a method includes inserting a distal end portion of a delivery device through an apex region of a heart, through a ventricle of the heart and to a proximal side of a valve leaflet. The delivery device has a distal anchor disposed in a delivery configuration at a distal end portion of the delivery device. A distal end of the delivery device is positioned in contact with the proximal side of the leaflet of the valve. The delivery device is actuated to move the puncture member distally through the leaflet a preset distance outside the distal end of the delivery device and on a distal side of the leaflet. The puncture member forms, creates or otherwise defines an opening in the leaflet as the puncture member is moved through the leaflet. The distal anchor is disposed at a distal end portion of an artificial chorda. The artificial chorda extends through a lumen of the puncture member and has a proximal end portion coupled to the delivery device. The actuating the delivery device includes moving the distal anchor distally relative to the puncture member to move the distal anchor to a deployed configuration.

In some embodiments, an apparatus includes a handle, an actuator operably coupled to the handle, a pusher device defining a lumen, a puncture member coupled to the actuator and at least partially disposed within a lumen defined by the pusher device, and a distal anchor. The distal anchor is disposed at a distal end portion of an artificial chorda and disposed in a delivery configuration. The artificial chorda has a proximal end portion coupled to the handle. The proximal end portion of the artificial chorda extends through a lumen defined by the puncture member. The actuator can be actuated at a first time period to move the puncture member distally a preset distance and to move the pusher device distally such that at least a portion of the distal anchor is moved distally relative to the puncture member and disposed distal to the distal end of the puncture member. The actuator can be actuated at a second time period after the first time period to move the distal anchor from its delivery configuration to a deployed configuration.

In some embodiments, a method includes inserting a distal end portion of a delivery device through an apex region of a heart, through a ventricle of the heart and to a proximal side of a valve leaflet. The delivery device has a distal anchor disposed in a delivery configuration at a distal end portion of the delivery device. A distal end of the delivery device is positioned in contact with the proximal side of the leaflet of the valve. The delivery device is actuated during a first time period to move the puncture member distally through the leaflet a preset distance outside the distal end of the delivery device and on a distal side of the leaflet. The puncture member forms, creates, or otherwise defines an opening in the leaflet as the puncture member is moved through the leaflet. The distal anchor is disposed at a distal end portion of an artificial chorda that extends through a lumen of the puncture member and has a proximal end portion coupled to the actuator. Actuating the delivery device during the first time period moves the distal anchor distally relative to the puncture member, through the opening in the leaflet such that at least a portion of the distal anchor is disposed distal to the distal end of the puncture member. The delivery device is actuated during a second time period after the first time period to move the proximal end portion of the artificial chorda proximally causing the distal anchor to move to a deployed configuration.

As illustrated in FIG. 1, the human heart 10 has four chambers, which include two upper chambers denoted as atria 12, 16 and two lower chambers denoted as ventricles 14, 18. A septum 20 (see, e.g., FIG. 3) divides the heart 10 and separates the left atrium 12 and left ventricle 14 from the right atrium 16 and right ventricle 18. The heart further contains four valves 22, 23, 26, and 27. The valves function to maintain the pressure and unidirectional flow of blood through the body and to prevent blood from leaking back into a chamber from which it has been pumped.

Two valves separate the atria 12, 16 from the ventricles 14, 18, denoted as atrioventricular valves. The mitral valve 22, also known as the left atrioventricular valve, controls the passage of oxygenated blood from the left atrium 12 to the left ventricle 14. A second valve, the aortic valve 23, separates the left ventricle 14 from the aortic artery (aorta) 29, which delivers oxygenated blood via the circulation to the entire body. The aortic valve 23 and mitral valve 22 are part of the "left" heart, which controls the flow of oxygen-rich blood from the lungs to the body. The right atrioventricular valve, the tricuspid valve 24, controls passage of deoxygenated blood into the right ventricle 18. A fourth valve, the pulmonary valve 27, separates the right ventricle 18 from the pulmonary artery 25. The right ventricle 18 pumps deoxygenated blood through the pulmonary artery 25 to the lungs wherein the blood is oxygenated and then delivered to the left atrium 12 via the pulmonary vein. Accordingly, the tricuspid valve 24 and pulmonic valve 27 are part of the "right" heart, which control the flow of oxygen-depleted blood from the body to the lungs.

Both the left and right ventricles 14, 18 constitute "pumping" chambers. The aortic valve 23 and pulmonic valve 27 lie between a pumping chamber (ventricle) and a major artery and control the flow of blood out of the ventricles and into the circulation. The aortic valve 23 and pulmonic valve 27 have three cusps, or leaflets, that open and close and thereby function to prevent blood from leaking back into the ventricles after being ejected into the lungs or aorta 29 for circulation.

Both the left and right atria 12, 16 are "receiving" chambers. The mitral valve 22 and tricuspid valve 24, therefore, lie between a receiving chamber (atrium) and a ventricle so as to control the flow of blood from the atria to the ventricles and prevent blood from leaking back into the atrium during ejection from the ventricle. Both the mitral valve 22 and tricuspid valve 24 include two or more cusps, or leaflets (not shown in FIG. 1), that are encircled by a variably dense fibrous ring of tissues known as the annulus (not shown in FIG. 1). The valves are anchored to the walls of the ventricles by chordae tendineae (chordae; singular "chorda") 17. The chordae tendineae 17 are cord-like tendons that connect the papillary muscles 19 to the leaflets (not shown in FIG. 1) of the mitral valve 22 and tricuspid valve 24 of the heart 10. The papillary muscles 19 are located at the base of the chordae 17 and are within the walls of the ventricles. The papillary muscles 19 do not open or close the valves of the heart, which close passively in response to pressure gradients; rather, the papillary muscles 19 brace the valves against the high pressure needed to circulate the blood throughout the body. Together, the papillary muscles 19 and the chordae tendineae 17 are known as the subvalvular apparatus. The function of the subvalvular apparatus is to keep the valves from prolapsing into the atria when they close.

Figure 2A:
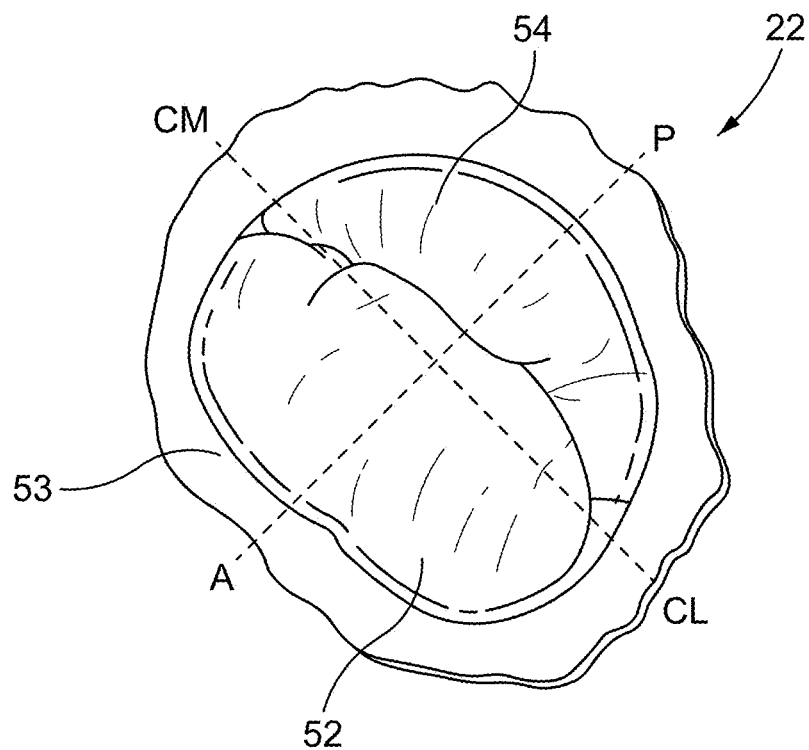
FIG. 2A is a top perspective view of a healthy mitral valve with the mitral leaflets closed.

The mitral valve 22 is illustrated in FIG. 2A. The mitral valve 22 includes two leaflets, the anterior leaflet 52 and the posterior leaflet 54, and a diaphanous incomplete ring around the valve, called the annulus 53. The mitral valve 22 has two papillary muscles 19, the anteromedial and the posterolateral papillary muscles (see, e.g., FIG. 1), which attach the leaflets 52, 54 to the walls of the left ventricle 14 via the chordae tendineae 17 (see, e.g., FIG. 1).

Figure 2B:
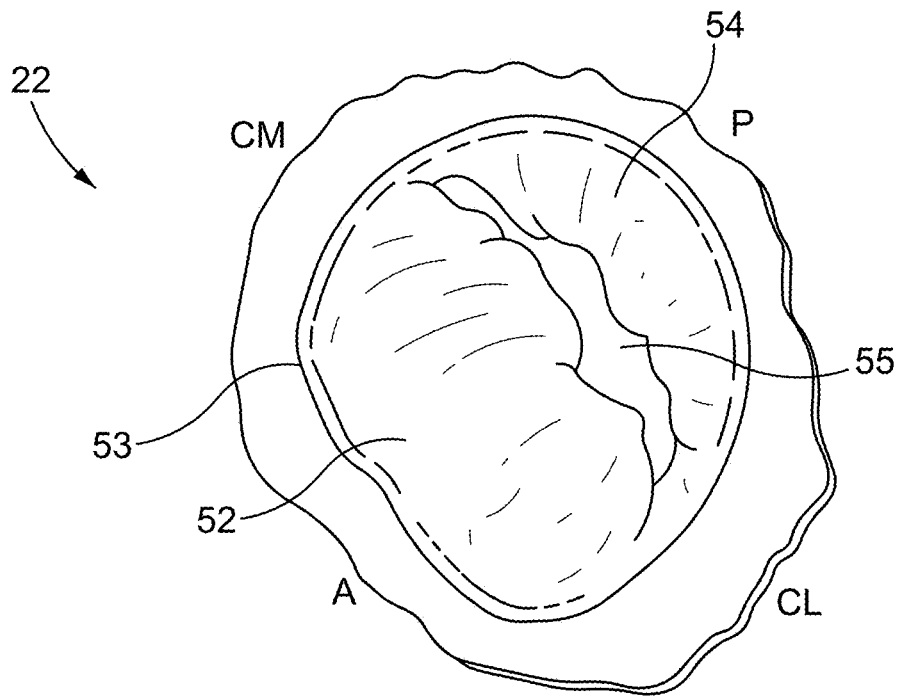
FIG. 2B is a top perspective view of a dysfunctional mitral valve with a visible gap between the mitral leaflets.
Figure 2C:
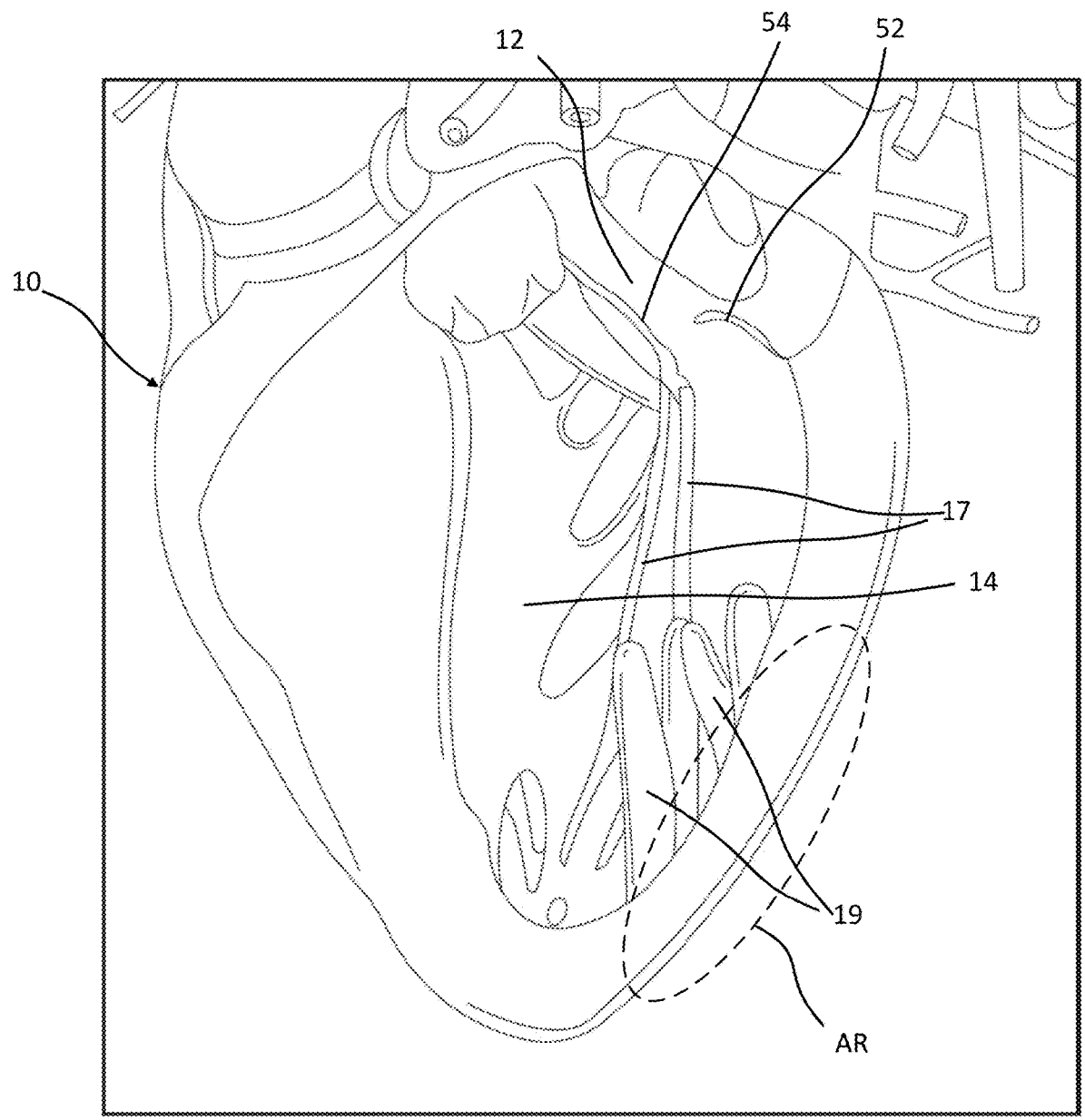
FIG. 2C is a cross-sectional view of a heart illustrating a mitral valve prolapsed into the left atrium.
Figure 2D:
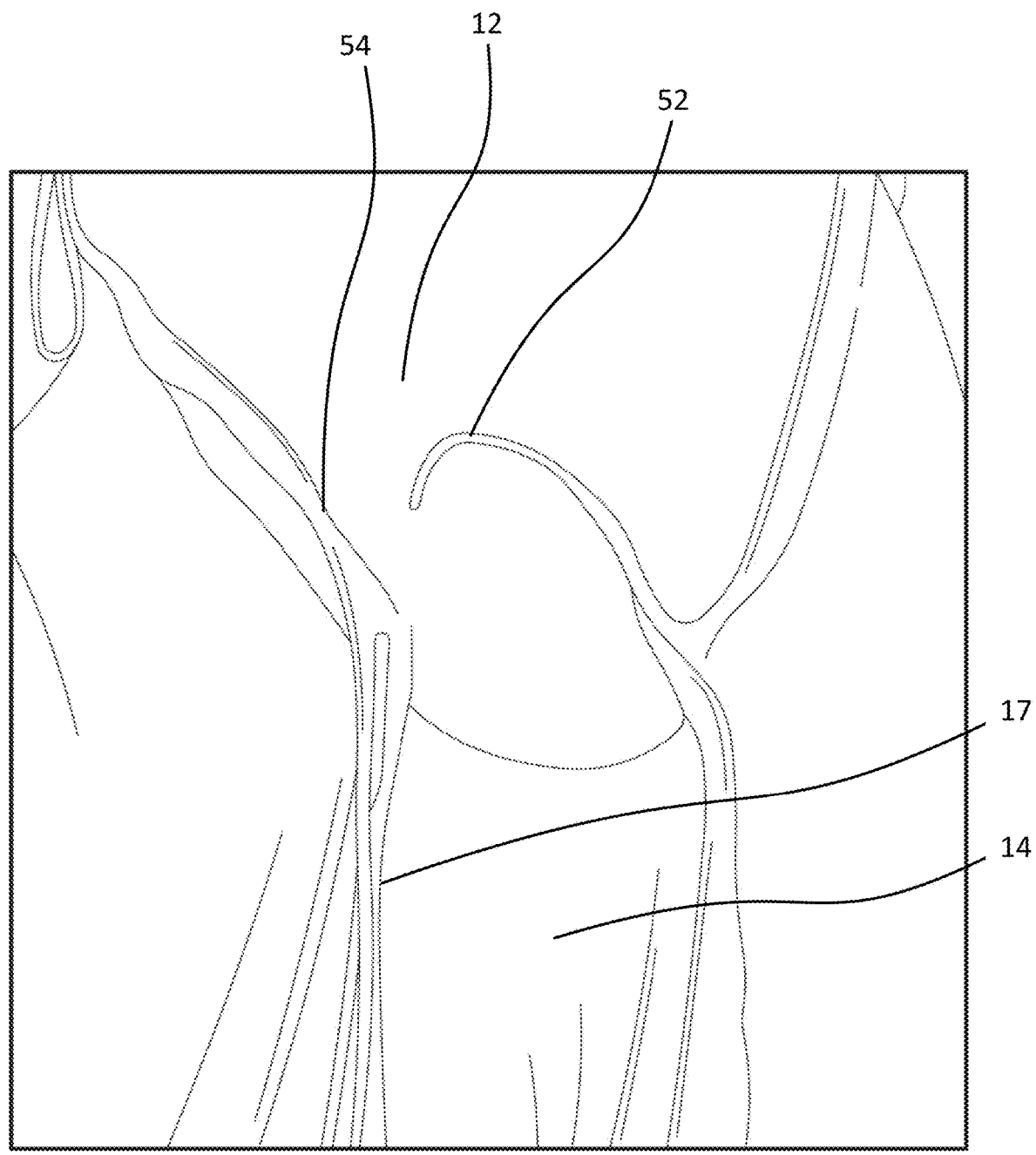
FIG. 2D is an enlarged view of the prolapsed mitral valve of FIG. 2C.

FIG. 2B illustrates a prolapsed mitral valve 22. As can be seen with reference to FIG. 2B-2D, prolapse occurs when a prolapsed segment of a leaflet 52, 54 of the mitral valve 22 is displaced above the plane of the mitral annulus into the left atrium 12 (see FIGS. 2C and 2D) preventing the leaflets from properly sealing together to form the natural plane or line of coaptation between the valve leaflets during systole. Because one or more of the leaflets 52, 54 malfunction, the mitral valve 22 does not close properly, and, therefore, the leaflets 52, 54 fail to coapt. This failure to coapt causes a gap 55 between the leaflets 52, 54 that allows blood to flow back into the left atrium, during systole, while it is being ejected by the left ventricle. As set forth above, there are several different ways a leaflet may malfunction, which can thereby lead to regurgitation.

Mitral valve regurgitation increases the workload on the heart and may lead to very serious conditions if left untreated, such as decreased ventricular function, pulmonary hypertension, congestive heart failure, permanent heart damage, cardiac arrest, and ultimately death. Since the left heart is primarily responsible for circulating the flow of blood throughout the body, malfunction of the mitral valve 22 is particularly problematic and often life threatening.

As described in detail in PCT International Application No. PCT/US2012/043761 (published as WO 2013/003228 A1) (referred to herein as "the '761 PCT Application"), the entire disclosure of which is incorporated herein by reference, methods and devices are provided for performing non-invasive procedures to repair a cardiac valve, such as a mitral valve. Such procedures include procedures to repair regurgitation that occurs when the leaflets of the mitral valve do not coapt at peak contraction pressures, resulting in an undesired back flow of blood from the ventricle into the atrium. As described in the '761 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

In one example method, the heart may be accessed through one or more openings made by a small incision(s) in a portion of the body proximal to the thoracic cavity, for example, between one or more of the ribs of the rib cage of a patient, proximate to the xyphoid appendage, or via the abdomen and diaphragm. Access to the thoracic cavity may be sought so as to allow the insertion and use of one or more thorascopic instruments, while access to the abdomen may be sought so as to allow the insertion and use of one or more laparoscopic instruments. Insertion of one or more visualizing instruments may then be followed by transdiaphragmatic access to the heart. Additionally, access to the heart may be gained by direct puncture (i.e., via an appropriately sized needle, for instance an 18-gauge needle) of the heart from the xyphoid region. Accordingly, the one or more incisions should be made in such a manner as to provide an appropriate surgical field and access site to the heart. Access may also be achieved using percutaneous methods. See for instance, "Full-Spectrum Cardiac Surgery Through a Minimal Incision Mini-Sternotomy (Lower Half) Technique," Doty et al. *Annals of Thoracic Surgery* 1998; 65(2): 573-7 and "Transxiphoid Approach Without Median Sternotomy for the Repair of Atrial Septal Defects," Barbero-Marcial et al. *Annals of Thoracic Surgery* 1998; 65(3): 771-4, which are incorporated in their entirety herein by reference.

After prepping and placing the subject under anesthesia, a transesophageal echocardiogram (TEE) (2D or 3D), a transthoracic echocardiogram (TTE), intracardiac echo (ICE), or cardio-optic direct visualization (e.g., via infrared vision from the tip of a 7.5 F catheter) may be performed to assess the heart and its valves.

After a minimally invasive approach is determined to be advisable, one or more incisions are made proximate to the thoracic cavity so as to provide a surgical field of access. The total number and length of the incisions to be made depend on the number and types of the instruments to be used as well as the procedure(s) to be performed. The incision(s) should be made in such a manner so as to be minimally invasive. As referred to herein, the term "minimally invasive" means in a manner by which an interior organ or tissue may be accessed with as little as possible damage being done to the anatomical structure through which entry is sought. Typically, a minimally invasive procedure is one that involves accessing a body cavity by a small incision of, for example, approximately 5 cm or less made in the skin of the body. The incision may be vertical, horizontal, or slightly curved. If the incision is placed along one or more ribs, it should follow the outline of the rib. The opening should extend deep enough to allow access to the thoracic cavity between the ribs or under the sternum and is preferably set close to the rib cage and/or diaphragm, dependent on the entry point chosen.

One or more other incisions may be made proximate to the thoracic cavity to accommodate insertion of a surgical scope so as to allow ready access to and visualization of the heart. The surgical scope may be any type of endoscope, but is typically a thorascope or laparoscope, dependent upon the type of access and scope to be used. At this point, the practitioner can confirm that access of one or more cardiac valves through the apex region of the heart is appropriate for the particular procedure to be performed.

Once a suitable entry point has been established, the surgeon can use one or more sutures to make a series of stitches in one or more concentric circles in the myocardium at the desired location to create a "pursestring" closure. The Seldinger technique can be used to access the left ventricle in the area surrounded by the pursestring suture by puncturing the myocardium with a small sharp hollow needle (a "trocar") with a guidewire in the lumen of the trocar. Once the ventricle has been accessed, the guidewire can be advanced, and the trocar removed. A valved-introducer with dilator extending through the lumen of the valved-introducer can be advanced over the guidewire to gain access to the left ventricle. The guidewire and dilator can be removed and the valved-introducer will maintain hemostasis, with or without a suitable delivery device inserted therein, throughout the procedure. Alternatively, the surgeon can make a small incision in the myocardium and insert the valved-introducer into the heart via the incision. Once the valved-introducer is properly placed the pursestring suture is tightened to reduce bleeding around the shaft of the valved-introducer.

A suitable device such as a delivery device described herein, may be advanced into the body and through the valved-introducer in a manner so as to access the left ventricle. The advancement of the device may be performed in conjunction with sonography or direct visualization (e.g., direct transblood visualization). For example, the delivery device may be advanced in conjunction with TEE guidance or ICE so as to facilitate and direct the movement and proper positioning of the device for contacting the appropriate apical region of the heart. Typical procedures for use of echo guidance are set forth in Suematsu, Y., J. Thorac. Cardiouasc. Surg. 2005; 130:1348-1356, herein incorporated by reference in its entirety.

Figure 3:
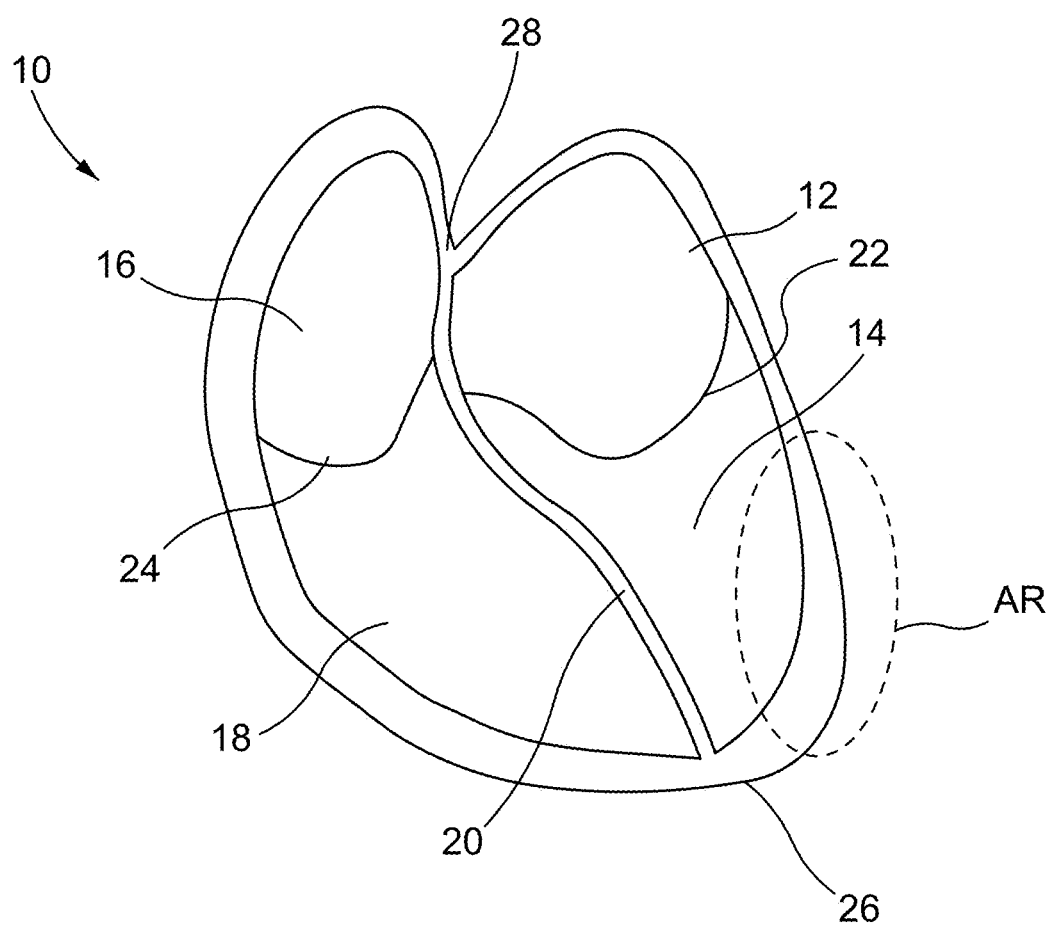
FIG. 3 is a cross-sectional view of a heart showing the left atrium, right atrium, left ventricle, right ventricle and the apex region.

As shown in FIG. 3, one or more chambers, i.e., the left atrium 12, left ventricle 14, right atrium 16, or right ventricle 18 in the heart 10 may be accessed in accordance with the methods disclosed herein. Access into a chamber 12, 14, 16, 18 in the heart 10 may be made at any suitable site of entry but is preferably made in the apex region of the heart, for example, slightly above the apex 26 at the level of the papillary muscles 19 (see also FIG. 2C). Typically, access into the left ventricle 14, for instance, to perform a mitral valve repair, is gained through the process described above performed in the apical region, close to (or slightly skewed toward the left of) the median axis 28 of the heart 10. Typically, access into the right ventricle 18, for instance, to perform a tricuspid valve repair, is gained through the process described above performed in the apical region, close to or slightly skewed toward the right of the median axis 28 of the heart 10. Generally, an apex region of the heart is a bottom region of the heart that is within the left or right ventricular region and is below the mitral valve 22 and tricuspid valve 24 and toward the tip or apex 26 of the heart 10. More specifically, an "apex region" AR of the heart (see FIGS. 2C and 3) is within a few centimeters to the right or to the left of the septum 20 of the heart 10 at or near the level of the papillary muscles 19. Accordingly, the ventricle can be accessed directly via the apex 26, or via an off apex location that is in the apical or apex region AR, but slightly removed from the apex 26, such as via a lateral ventricular wall, a region between the apex 26 and the base of a papillary muscle 19, or even directly at the base of a papillary muscle 19 or above. Typically, the incision made to access the appropriate ventricle of the heart is no longer than about, for example, 0.5 cm. Alternatively, access can be obtained using the Seldinger technique described above.

The mitral valve 22 and tricuspid valve 24 can be divided into three parts—an annulus (see 53 in FIGS. 2A and 2B), leaflets (see 52, 54 in FIGS. 2A and 2B), and a sub-valvular apparatus. The sub-valvular apparatus includes the papillary muscles 19 (see FIG. 1) and the chordae tendineae 17 (see FIG. 1), which can elongate and or rupture. If the valve is functioning properly, when closed, the free margins or edges of the leaflets come together and form a tight junction, the arc of which, in the mitral valve, is known as the line, plane or area of coaptation (see, e.g., encircled area labeled AC in FIG. 27). Normal mitral and tricuspid valves open when the ventricles relax allowing blood from the atrium to fill the decompressed ventricle. When the ventricle contracts, chordae tendineae properly position the valve leaflets such that the increase in pressure within the ventricle causes the valve to close, thereby preventing blood from leaking into the atrium and assuring that all of the blood leaving the ventricle is ejected through the aortic valve (not shown) and pulmonic valve (not shown) into the arteries of the body. Accordingly, proper function of the valves depends on a complex interplay between the annulus, leaflets, and subvalvular apparatus. Lesions in any of these components can cause the valve to dysfunction and thereby lead to valve regurgitation. As set forth above, regurgitation occurs when the leaflets do not coapt properly at peak contraction pressures. As a result, an undesired back flow of blood from the ventricle into the atrium occurs.

Although the procedures described herein are with reference to repairing a cardiac mitral valve or tricuspid valve by the implantation of one or more artificial chordae, the methods presented are readily adaptable for various types of leaflet and annular repair procedures. In general, the methods herein will be described with reference to a mitral valve 22.

Some embodiments described herein refer to a deliver device that includes a needle as a puncture member configured to pierce a cardiac tissue such as a mitral valve leaflet. It should be understood that although such embodiments are described with reference to a needle, in alternative embodiments, a deliver device can include any puncture member suitable to pierce a cardiac tissue and form an opening therethrough. For example, in some embodiments, a puncture member can be a trocar, guidewire, rod, tube, or the like. As a further example, in some embodiments, a puncture member can include an electrosurgical device, i.e., a device with an electrical circuit (or any suitable electrical energy source) operating at a frequency (e.g., a high frequency) configured to cut and/or pierce cardiac tissue.

Some embodiments described herein refer to a delivery device that includes a plunger as an actuator configured to receive a manual force and move within a handle of the delivery device to help deliver and deploy a distal anchor within a heart. For example, in some embodiments, such a delivery device having a manual plunger actuator can be used to deploy a bulky-knot type distal anchor as described herein. It should be understood that although such embodiments are described with reference to a manually actuated plunger, in alternative embodiments, a delivery device can include any suitable actuator, such as, for example, an automatically actuated plunger, and/or a button that when pressed or otherwise activated can actuate an internal mechanism suitable to selectively move components (e.g., a pusher, a puncture member, a suture, etc.) of the delivery device. As a further example, an actuator of a delivery device can include one or more energy storage members configured to selectively move components of the delivery device.

In some embodiments, a method includes the implantation of one or more artificial chordae tendineae into one or more leaflets (e.g., 52, 54 in FIGS. 2A and 2B) of a malfunctioning mitral valve 22 and/or tricuspid valve 24. After an appropriate incision has been made in the apex region of the heart, for example, in the apex 26, a delivery device can be introduced into, for example, the left ventricle 14 of the heart and advanced in such a manner so as to contact one or more cardiac tissues (for instance, a leaflet, an annulus, a cord, a papillary muscle, or the like) that are in need of repair. Sonic guidance, for instance, TEE guidance or ICE, may be used to assist in the advancement of the device into the ventricle, the proper positioning of the distal tip of the device on the proximal side of the leaflet and, if necessary, the grasping of the cardiac tissue with the device. Direct trans-blood visualization may also be used.

Figure 4:
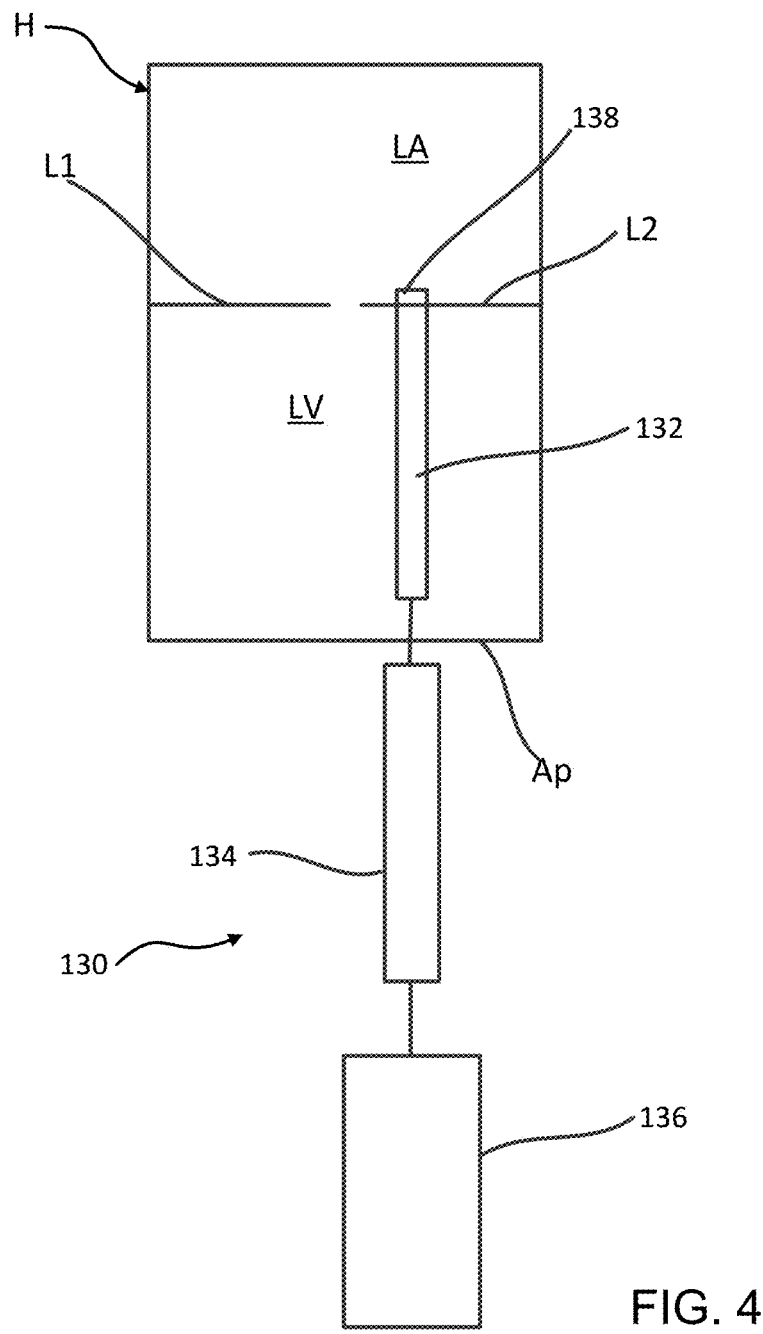
FIG. 4 is a schematic illustration of a delivery device, according to an embodiment, shown inserted into a portion of a heart.

FIG. 4 is a schematic illustration of a portion of a heart with a delivery device inserted therein, according to an embodiment. The delivery device 130 can include a distal end portion 132 configured to be inserted into a heart H, an elongate portion 134 coupled to the distal end portion 132, and a proximal end portion 136. The distal end portion 132 of the delivery device 130 can include a puncture or piercing member (not shown) and an anchor support portion (not shown). The distal end portion 132 can include other features to enable the delivery device 130 to perform various functions, such as, for example, grasping, suctioning, irrigating, cutting, suturing, or otherwise engaging a cardiac tissue.

The proximal end portion 136 can include, for example, a handle that can be used by the user/operator to manipulate movement of the delivery device 130 and/or to actuate the delivery device 130. The proximal end portion 136 can also include control features and/or components that can be used to actuate various functions of the delivery device 130. The proximal end portion 136 can also include a holding device or member that can be used to hold and control a tether (e.g., suture, cord or wire) extending from a distal anchor (described in more detail below) during deployment of the distal anchor.

Figure 5:
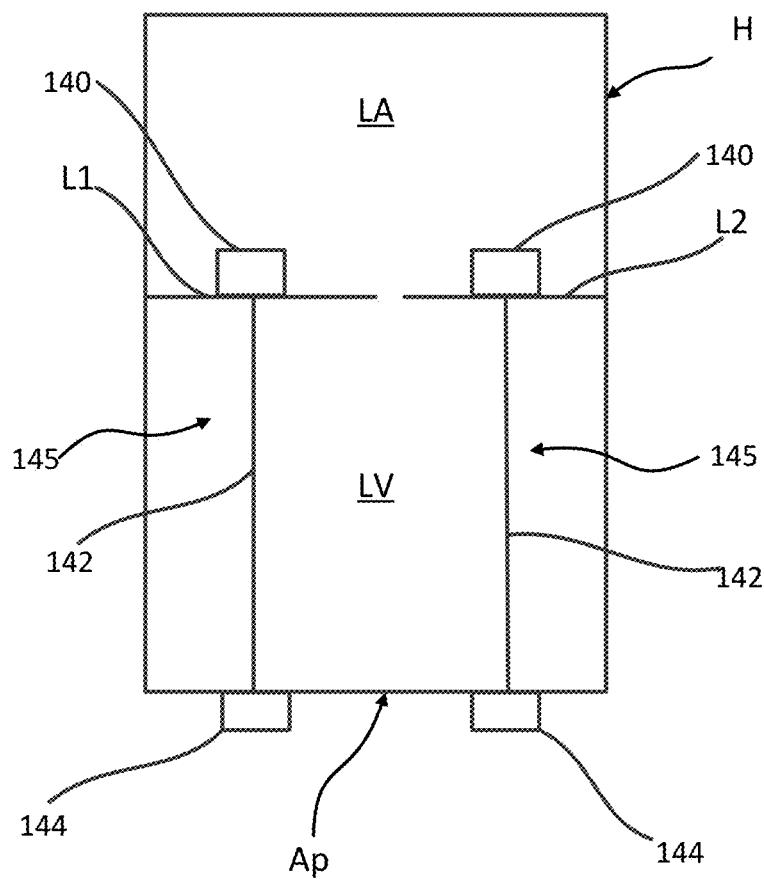
FIG. 5 is a schematic illustration of two anchor-tether apparatus shown implanted within a heart, according to an embodiment.

Using, for example, ultrasound guidance (real-time transesophageal echocardiography), the delivery device 130 can be inserted through an access port at the apex Ap (or near the apex) of the heart H and guided through the left ventricle LV and into contact with a proximal side of a mitral valve leaflet L1 (or L2), shown in FIGS. 4 and 5, at a location where the user/operator has determined that a repair is needed. Typically, this would be a prolapsed segment of the body of the anterior or posterior leaflet, i.e. in a location where the valve has prolapsed as a result of a broken or elongated chorda. The distal end portion 130 of the delivery device 130 can be used to puncture or form an opening in the valve leaflet L1 and/or the valve leaflet L2. For example, as shown in FIG. 4, the piercing member at a distal tip 138 can be used to puncture or pierce through the leaflet L2. This can be done with or without grasping, capturing, or otherwise immobilizing the prolapsed segment of the leaflet.

The distal tip 138 of the delivery device 130 can be inserted through the puncture site or opening and positioned on a distal side of the leaflet L2 and within the left atrium LA. When the distal tip 138 is in the desired position, the delivery device 130 can be actuated to insert a distal anchor 140 or form a distal anchor 140 (see, FIG. 5) on the distal side of the leaflet L2 within the left atrium LA of the heart H. In some embodiments, the distal anchor 140 can include a suture or a suture/guide wire combination that can form into a knot upon actuation of the delivery device 130. For example, in some embodiments, the distal anchor 140 includes a large or bulky knot made of ePTFE suture or other appropriate material that is formed by the delivery device 130 and that attains a significant size in the left atrium LA, above the leaflet L2. The knot can be in the form of one or more multi-turn coils of the suture or other material used to form the tether (described in more detail below), which coils can be changed from an elongated configuration to a knot configuration by approximating opposite ends of the coil(s) towards each other to form one or more loops. In some embodiments, the distal anchor 140 includes an anchor member that is deployed into the left atrium LA above the leaflet L2 upon actuation of the delivery device 130.

The distal anchor 140, whether formed by the delivery device 130 or deployed by the delivery device 130 can be coupled to a tether 142 extending proximally from the distal anchor 140 and secured to the proximal end portion 136 of the delivery device 130. Alternatively, the distal anchor 140 and the tether 142 can be all one component (i.e., ePTFE suture) where the distal anchor 140 is formed by altering the shape of the tether 142 from a first position to a second position. As described above, the proximal end portion 136 of the delivery device 130 can include a holding device (not shown) that can be used to secure and control the tether 142 during delivery and deployment of the distal anchor 140.

As shown in FIG. 5, after the distal anchor 140 has been deployed or formed, the delivery device 130 can be withdrawn from the heart H. The length of the tether 142 between the distal anchor 140 and the opening in the heart can be adjusted, as discussed above, until the desired length is established (i.e. prolapse of the leaflet is prevented, but the leaflet can still move distally sufficient to coapt with the other leaflet(s)). The proximal end of the tether 142 can then be secured to an outer surface of the heart H at, for example, the apex Ap region, with a proximal anchor 144. The proximal anchor 144 can be, for example, a pledget, one or more knots, or other suitable anchoring device.

The above procedure can be performed multiple times on the same leaflet, and/or can be performed on the other mitral valve leaflet L1 in the same manner. The result can thus be that two or more anchor-tether apparatuses 145 are each anchored on a distal side of a leaflet L1, L2 with a distal anchor 140 and secured to the apex Ap region of the heart H with a proximal anchor 144 via the tether 142. Thus, each anchor-tether apparatus 145 can secure the top of the leaflet L1, L2 to the apex Ap region of the heart H, functioning as an artificial chorda or neochord.

Figure 6:
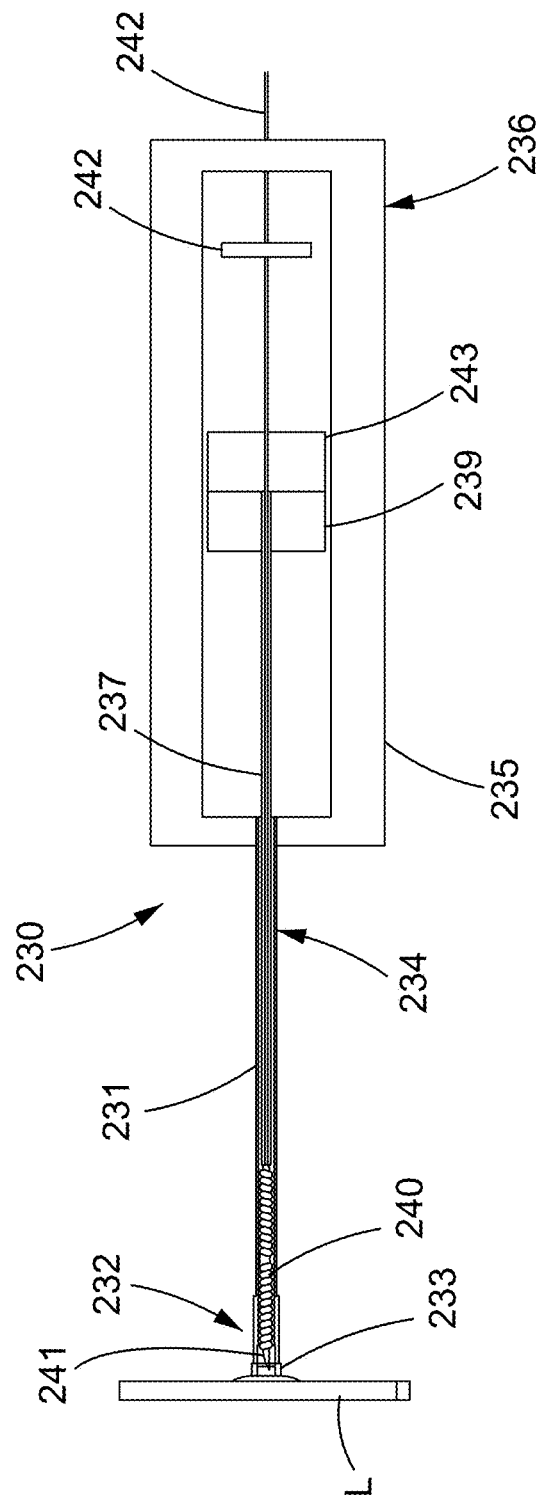
FIG. 6 is a schematic illustration of a distal anchor delivery device, according to an embodiment, shown in a first configuration prior to deployment of a distal anchor through a mitral leaflet of a heart and showing the lumen of the outer tube and the lumen of the pusher device.
Figure 12:
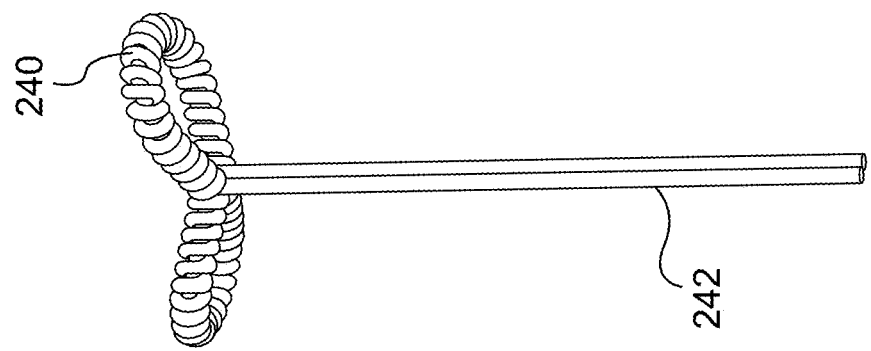
FIG. 12 is a side view of the distal anchor of FIG. 6, shown in a coiled knot configuration.

FIGS. 6-10 show a schematic illustration of an embodiment of a distal anchor that can be deployed on a distal side of a mitral valve leaflet, and a delivery device for deploying such a distal anchor within the heart of a patient. In this embodiment, a distal anchor 240 (see, e.g., FIGS. 9 and 10) includes a pre-formed knot that can be formed/deployed using a delivery device 230. As shown in FIG. 6, the delivery device 230 includes a distal portion 232, a medial portion 234, and a proximal end portion 236. Disposed on the distal end portion 232 is a distal end effector 233 that is coupled to a distal end portion of an elongate outer tube 231 and can be placed in contact with a proximal side of a mitral valve leaflet L during deployment of the distal anchor 240. The distal end effector 233 can distribute the force of the elongate outer tube 231 over a larger area to prevent/ eliminate puncturing of the leaflet with the delivery device 230 during deployment. In some embodiments, the end effector 233 can include a balloon. A proximal end portion of the outer tube 231 is coupled to a handle 235 at the proximal end portion 236. Coupled to or included at least partially within the handle 235 are an elongate pusher 237 coupled to a pusher hub 239, a puncture member 241 (e.g., a needle) coupled to a puncture member hub 243 (e.g., a needle hub), and a suture catch 246. The pusher 237 is movably disposed within a lumen of the outer tube 231 and the needle 241 is movably disposed within a lumen of the pusher 237. The needle 241 includes at a distal end a piercing member or portion 247 as shown in FIG. 7. In some embodiments, the elongate outer tube 231 can provide a relatively stiff structure and can protect the puncture member 241 and/or the pusher 237 during delivery and deployment of the distal anchor, and during withdrawal of the delivery device from within the patient. In other embodiments, the delivery device does not include an elongate outer tube or distal end effector. In such embodiments, in some instances, a separate device can be used to provide functionality similar to the functionality provided by the elongate outer tube 231 and the distal end effector 233 described above.

Figure 11:
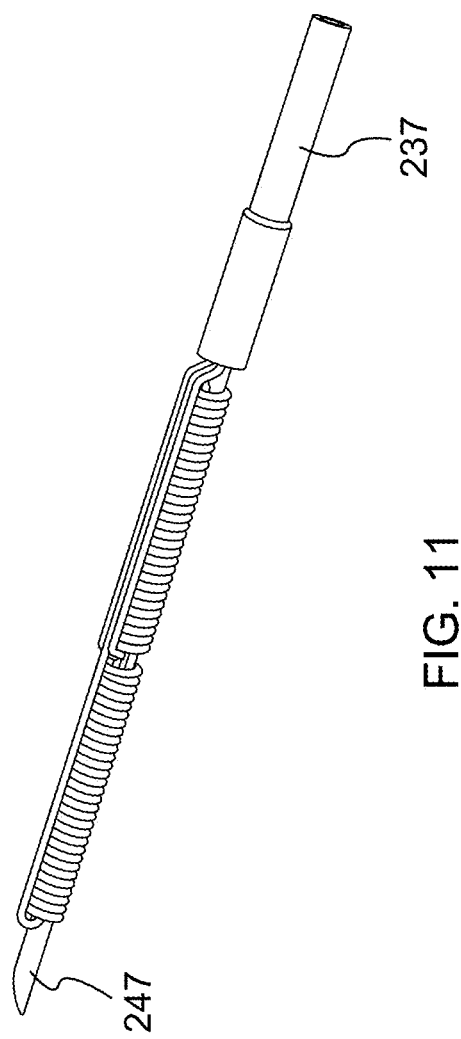
FIG. 11 is a perspective view of the distal anchor of FIG. 6 shown in an elongated coiled configuration and disposed about the needle of the delivery device.

A suture 242 (also referred to herein as "tether") is coupled to the suture catch 246 and extends through a lumen of the needle 241 and is formed into a coiled configuration at the distal end portion 232 of the delivery device 230 as shown in FIG. 6. The suture catch 246 can be configured to releasably hold or secure the suture 242 during delivery of the distal anchor 240 as describe in more detail below. In some embodiments, the suture catch 246 can hold the suture 242 with a friction fit or with a clamping force and can have a lock that can be released after the distal anchor 240 has been deployed/formed. The distal coiled portion of the suture 242 will be formed into the distal anchor 240 upon actuation of the delivery device 230 as described in more detail below. As discussed above for distal anchor 140, the distal anchor 240 (e.g., bulky knot) can be in the form of one or more multi-turn coils of the suture 242 that can be changed from an elongated configuration during delivery (see, e.g., FIGS. 7, 11, and 13A) to a knot configuration (see, e.g., FIGS. 9, 10, 12 and 13C) by approximating opposite ends of the coil(s) towards each other, to form one or more loops. For example, two strands or lengths of the suture 242 extend from opposite ends of the elongate coiled portion of the suture 242 and extend through the delivery device 230. When the two proximal ends of the suture 242 are pulled proximally, the opposite ends of the coiled portions are pulled towards each other to form the loops.

Figure 13C:
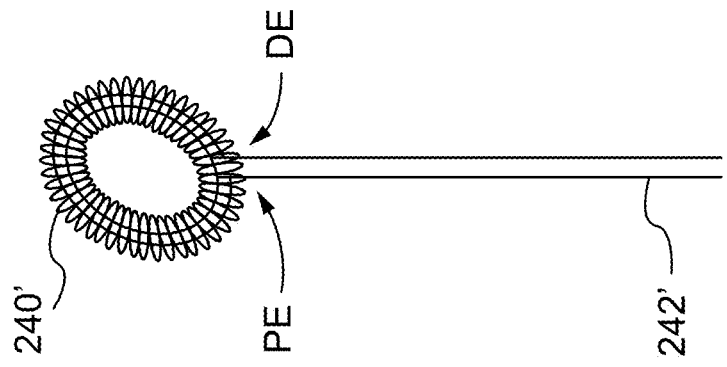
FIG. 13C is a side view of the single coil/loop variation of the distal anchor of FIG. 13A in a coiled knot configuration.
Figure 13B:
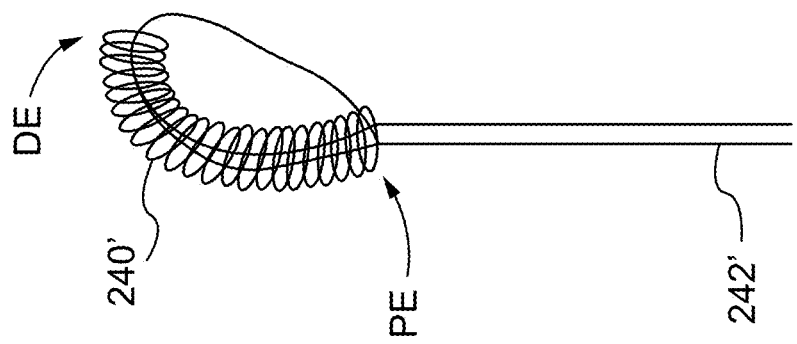
FIG. 13B is a side view of the single coil/loop variation of the distal anchor of FIG. 13A in a partially coiled knot configuration.
Figure 13A:
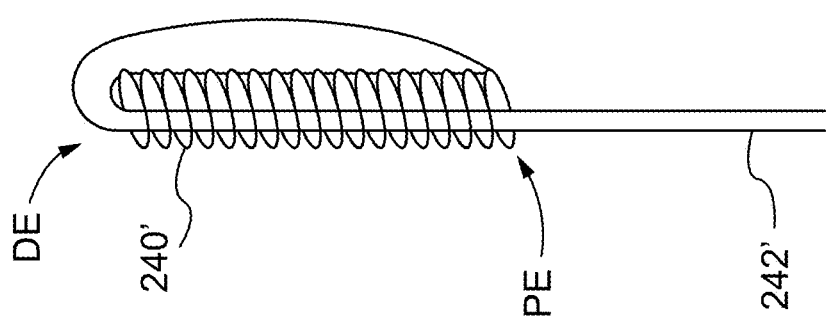
FIG. 13A is a side view of a single coil/loop variation of the distal anchor of FIG. 6 shown in an elongated coiled configuration.

FIGS. 13A-13C illustrate the sequence described above with respect to the distal anchor 140 and the distal anchor 240 transitioning from an elongated configuration to a knot configuration, however for ease of illustration, a single coil and loop variation is shown and described. As shown in FIG. 13A, the distal anchor 240' is in a coiled, elongated formation (e.g., a preformed knot) configured for delivery to a heart. To form the knot configuration (as shown in FIG. 13C), a proximal end of the suture 242' is pulled proximally to deflect the distal end DE of the coil laterally with respect to the proximal end PE of the coil and to draw the proximal end PE of the coil and the distal end DE of the coil towards each other to form a loop L, as illustrated in FIGS. 13B and 13C.

To deliver and form the distal anchor 240 within, for example, a left atrium of the heart to repair a mitral valve, the distal end portion of the needle 241 of the delivery device 230 can be inserted through an apex portion of the heart and into the left ventricle until the end effector 233 contacts a proximal side of the mitral valve leaflet L as shown in FIGS. 6-9. With the delivery device 230 positioned against the mitral leaflet L, and with a proximal end portion of the suture 232 (i.e., the two proximal end portions of the suture 242) secured to the suture catch 246, the needle 241 and needle hub 243, the pusher 237 and pusher hub 239, and the suture catch 246 are all moved distally (in the direction of arrow A) relative to the handle 235 as shown in FIG. 7, until the pusher 237 and pusher hub 239 locks into place relative to the handle 235. As these components are collectively moved distally, the piercing portion 247 of the needle 241 punctures the leaflet L forming an opening, and is passed through the leaflet L and is disposed on the distal side of the leaflet L. In some embodiments, the distal end of piercing portion 247 extends outside of the end effector 233 of the delivery device 230 about 1.0 inch. Simultaneously, the pusher 237 pushes or moves the distal anchor 240 (i.e., the distal coiled portion of the suture 232), still in an elongated configuration and surrounding a portion of the needle 241, through the opening in the leaflet L until it is disposed on the distal side of the leaflet L. As shown in FIG. 7, the piercing portion 247 of the needle 241 extends beyond the distal anchor 240.

As shown in FIG. 8, the needle 241 and needle hub 243 can then be withdrawn or moved proximally in the direction of arrow B until contact is made between the needle hub 243 and the suture catch 246, leaving the distal anchor 240 in the left atrium on the distal side of the leaflet L. As the needle hub 243 (and needle 241) continue to be moved proximally in the direction of arrow B, the distal anchor 240 will begin to form a knot because the suture 242 (e.g., the two end portions of suture 242) is secured to the suture catch 246 such that as the suture catch 246 is moved proximally it pulls the distal anchor 240 approximating opposite ends of the coils towards each other to form one or more loops as show in FIGS. 9 and 10. Further, there is a length of suture 242 between the suture catch 246 and the proximal end of the needle 241 which allows the suture 242 to slide off the needle 241 before the knot is formed. When the needle 241 is withdrawn, the wraps of the suture 242 stay in the same place, eliminating the extra length of suture 242 between the distal end of the needle 241 and the suture catch 246. The knot is thus formed on a distal end of the pusher 237 and not against the mitral valve leaflets. After the distal anchor 240 has formed a knot (as in FIGS. 9 and 10), the proximal end portions of the suture 242 can be released from the suture catch 246 and the delivery device 230 can be withdrawn proximally in the direction of arrow B, leaving the distal anchor 240 disposed on the distal side of the leaflet L, and two lengths of the suture 242 extending out of the heart. In other words, with the suture 242 released from the suture catch 246, the delivery device 230 can be slid over the suture 242 for removal.

As described above for distal anchor 140 and tether 142, the length of the suture 242 between the distal anchor 240 and the opening in the heart can be adjusted, as discussed above, until the desired length is established (i.e. prolapse of the leaflet is prevented, but the leaflet can still move distally sufficient to coapt with the other leaflet(s)). The proximal ends of the suture 242 can then be secured to an outer surface of the heart at, for example, the apex region, with a proximal anchor (not shown). The proximal anchor can be, for example, a pledget, one or more knots, or other suitable anchoring device. As previously described, the above procedure can be performed multiple times on the same leaflet, and/or can be performed on the other mitral valve leaflet in the same manner. The result can thus be that one or more anchor-tether apparatuses (e.g., anchor-tether apparatus 145) as described above are each anchored on a distal side of a leaflet with a distal anchor and secured to the apex of the heart with a proximal anchor via the suture 242. Alternatively, if one or more anchor-tether apparatus are attached to both mitral valve leaflets, an anchor-tether apparatus attached to each leaflet can be secured together in the heart by tying them together with knots or by another suitable attachment member (not shown), creating an edge-to-edge repair to decrease the septal-lateral distance of the mitral valve orifice. The two attached anchor-tether apparatus can be left loose or tensioned to create a "facilitated" edge-toedge repair before being secured to an outer surface of the heart with a proximal anchor.

FIGS. 6-10 illustrate one example method and device for deploying a bulky knot distal anchor. In another embodiment, a bulky knot distal anchor can be deployed/formed using a delivery device that utilizes a short throw deployment sequence configured to insert the distal end portion and piercing member of the needle a shorter distance into the left atrium than as shown and described above for the embodiment of FIGS. 6-10. In such an embodiment, the distal end portion of the needle is used to puncture the leaflet tissue and form an opening in the leaflet tissue, but does not extend as far into the left atrium. In some embodiments, the needle can be extended outside of the distal end of the delivery device (e.g., beyond the end effector) half the distance than what is shown and described for the embodiment of FIGS. 6-10. For example, in some embodiments, the needle can be extended outside the delivery device a distance of about 0.2-0.3 inches (e.g., 0.25 inches). In other embodiments, the needle can be extended outside the delivery device a distance of about 0.15-0.4 inches. Similarly, in some embodiments, a needle can be extended through a proximal side of a heart valve leaflet a distance, for example, of about 0.2-0.3 inches or a distance of about 0.15-0.4 inches from the proximal side of the heart valve leaflet. As yet a further example of the short throw deployment sequence, the needle can be moved a distance sufficient to pierce the proximal side of the leaflet and extend a distance of about 0.05-0.25 inches (e.g., 0.1 inch) from and distal to the distal side of the leaflet. The distal coiled portion of the suture is then moved distally over the needle and into the left atrium using a pusher device. By shortening the distance in which the needle is extended outside of the end effector and into the left atrium, the potential for damage to surrounding tissue can be reduced or eliminated. Further, in some cases, such a short throw deployment sequence can help limit or prevent damage to the needle itself. For example, in some cases, if the needle is extended too far distally outside of the outer tube, the needle may bend unwantedly. FIGS. 14A-14E are schematic illustrations of an embodiment of a delivery device for delivering and deploying a distal anchor and configured to provide such a short throw deployment sequence.

As shown in FIGS. 14A-14E, a delivery device 330 includes a distal end portion 332, a proximal end portion 336 and a medial portion 334. The distal end portion 332 can include an end effector 333 that can be placed in contact with a leaflet L of a mitral valve as described above. The end effector 333 can be coupled to a distal end portion of an outer tube 331 and a proximal end portion of the outer tube 331 is coupled to a handle 335 at the proximal end portion 336. The end effector 333 can distribute the force of the outer tube 331 over a larger area to prevent/eliminate puncturing of the leaflet with the delivery device 330 during deployment. In some embodiments, the end effector 333 can include a balloon. An elongate pusher 337 is movably disposed within a lumen of the outer tube 331 and is coupled to a pusher hub 339 that is movably disposed within the handle 335 and releasably coupled to a plunger (not shown). A needle 341 (see FIGS. 14C and 14D) is movably disposed within a lumen of the pusher 337 and is coupled to a needle hub 243 that is also coupled to the plunger (not shown). The plunger is used to actuate or move the needle 341 and the pusher 337 during deployment of a distal anchor 340 and can be movably disposed at least partially within the handle 335 as described in more detail below for delivery device 430. For example, the handle 335 defines a lumen in which the plunger can be moved. During operation, the pusher 337 also moves within the lumen of the handle 335 as described in more detail below. The delivery device 330 can also include a locking lever (not shown) that can be used to prevent the plunger from moving within the handle 335 during storage and prior to performing a procedure to deploy the distal anchor.

A suture catch 346 (also referred to as "tether catch") is also coupled to the plunger at a proximal end of the delivery device 330. The suture catch 346 can be configured to releasably hold or secure a suture 342 extending through the delivery device 330 during delivery of the distal anchor 340 as described above and as described in more detail below with reference to delivery device 430. In some embodiments, the suture catch 346 can hold the suture 342 with a friction fit or with a clamping force and can have a suture lock that can be released after the distal anchor 340 has been deployed/formed into a bulky knot.

The suture 342 (also referred to herein as "tether") is formed into an elongated coiled configuration and is disposed within the outer tube 331 at the distal end portion 332 of the delivery device 330. As described above for suture 242, two strands of the suture 342 extend from the distal elongated coiled portion of the suture 342, extend through the lumen of the needle 341, through a passageway of the plunger and exit the plunger and needle 341 at a proximal end portion of the plunger. The distal elongated coiled portion of the suture 342 will be formed into the distal anchor 340 (e.g., bulky knot) upon actuation of the delivery device 330 as described in more detail below. As discussed above for distal anchors 140 and 240, the distal anchor 340 can be in the form of one or more multi-turn coils of the suture 342 that can be changed from the elongated coiled configuration during delivery to a knot configuration by approximating opposite ends of the coils towards each other, to form one or more loops.

To deliver and form the distal anchor 340 within, for example, a left atrium of the heart to repair a mitral valve, the distal end portion of 332 of the delivery device 330 can be inserted through an apex portion of the heart and into the left ventricle until the end effector 333 contacts a proximal side of the mitral valve leaflet L as shown in FIG. 14A. In this embodiment, with the delivery device 330 positioned against the mitral leaflet L, and with a proximal end portion of the suture 342 (e.g., two suture strands of suture 342) secured to the suture catch 346, the plunger (not shown) is actuated to move the needle hub 343, the needle 341, the pusher 337 and pusher hub 339, and the coiled portion of the suture 332 (e.g., distal anchor 340) distally until the plunger contacts a stop member (not shown) within the handle 335, which limits the travel of the plunger in the distal direction. As the plunger is actuated, a distal piercing portion 347 of the needle 341 and in some cases, at least the first wrap of the coiled portion of the suture, punctures the leaflet L and forms an opening in the leaflet L (see e.g., FIG. 14B). The distance the distal end portion of the needle 341 extends within the left atrium on the distal side of the leaflet L is determined by the amount of travel allowed by the plunger. Thus, in this embodiment, the delivery device 330 is configured to advance the distal end portion of the needle 341 a shorter distance, for example, between about 0.2-0.3 inches (e.g., 0.25 inches), or less, distally beyond the distal end of the delivery device 330 (e.g., beyond the end effector 333), compared to the embodiment of FIGS. 6-10 in which the needle extends about 1.0 inch. In other embodiments, the needle can be extended outside the delivery device a distance of about 0.15-0.4 inches. When the plunger reaches the stop member, the pusher 337 and pusher hub 339 are released from the plunger 348 and are advanced further distally to a distal position within the handle 335 (see FIG. 14C) where the pusher hub 339 (and pusher 337) can optionally lock into place. Details of how the pusher 337 and pusher hub 339 are moved within the lumen of the handle 335 are described below with respect to delivery device 430.

As the pusher 337 is moved distally, a distal end of the pusher 337 moves or pushes the distal coiled portion of the suture 342 (i.e., distal anchor 340) over the distal end of the needle 341 and further within the left atrium of the heart on a distal side of the mitral leaflet (see FIG. 14C). In other words, the distal end of the pusher 337 and the distal coiled portion of the suture 342 extends beyond the distal end of the needle 341. For example, in some embodiments, at least half a length of the distal coiled portion of the suture 342 extends beyond the distal end of the needle 341. In some embodiments, at least three quarters of the length of the distal coiled portion of the suture 342 extends beyond the distal end of the needle 341. In other embodiments, the entire length of the distal coiled portion of the suture 342 extends beyond the distal end of the needle 341. To allow the distal coiled portion of the suture 342 (i.e., distal anchor 340) to slide relative to the plunger, when the suture 342 is loaded within the delivery device 330, there is slack in the suture 342 between the distal coiled portion of the suture 342 and the suture lock within the suture catch 346.

Figure 14E:
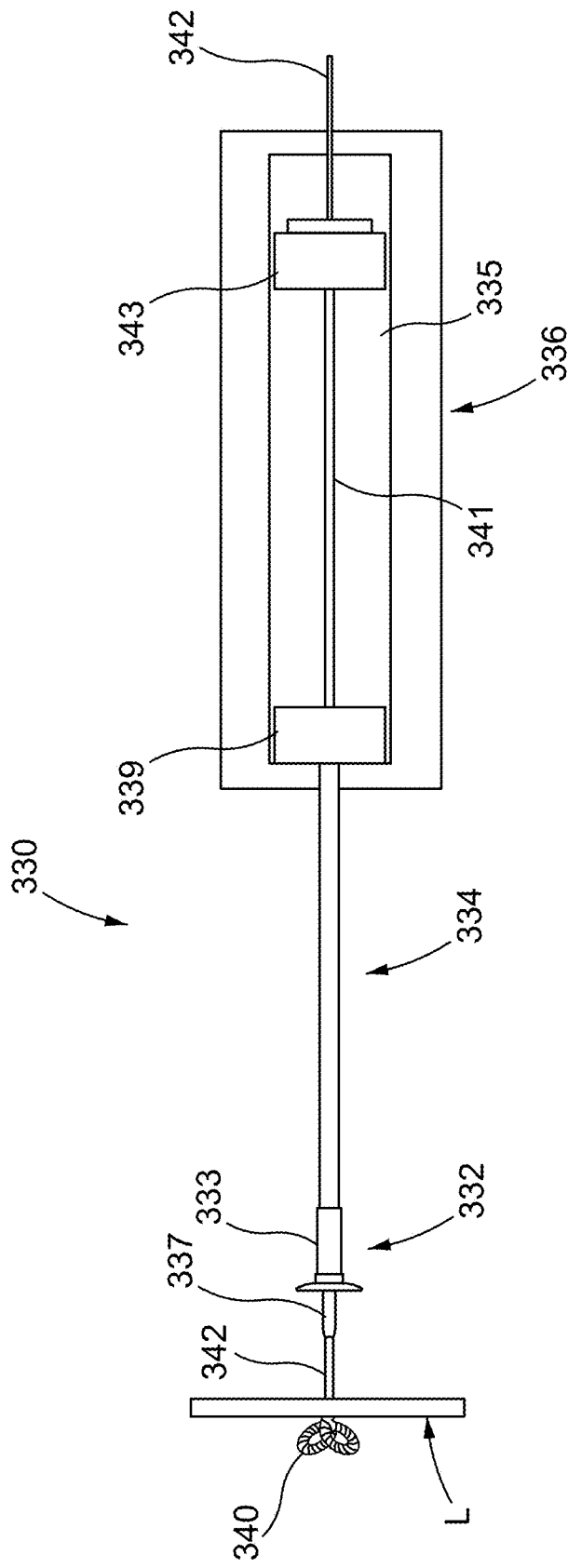
FIG. 14E is a schematic illustration of a side view of the distal anchor delivery device of FIG. 14A, shown in a fifth configuration as the delivery device is being retracted after deployment of the distal anchor.

After the distal coiled portion of the suture 342 is moved to the distal side of the leaflet L, the plunger is then released such that the plunger moves proximally, which moves or pushes the needle 341 and suture catch 346 proximally, pulling the suture 342 (e.g., suture strands extending from the coiled portion of the suture) through the pusher 337 to form the bulky knot configuration (as shown in FIG. 14D) of the distal anchor 340 by approximating opposite ends of the coils of the elongated coil portion of the suture 342 towards each other, to form one or more loops. As shown in FIG. 14D, by pulling on the proximal ends of the suture 342, the coils are pulled against the distal end of the pusher 337 to form the knot. After the distal anchor 340 has formed a knot, the proximal end portions of the suture 342 can be released from the suture catch 346 and the delivery device 330 can be withdrawn proximally, leaving the distal anchor 340 disposed on the distal side of the leaflet L (as shown in FIG. 14E), and two lengths or strands of the suture 332 extending out of the heart. In other words, with the suture 342 released from the suture catch 346, the delivery device 330 can be slid over the suture 342 for removal.

As described above for previous embodiments, the lengths or strands of the suture 342 between the distal anchor 340 and the opening in the heart can be adjusted until the desired length is established. The proximal ends of the suture 342 can then be secured to an outer surface of the heart at, for example, the apex region, with a proximal anchor (not shown). The proximal anchor can be, for example, a pledget, one or more knots, or other suitable anchoring device. As previously described, the above procedure can be performed multiple times on the same leaflet, and/or can be performed on the other mitral valve leaflet in the same manner. The result can thus be that one or more anchor-tether apparatuses (e.g., anchor-tether apparatus 145) as described above are each anchored on a distal side of a leaflet with a distal anchor and secured to the apex of the heart with a proximal anchor via the tether 342. Alternatively, if one or more anchor-tether apparatus are attached to both mitral valve leaflets an anchor-tether apparatus attached to each leaflet can be secured together in the heart by tying them together with knots or by another suitable attachment member (not shown), creating an edge-to-edge repair to decrease the septal-lateral distance of the mitral valve orifice. The two attached anchor-tether apparatus can be left loose or tensioned to create a "facilitated" edge-to-edge repair before being secured to an outer surface of the heart with a proximal anchor.

Figure 15C:
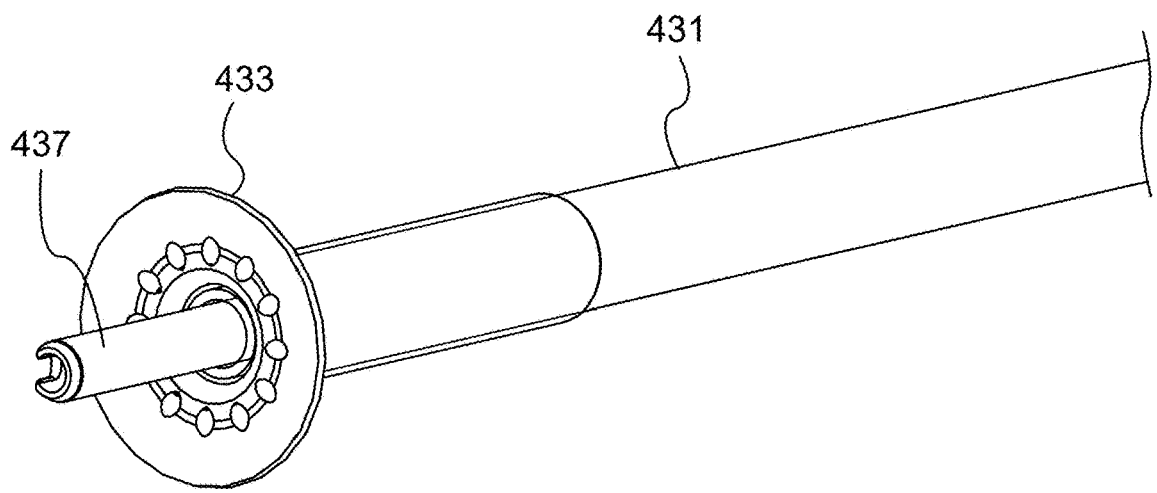
FIG. 15C is a perspective view of a distal end portion of the delivery device of FIG. 15A

FIGS. 15A-22C and 23-27 illustrate another embodiment of a delivery device that can be used to deliver and form a bulky knot distal anchor to be disposed on a distal side of a mitral valve leaflet using a short throw deployment sequence. As shown in cross-section in FIGS. 15A and 15B, a delivery device 430 includes a distal end portion 432, a proximal end portion 436 and a medial portion 434. The distal end portion 432 can include an end effector 433 (best shown in FIG. 15C) that can be placed in contact with a leaflet of a mitral valve as described above. The end effector 433 can be coupled to a distal end portion of an outer tube 431 (also shown in FIG. 15C) and a proximal end portion of the outer tube 431 is coupled to a handle 435 at the proximal end portion 436. An elongate pusher 437 is movably disposed within a lumen of the outer tube 431 (see e.g., FIG. 15C) and is coupled to a pusher hub 439 that is movably disposed within the handle 435 and releasably coupled to a plunger 448. A needle 441 is movably disposed within a lumen of the pusher 437 (see e.g., FIG. 17B) and is coupled to a needle hub 443 that is also coupled to the plunger 448. The plunger 448 is used to actuate or move the needle 441 and the pusher 437 during deployment of a distal anchor 440 (see e.g., FIGS. 19B and 20B) and is movably disposed at least partially within the handle 435. For example, the handle 435 defines a lumen in which the plunger 448 can be moved. During operation, the pusher 437 also moves within the lumen of the handle 435 as described in more detail below. The delivery device 430 also includes a locking lever 449 that can be used to prevent the plunger 448 from moving within the handle 435 during storage and prior to performing a procedure to deploy the distal anchor.

Figure 15D:
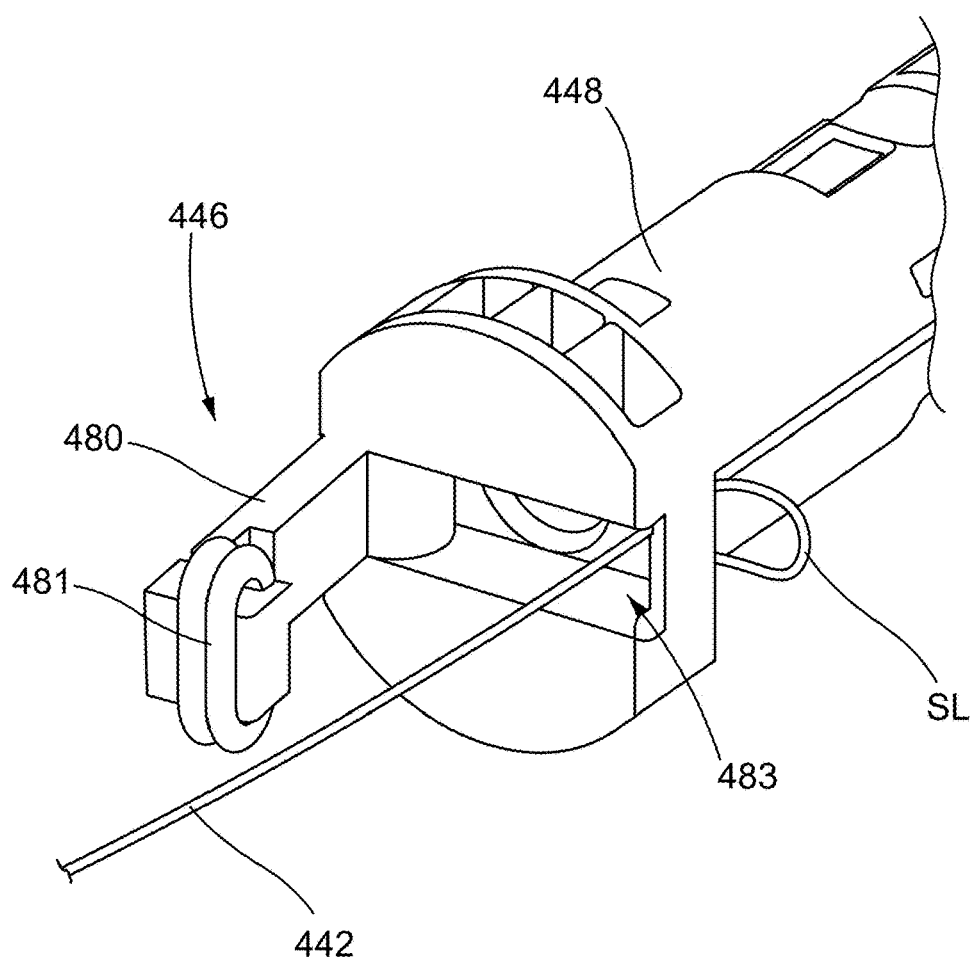
FIG. 15D is a perspective view of a proximal end portion of the delivery device of FIG. 15A showing a suture catch of the delivery device in an open position.
Figure 16:
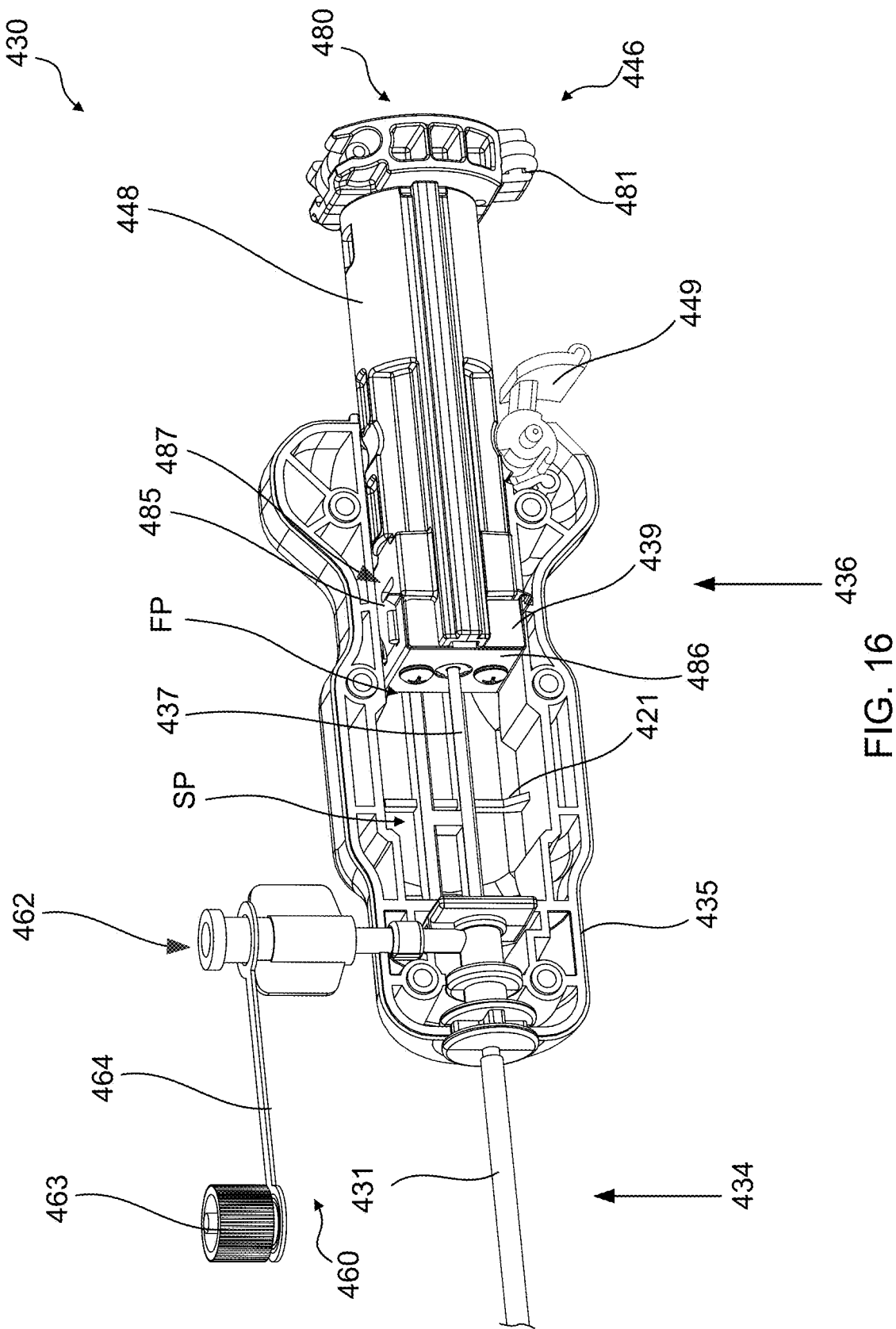
FIG. 16 is a perspective view shown partially in cross-section of the distal anchor delivery device of FIG. 15A, shown in a first configuration prior to deployment of a distal anchor through a mitral leaflet of a heart.

A suture catch 446 (also referred to as "tether catch") is also coupled to the plunger 448 at a proximal end of the delivery device 430 (best shown in FIG. 15D). The suture catch 446 can be configured to releasably hold or secure a suture 442 extending through the delivery device 430 during delivery of the distal anchor as described above and as described in more detail below. In some embodiments, the suture catch 446 can hold the suture 442 with a friction fit or with a clamping force and can have a lock that can be released after the distal anchor 440 has been deployed/formed into a bulky knot. The suture catch 446 includes an arm 480 and contact members 481 (e.g., silicone O-rings) coupled to the arm 480 (see e.g., FIG. 12D). The arm 480 can be moved from a closed position (as shown in FIGS. 15A, 15B, 16, 17A, 18A and 19A) in which the contact members 481 engage the suture strands 442 within a slot 483 in the plunger 448, to an open position (as shown in FIGS. 15D and 20A) thereby allowing the proximal end portions of the suture 442 to be released from the suture catch 446. The delivery device 430 can then be withdrawn proximally, leaving the distal anchor 440 disposed on the distal side of the leaflet L, and the two lengths of the suture 442 extending out of the heart, as described with respect to previous embodiments. When in the closed position, the arm 480 and the contact members 481 pinch or otherwise secure the suture 442 to prevent or otherwise limit the suture 442 from moving relative to the device 430. When in the open position (e.g., after delivery of the distal anchor 440 and during removal of the device 430 from the heart), the arm 480 and the contact members 481 allow movement of the suture 442 relative to the device 430 such that the device 430 can be separated from the suture 442, as described in more detail below.

A distal end portion of the suture 442 (also referred to herein as "tether") is formed into an elongated coiled configuration and is disposed within the outer tube 431 at the distal end portion 432 of the delivery device 430. For example, the coils of the suture 442 can be provided or shipped disposed around the needle 441 with the proximal most coil abutting against the suture 442. As described above for the suture 242 and the suture 342, two strands of the suture 442 extend from the distal elongated coiled portion of the suture 442, extend through the lumen of the needle 441, through a passageway of the plunger 448 and exit the plunger 448 at a proximal end portion of the plunger 448 (see e.g., FIG. 15D). The distal elongated coiled portion of the suture 442 will be formed into the distal anchor 440 (e.g., bulky knot) upon actuation of the delivery device 430 as described in more detail below. As discussed above for the distal anchors 140, 240 and 340, the distal anchor 440 (e.g., bulky knot) can be in the form of one or more multi-turn coils of the suture 442 that can be changed from the elongated coiled configuration during delivery to a knot configuration by approximating opposite ends of the coils towards each other, to form one or more loops.

Figure 22C:
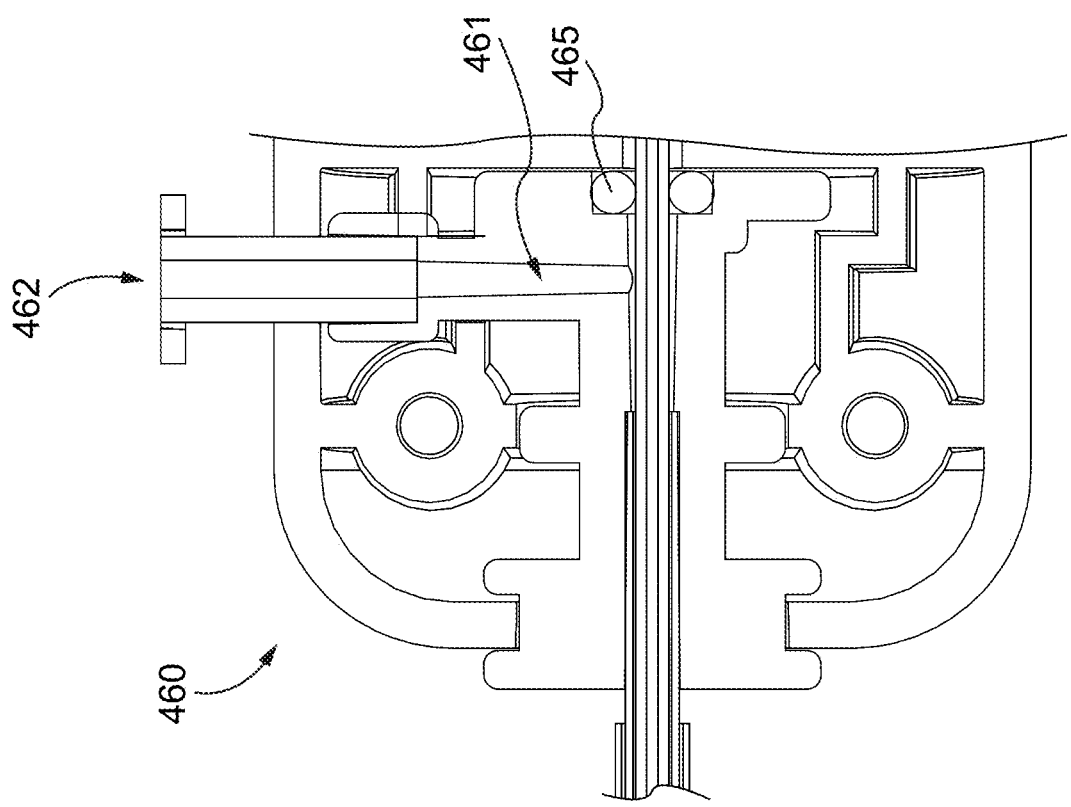
Figure 22B:
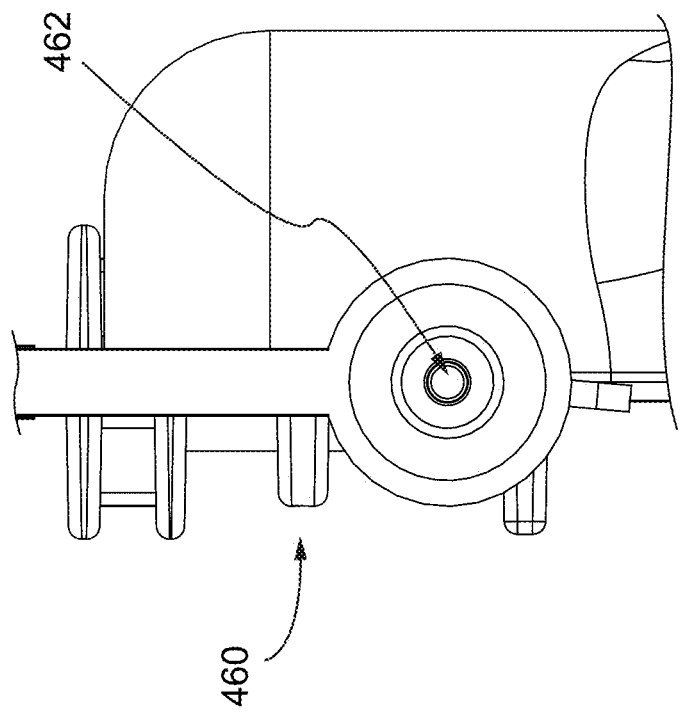

As shown in detail in FIGS. 22A-22C, the delivery device 430 also includes a fluid transfer system 460. The fluid transfer system 460 is configured to facilitate flushing of a portion of the delivery device 430 and/or to facilitate the removal of undesirable fluids during the procedure. In some instances, for example, the fluid transfer system 460 be used to flush air out of the delivery device 430 (e.g., air located between the pusher 437 and the outer tube 431). As another example, the fluid transfer system 460 can be used to limit or prevent blood from undesirably flowing from a patient into the delivery device 430 during a procedure. The fluid transfer system 460 includes a fluid pathway 461 and a connection port 462 disposed external to the handle 435. As shown best in cross-sectional view in FIG. 22C, the fluid pathway 461 is in fluid communication with the connection port 462 and a volume defined between the lumen of the outer tube 431 and an outer surface of the pusher 437. Further, as shown best in FIG. 22C, the fluid transfer system 460 includes a fluid sealing member 465 (e.g., an O-ring) disposed about the pusher 437 and configured to fluidically isolate the fluid pathway 461 from a volume within the handle 435 proximal to the fluid transfer system 460. The fluid transfer system 460 also includes connection port sealing member 463 (e.g., a cap, a plug, or the like) configured to be coupled to the connection port 462 to fluidically isolate the fluid pathway 461 from a volume external to the fluid transfer system 460 and/or the delivery device 430. Optionally, the connection port sealing member 463 can be retained and/or stored proximate to the connection port 462 via a leash member 464 (as shown in FIG. 22A).

To prepare the delivery device 430 for delivering and forming a distal anchor 440 within, for example, a left atrium of the heart to repair a mitral valve, the locking lever 449 is released from its locked or engaged position (e.g., its position during storage of the delivery device 430) in which the plunger 448 is prevented from moving (e.g., proximally and distally) within the handle 435 to its unlocked or disengaged position in which the plunger 448 can be moved within the handle, as described in further detail below.

Figure 23:
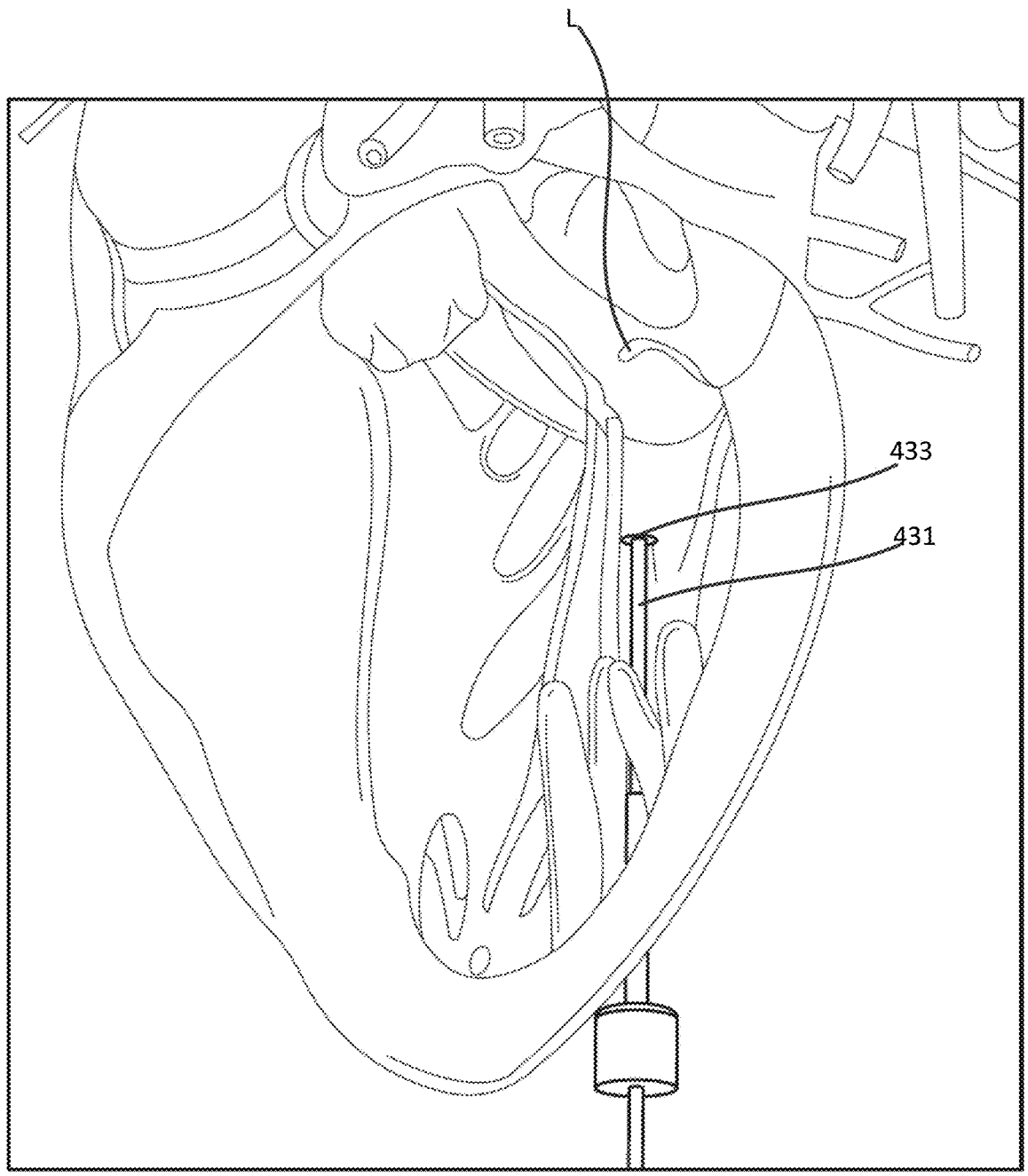
Figure 24:
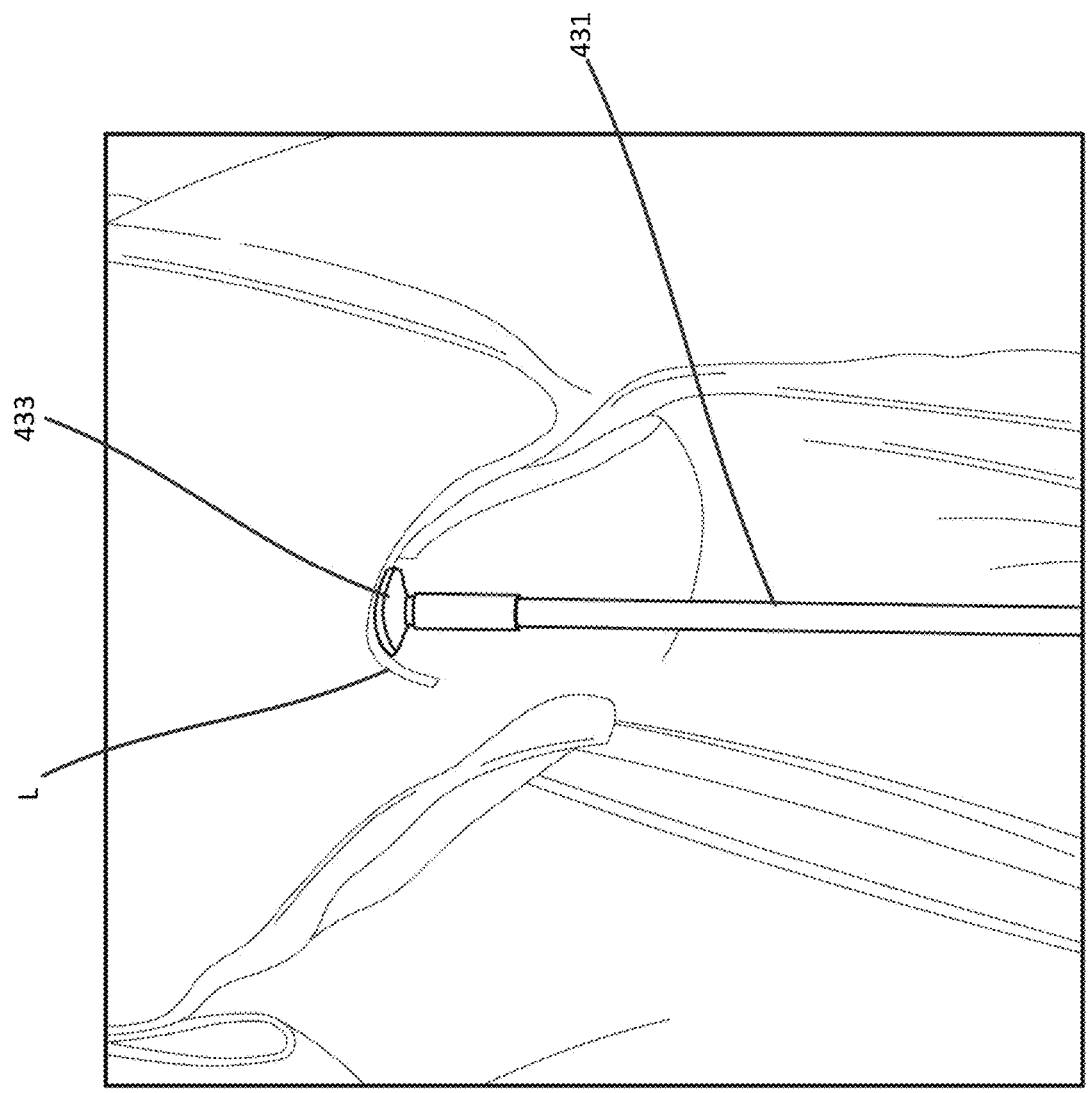
Figure 25:
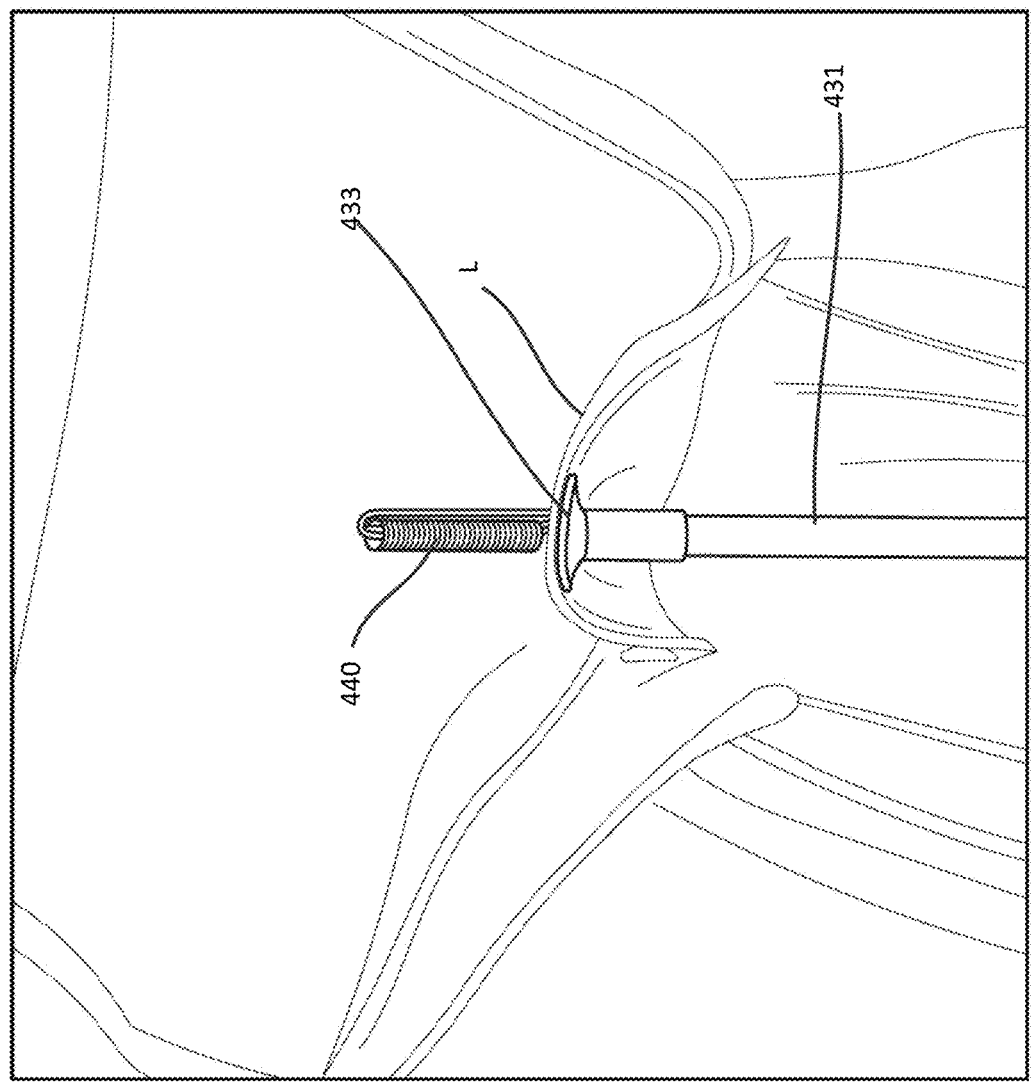
Figure 26:
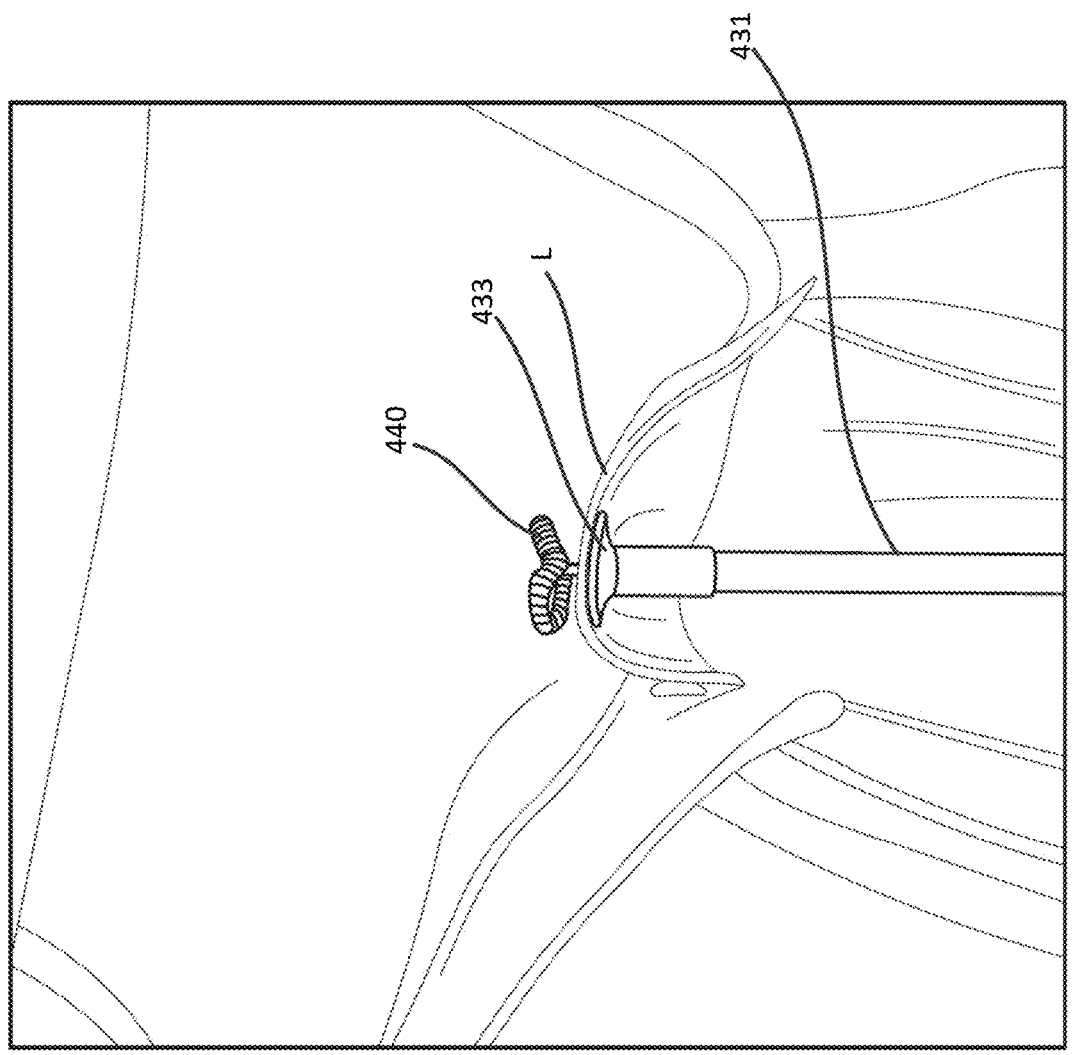

To deliver and form the distal anchor 440 within, for example, a left atrium of the heart to repair a mitral valve, the distal end portion of 432 of the delivery device 430 can be inserted through an apex portion of the heart and into the left ventricle until the end effector 433 contacts a proximal side of the mitral valve leaflet L as shown in progression in FIGS. 23 and 24. With the delivery device 430 positioned against the mitral leaflet L (see e.g., FIG. 24), and with a proximal end portion of the suture 442 (e.g., two suture strands of the suture 442) secured to the suture catch 446, the plunger 448 is actuated to move the needle hub 443, the needle 441, the pusher 437 and pusher hub 439, and the coiled portion of the suture 432 (e.g., the distal anchor 440) distally until the plunger 448 contacts a stop member 421 within the handle 435 (see e.g., FIG. 18A), which limits the travel of the plunger 448 in the distal direction. As the plunger 448 is actuated, a distal piercing portion 447 of the needle 441 punctures the leaflet L and forms an opening in the leaflet L (see e.g., FIG. 17B). Because the needle 441 is coupled to the plunger 448 and moves with the plunger 448, the distance the distal end portion of the needle 441 extends within the left atrium on the distal side of the leaflet L (see e.g., FIG. 17B) is determined by the amount of travel allowed by the plunger 448. Thus, in this embodiment, the delivery device 430 is configured to advance the distal end portion of the needle 441 a shorter distance, for example, between about 0.2-0.3 inches (e.g., 0.25 inches), or less, distally beyond the distal end of the delivery device 430 (e.g., beyond the end effector), compared to the embodiment of FIGS. 6-10 in which the needle extends about 1.0 inch. In other embodiments, the needle can be extended outside the delivery device a distance of about 0.15-0.4 inches. For example, in some embodiments, the needle extends until the distal tip of the needle 441 and a first wrap or two of the coiled suture 442 extend through the leaflet. When the plunger 448 reaches the stop member, the pusher 437 and pusher hub 439 are released from the plunger 448 and are advanced further distally to a distal position within the handle 435, as shown in progression in FIGS. 17A and 18A. Details of how the pusher 437 and pusher hub 439 are moved within the lumen of the handle 435 and released from the plunger 448 are described below with respect to FIGS. 18A-21.

Figure 17A:
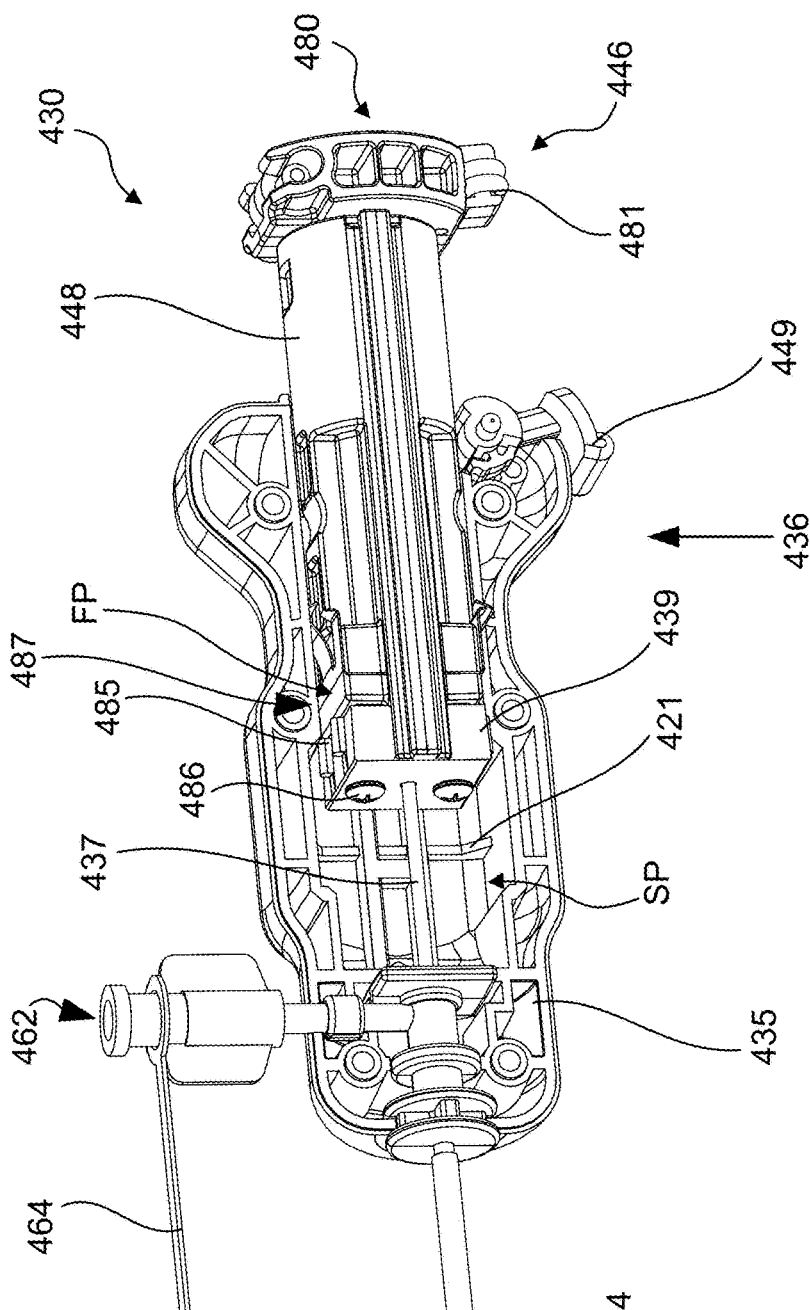
FIG. 17A is a perspective view shown partially in cross-section of the distal anchor delivery device of FIG. 15A, shown in a second configuration during deployment of a distal anchor.
Figure 17B:
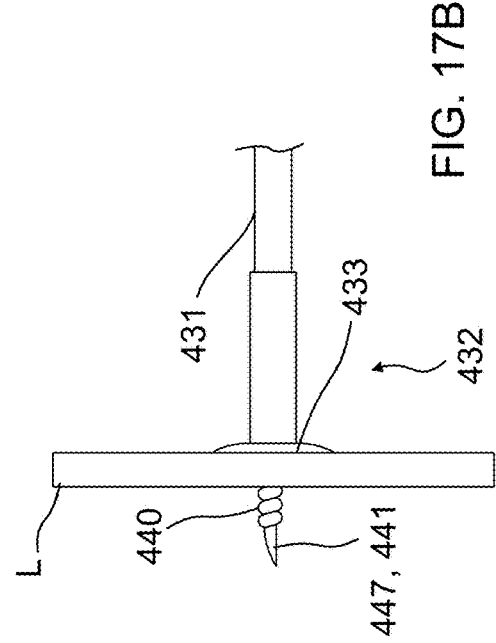
FIG. 17B is a side view of a distal end portion of the delivery device of FIG. 15A, shown with the distal anchor in a first configuration.

As shown in FIGS. 17A and 18A, the pusher hub 439 is configured to complimentarily mate with an opening 492 defined by and located at a distal end portion of the plunger 448. In use, prior to deployment, a proximal end portion of the pusher hub 439 is disposed within the opening 492 defined by the plunger 448 (see, e.g., FIGS. 16 and 17A). In this position, a pair of tabs 485 of a spring member 486 coupled to the pusher hub 439 are disposed within slots 487 defined by the plunger 448. For example, the spring member 486 can have a biased configuration in which the tabs 485 are disposed in an open position, and when the pusher hub 439 is coupled to the plunger 448 the tabs 485 are compressed by the inner walls of the handle 435, which define a first portion FP of a passageway within the handle 435. As the pusher hub 439 is moved distally, the spring member 486 will slide into a second portion SP of the passageway of the handle 435 which has a larger size, allowing the tabs 485 to move to their biased open configuration and disengaging the tabs 485 from the slots 487 of the plunger 448 (see, e.g., the progression in FIGS. 17A and 18A).

Figure 21:
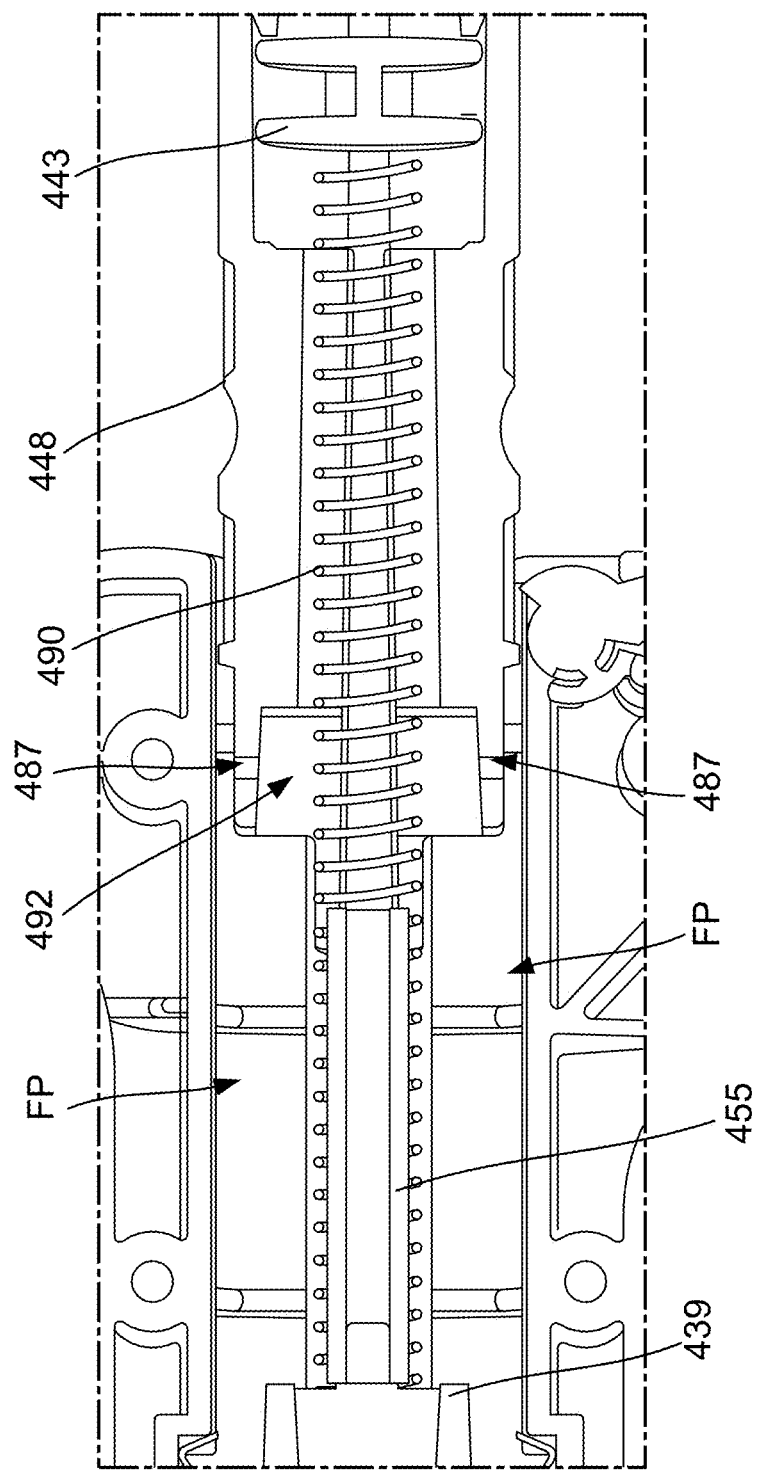
FIG. 21 is a cross-sectional side view the delivery device of FIG. 15A, showing the pusher hub when released from the plunger during deployment.

When the plunger 448 is actuated (i.e., moved distally within the handle 435), the pusher hub 439 will move distally with the plunger 448 until the plunger 448 reaches the stop member 421 (see e.g., FIG. 18A), at which point the pusher hub 439 is moved into the second portion SP of the passageway of the handle 435 as described above, allowing the tabs 485 on the spring member 486 to disengage or release the pusher hub 439 from the plunger 448. Upon release from the plunger 448, the pusher 437 and the pusher hub 439 are advanced further distally to a distal position within the handle 435 as shown in FIG. 18A, in response to a force provided by a biasing member 490 (e.g., a compression spring) disposed within a lumen of the plunger 448. The biasing member 490 is coupled to and disposed between the pusher hub 439 and the needle hub 443, as shown in FIG. 21. In this manner, with use of the biasing member 490, a desirable and repeatable force can be applied to the pusher 437 and the pusher hub 439, resulting in a desirable and repeatable delivery of the distal anchor 440.

Prior to disengagement of the pusher 437 and the pusher hub 439 from the plunger 448 (e.g., prior to use of the delivery device 430 or during use as the distal piercing portion 447 of the needle 441 punctures the leaflet L and forms an opening in the leaflet L), the biasing member 490 is in a compressed configuration (not shown) and the pusher 437 and the pusher hub 439 are in their ready state (see e.g., FIGS. 16 and 17A), in which a portion of the pusher hub 439 is disposed within the opening 492 of the plunger 448 as described above. To releasably retain the biasing member 490 in the compressed configuration and the pusher 437 and pusher hub 439 in their ready state, the pair of tabs 485 of the spring member 486 are disposed within the slots 487 of the plunger 448 and the plunger 448 is disposed in the first portion of the passageway within the handle 435.

As shown in FIG. 21, a guide member 455 is disposed within a lumen defined by the biasing member 490 and coupled to the pusher hub 439. During distal advancement of the pusher 437 and the pusher hub 439 within the handle 435, and transition of the biasing member 490 between its unbiased compressed configuration and is biased uncompressed configuration, the guide member 455 can facilitate desirable alignment within the handle 435 (e.g., alignment within the handle 435 of the pusher 437, the pusher hub 439, and the plunger 448). In addition, the guide member 455 can provide structural support to the biasing member 490 (e.g., during transition of the biasing member 490 between its biased and unbiased configurations).

Although the lumen of the handle 435 is shown in this embodiment as being rectangular, in some embodiments, the lumen of the handle can have any suitable shape (e.g., a circular or semi-circular shape). In such embodiments, the components that cooperatively function within the handle 435 (e.g., the pusher 437, the pusher hub 439, the plunger 448), as described above with respect the delivery device 430, can be suitably sized and/or shaped to cooperatively function with any shape and/or size selected for a particular handle and lumen defined therein.

In use, as the plunger 448 is actuated to move the pusher 437 and the pusher hub 439 distally within the handle 435, the plunger 448 will reach the stop member 421 at which point in time the spring member 486 will slide into the second portion SP of the passageway of the handle 435 which has the larger size, allowing the tabs 485 to move to their biased open configuration and disengaging the tabs 485 from the slots 487 of the plunger 448. In this manner, the biasing member 490 will be released from its compressed configuration and transition towards a biased uncompressed configuration thereby resulting in travel of the pusher 437 and the pusher hub 439 distally within the handle 435. As the pusher 437 is moved distally, a distal end of the pusher 437 moves or pushes the distal coiled portion of the suture 442 (i.e., distal anchor 440) over the distal end of the needle 441 and further within the left atrium of the heart on a distal side of the mitral leaflet (see, e.g., FIGS. 18A, 18B and 25), such that the coiled portion of the suture extends distally beyond a distal end of the needle 441. For example, in some embodiments, at least half a length of the distal coiled portion of the suture 442 extends beyond the distal end of the needle 441. In some embodiments, at least three quarters of the length of the distal coiled portion of the suture 442 extends beyond the distal end of the needle 441. In other embodiments, the entire coiled portion of the suture 442 extends beyond the distal end of the needle 441. To allow the distal coiled portion of the suture 442 (i.e., distal anchor 440) to slide relative to the plunger 448, when the suture 442 is loaded within the delivery device 430, there is slack SL (a portion of which is shown in FIG. 15D) in the suture 442 between the distal coiled portion of the suture 442 and the suture lock within the suture catch 446.

Figure 19A:
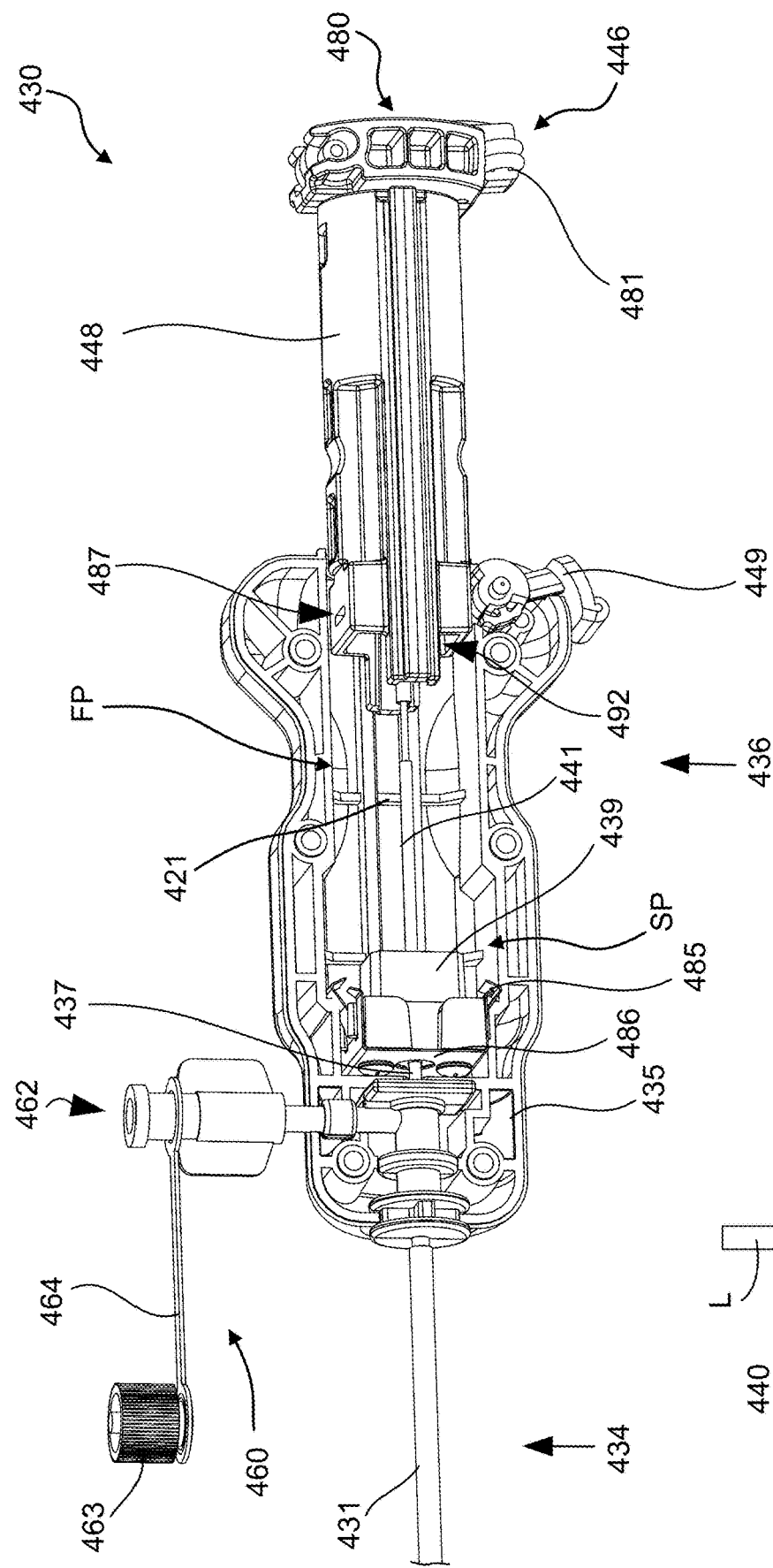
FIG. 19A is a perspective view shown partially in cross-section of the delivery device of FIG. 15A, shown in a third configuration.
Figure 19B:
FIG. 19B is a side view of a distal end portion of the delivery device of FIG. 15A, showing formation of the distal anchor into a second configuration during deployment.

After the distal coiled portion of the suture 442 is moved to the distal side of the leaflet L, the plunger 448 is released to allow the plunger 448 to move proximally, which moves or pushes the needle 441 and suture catch 446 proximally, as shown in FIG. 19A. For example, in some embodiments, the plunger 448 can be actuated by the user manually pushing the plunger distally within the handle 435 with for example a thumb or finger. To release the plunger 448, the user can release his thumb which allows the plunger 448 to be moved back proximally. For example, in some embodiments, when the user releases his thumb from the plunger 448, a biasing member (e.g., a spring) (not shown) can push the plunger 448 back in the proximal direction. When the suture catch 446 is moved proximally, this in turn pulls the suture 442 (e.g., suture strands extending from the coiled portion of the suture) proximally to form the bulky knot configuration of the distal anchor 440 against the distal end of the pusher 437 (see e.g., FIGS. 18B, 19B, 25 and 26). For example, as described above, the bulky knot is formed by approximating opposite ends of the coils of the elongated coil portion of the suture 442 towards each other, to form one or more loops, as shown in FIG. 16B. After the distal anchor 440 has formed a knot, the proximal end portions of the suture 442 can be released from the suture catch 446. The delivery device 430 can then be withdrawn proximally, leaving the distal anchor 440 disposed on the distal side of the leaflet L, as shown in FIGS. 20A and 20B, and two lengths or strands of the suture 432 extending from the proximal side of the leaflet L (see e.g., FIG. 27) and out of the heart. In other words, with the suture 442 released from the suture catch 446 the delivery device 430 can be slid over the suture 442 for removal.

As described above for previous embodiments, the lengths or strands of the suture 442 between the distal anchor 440 and the opening in the heart can be adjusted until the desired length is established. The proximal ends of the suture 442 can then be secured to an outer surface of the heart at, for example, the apex, with a proximal anchor (not shown). The proximal anchor can be, for example, a pledget, one or more knots, or other suitable anchoring device. As previously described, the above procedure can be performed multiple times on the same leaflet, and/or can be performed on the other mitral valve leaflet in the same manner. The result can thus be that one or more anchor-tether apparatuses (e.g., anchor-tether apparatus 145) as described above are each anchored on a distal side of a leaflet with a distal anchor and secured to the apex of the heart with a proximal anchor via the tether 442. Alternatively, if one or more anchor-tether apparatus are attached to both mitral valve leaflets, an anchor-tether apparatus attached to each leaflet can be secured together in the heart by tying them together with knots or by another suitable attachment member, creating an edge-to-edge repair to decrease the septal-lateral distance of the mitral valve orifice. The two attached anchor-tether apparatus can be left loose or tensioned to create a "facilitated" edge-to-edge repair before being secured to an outer surface of the heart with a proximal anchor. As shown in FIG. 27, with the anchor-tether apparatus secured to the mitral valve leaflet L, when closed, the free margins or edges of the leaflets come together and form a tight junction, the arc of which is known as the line, plane or area of coaptation AC as previously described.

FIGS. 14A-14E described above illustrate one example method and device for deploying a bulky knot distal anchor using a delivery device that utilizes a short throw deployment sequence configured to insert the distal end portion and piercing member of the needle a shorter distance into the left atrium than as shown and described above for the embodiment of FIGS. 6-10. As shown and described with respect to FIGS. 14A-14E, the distal end portion of the needle is used to puncture the leaflet tissue and form an opening in the leaflet tissue, but does not extend as far into the left atrium. In another embodiment, a bulky knot distal anchor can be deployed/formed using a delivery device that utilizes a full forward short throw deployment sequence. The full forward short throw deployment sequence is similar to the short throw deployment sequence of FIGS. 14A-14E, but causes the bulky knot distal anchor to be deployed/formed by moving the pusher distally relative to the needle rather than pulling on the proximal ends of the suture to pull the coils against the distal end of the pusher. FIGS. 28A-28E are schematic illustrations of an embodiment of a delivery device for delivering and deploying a distal anchor and configured to provide such a full forward short throw deployment sequence.

As shown in FIGS. 28A-28E, a delivery device 530 includes a distal end portion 532, a proximal end portion 536 and a medial portion 534. The distal end portion 532 includes an end effector 533 that can be placed in contact with a leaflet L of a mitral valve as described above with respect to FIGS. 14A-14E. The end effector 533 is coupled to a distal end portion of an outer tube 531 and a proximal end portion of the outer tube 531 is coupled to a handle 535 at the proximal end portion 536 of the delivery device 530. The end effector 533 can distribute the force of the outer tube 531 over a larger area to prevent/eliminate puncturing of the leaflet with the delivery device 530 during deployment. In some embodiments, the end effector 533 can include a balloon (not shown). An elongate pusher 537 is movably disposed within a lumen of the outer tube 531 and is coupled to a pusher hub 539 that is movably disposed within the handle 535 and releasably coupled to a plunger (not shown). For example, the plunger can be constructed the same as or similar to the plunger 448 described above and function in a similar manner. A needle 541 (see FIGS. 28C-28E) is movably disposed within a lumen of the pusher 537 and is coupled to a needle hub 543 that is also releasably coupled to the plunger (not shown). The plunger is used to actuate or move the needle 541 and the pusher 537 during deployment of a distal anchor 540 and can be movably disposed at least partially within the handle 535. For example, the handle 535 defines a lumen in which the plunger can be moved. During operation, the pusher 537 also moves within the lumen of the handle 535 as described in more detail below. The delivery device 530 can also include a locking lever (not shown) that can be used to prevent the plunger from moving within the handle 535 during storage and prior to performing a procedure to deploy the distal anchor. For example, the locking lever can be similar to or the same as the locking lever 449 described above.

A suture catch 546 (also referred to as "tether catch") can be coupled to the plunger at a proximal end of the delivery device 530. The suture catch 546 is configured to releasably hold or secure a suture 542 extending through the delivery device 530 during delivery of the distal anchor 540 as described above for previous embodiments. In some embodiments, the suture catch 546 can hold the suture 542 with a friction fit or with a clamping force and can have a lock that can be released after the distal anchor 540 has been deployed/formed into a bulky knot.

As described above for previous embodiments, the suture 542 (also referred to herein as "tether") can be formed into an elongated coiled configuration and is disposed within the outer tube 531 at the distal end portion 532 of the delivery device 530. As described above, for example, for suture 242, two strands of the suture 542 can extend from the distal elongated coiled portion of the suture 542, extend through the lumen of the needle 541, through a passageway of the plunger and exit the plunger and needle 541 at a proximal end portion of the plunger. The distal elongated coiled portion of the suture 542 will be formed into the distal anchor 540 (e.g., bulky knot) upon actuation of the delivery device 530 as described in more detail below. As discussed above for previous embodiments, the distal anchor 540 can be in the form of one or more multi-turn coils of the suture 542 that can be changed from the elongated coiled configuration during delivery to a knot configuration by approximating opposite ends of the coils towards each other, to form one or more loops.

To deliver and form the distal anchor 540 within, for example, a left atrium of the heart to repair a mitral valve, the distal end portion of 532 of the delivery device 530 can be inserted through an apex portion or region of the heart and into the left ventricle until the end effector 533 contacts a proximal side of the mitral valve leaflet L as shown in FIG. 28A. In this embodiment, with the delivery device 530 positioned against only the ventricular side of the mitral leaflet L, without contacting the atrial side of that leaflet, and with a proximal end portion of the suture 542 (e.g., two suture strands of suture 542) secured to the suture catch 546, the plunger (not shown) can be actuated (e.g., moved or pushed in a distal direction relative to the handle 535). The actuation of the plunger moves the needle hub 543, the needle 541, the pusher 537 and pusher hub 539, the suture catch 546, and the coiled portion of the suture 542 (e.g., distal anchor 540) distally until the needle hub 543 (and needle 541) and the suture catch 546 reach a preset location within the handle where the needle hub 543, needle 541, and suture catch 546 are disengaged from the plunger and their travel in the distal direction is stopped. The pusher 537, the pusher hub 539, and the coiled portion of the suture 542 continue to be moved distally by the plunger.

In some embodiments, for example, a delivery device can include a release mechanism configured to disengage the needle hub, the needle, and the suture catch from the plunger such that the plunger can continue to advance distally and move the pusher, the pusher hub, and the coiled portion of the suture distally. In some embodiments, the release mechanism can be configured for automatic disengagement, while in other embodiments, the mechanism can be configured to be actuated by the operator. In some embodiments, the delivery device can also include one or more stop members within the handle that can engage or contact the needle hub (and suture catch) to limit or stop the travel of the needle (and suture catch) in the distal direction.

As the plunger is actuated, and prior to the needle 541 being disengaged from the plunger, a distal piercing portion 547 of the needle 541, and in some cases, at least the first wrap of the coiled portion of the suture 542, punctures the leaflet L and forms an opening in the leaflet L (see e.g., FIG. 28B). The distance the distal piercing portion 547 of the needle 541 extends within the left atrium on the distal side of the leaflet L can be determined, for example, by the preset allowed amount of travel of the needle 541 described above (e.g., in some embodiments, the amount of travel can be determined at least in part by a stop member within the handle and/or a mechanism to release the needle hub from the plunger). In some embodiments, the delivery device 530 can be configured to advance the distal piercing portion 547 of the needle 541 a shorter distance into the left atrium than as shown and described above for the embodiment of FIGS. 6-10. For example, in some embodiments, the needle hub 543 can travel about 0.25 inches during actuation of the plunger. In some embodiments, the needle 541 can be extended outside of the distal end of the delivery device (e.g., beyond the end effector) half the distance that is shown and described for the embodiment of FIGS. 6-10. In some embodiments, the needle 541 can be extended outside the delivery device a distance of about 0.2-0.3 inches (e.g., 0.25 inches).

As described above, when the needle hub 543, the needle 541 and suture catch 546 disengage from the plunger, the plunger continues to be moved distally, which in turn moves the pusher 537, the pusher hub 539, and the coiled portion of the suture 542 (e.g., distal anchor 540) further distally. For example, in some embodiments, the pusher 537 can be moved distally about an additional 0.25-0.65 inches (e.g., 0.4 inches) during actuation of the plunger. Thus, in some embodiments, the total travel of the pusher can be, for example, about 0.40-0.90 inches (e.g., 0.65 inches). Similarly, in some embodiments, the pusher can be extended through the proximal side of the heart valve leaflet a distance of about 0.4-0.9 inches (e.g., 0.65 inches) from the proximal side of the heart valve leaflet. As yet a further example of the short throw deployment sequence, the pusher can be moved through the opening of the leaflet from the proximal side of the leaflet and can extend a distance of about 0.25-0.65 inches (e.g., 0.4 inches) from and distal to the distal side of the leaflet.

As the pusher 537 is moved distally, with the suture catch 546, the needle 541 and the needle hub 543 in fixed positions relative to the pusher 537 (i.e., the suture catch 546, the needle 541, and the needle hub 543 are disengaged from the plunger), a distal end of the pusher 537 moves or pushes the distal coiled portion of the suture 542 (i.e., distal anchor 540) over the distal end of the needle 541 and further within the left atrium of the heart on a distal side of the mitral leaflet (see FIG. 28C). In this manner, the distal end of the pusher 537 pushes the coiled portion of the suture 542 (i.e., distal anchor 540) distally off the needle 541. To allow the distal coiled portion of the suture 542 (i.e., distal anchor 540) to slide relative to and eventually off the needle 541, when the suture 542 is loaded within the delivery device 530, there can be slack formed in the suture 542 between the distal coiled portion of the suture 542 and the suture lock within the suture catch 546. As shown in FIG. 28D, as the pusher 537 continues to move distally relative to the needle 541, the coiled portion of the suture 542 forms the bulky knot configuration of the distal anchor 540 by approximating opposite ends of the coils of the elongated coil portion of the suture 542 towards each other, to form one or more loops (two loops are shown in FIG. 28D). For example, with the opposite end portions of the suture 542 fixed and secured within the suture catch 546, as the pusher 537 moves distally, the coils are forced against the distal end of the pusher 537 to form the knot.

In use, in some instances, the plunger can be actuated to move the needle hub 543 as described above, while maintaining the entire distal portion of the delivery device 530 on the ventricular side of the leaflet L. In this manner, in such instances, the distal anchor 540 can be delivered to and/or deployed at the distal side of the leaflet without some form of mechanical fixation to and/or capturing of the leaflet L prior to piercing the leaflet with the needle 541. Unlike conventional open-heart surgery, where the heart is stopped and the surgeon can see and manipulate stationary leaflets, in a minimally invasive procedure (e.g., with a beating heart), the operator cannot see the leaflet directly, and instead, must rely on an ultrasonic or other image of the moving leaflet and the device. In practice, this image is often displayed on a display device for the operator after a slight time delay. As such, immobilizing the otherwise moving leaflet can be challenging and has the potential to further damage the leaflet. Being able to deliver and deploy a distal anchor without having to mechanically fix to and/or capture the otherwise moving leaflet (e.g., prior to piercing the leaflet to form an opening through with the distal anchor is delivered) eliminates or at least limits the challenges discussed above. Additionally, being able to deliver and deploy the distal anchor using a single device (e.g., without using a separate device to immobilize and/or capture the leaflet) further reduces challenges and risks associated with such procedures.

Figure 28E:
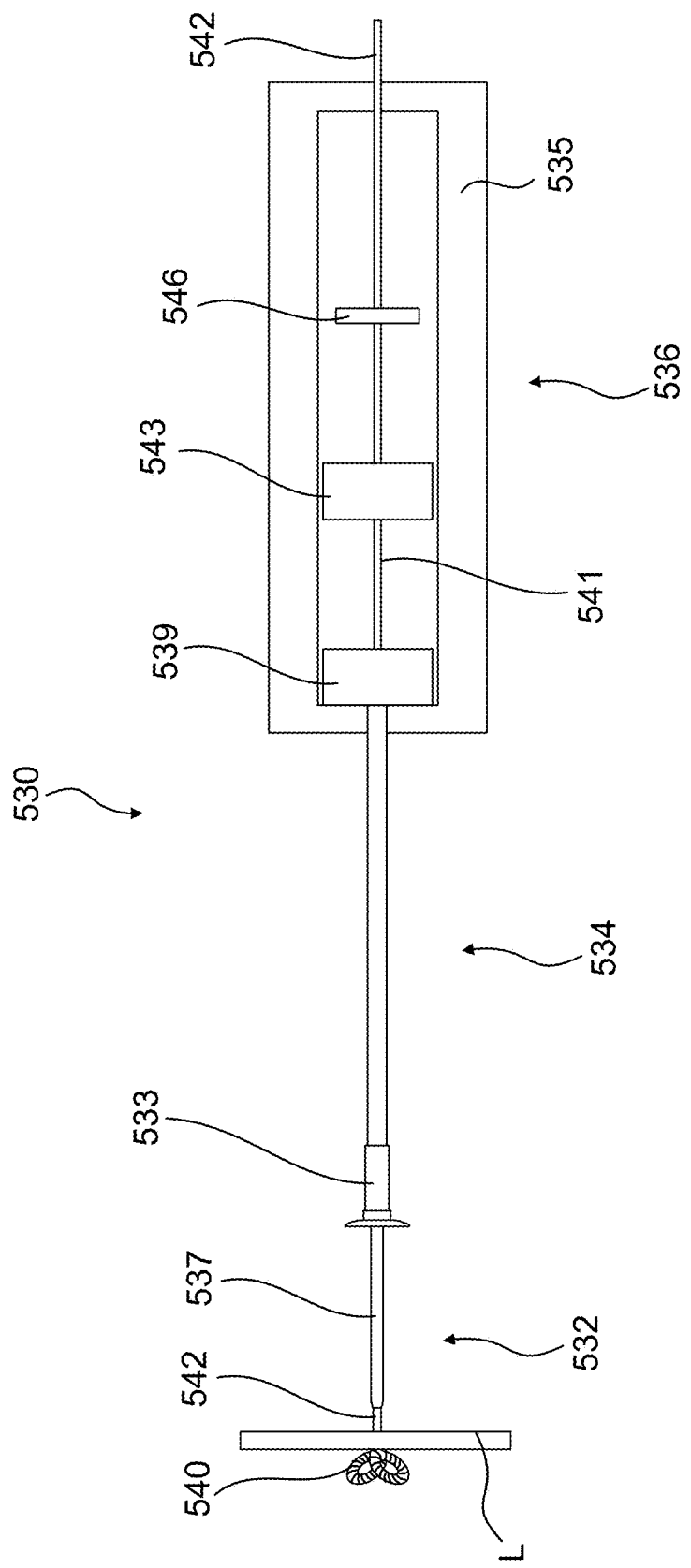
FIG. 28E is a schematic illustration of a side view of the distal anchor delivery device of FIG. 28A, shown in a fifth configuration as the delivery device is being retracted after deployment of the distal anchor.

After the distal anchor 540 has formed a knot, the proximal end portions of the suture 542 can be released from the suture catch 546 and the delivery device 530 can be withdrawn proximally, leaving the distal anchor 540 disposed on the distal side of the leaflet L (as shown in FIG. 28E), and two lengths or strands of the suture 532 extending out of the heart. In other words, with the suture 542 released from the suture catch 546 the delivery device 530 can be slid proximally over the suture 542 for removal. Forming/deploying the bulky knot using the full forward short throw deployment sequence described above can simplify the procedure for an operator of the delivery device 530 because the operator can deploy the bulky knot by applying a single distal force to the plunger. Further, after the plunger is actuated and the bulky knot is formed, the operator can remove the delivery device 530 from the patient by withdrawing the delivery device 530 proximally without, for example, having to wait for the plunger to move proximally to form the bulky knot, leaving the bulky knot disposed on the distal side of the leaflet L. Simplifying a procedure in this manner such that an operator can implant an artificial chorda by applying, for example, a push force to the plunger, and then remove the entire delivery device by withdrawing the delivery device proximally, promotes a repeatable and predicable procedure.

As described above for previous embodiments, the lengths or strands of the suture 542 between the distal anchor 540 and the opening in the heart can be adjusted until the desired length is established. The proximal ends of the suture 542 can then be secured to an outer surface of the heart at, for example, the apex region, with a proximal anchor (not shown). The proximal anchor can be, for example, a pledget, one or more knots, or other suitable anchoring device. As previously described, the above procedure can be performed multiple times on the same leaflet, and/or can be performed on the other mitral valve leaflet in the same manner. The result can thus be that one or more anchor-tether apparatuses (e.g., anchor-tether apparatus 145) as described above are each anchored on a distal side of a leaflet with a distal anchor 540 and secured to the apex of the heart with a proximal anchor via the tether 542. Alternatively, if one or more anchor-tether apparatus are attached to both mitral valve leaflets, an anchor-tether apparatus attached to each leaflet can be secured together in the heart by tying them together with knots or by another suitable attachment member (not shown), creating an edge-to-edge repair to decrease the septal-lateral distance of the mitral valve orifice. The two attached anchor-tether apparatus can be left loose or tensioned to create a "facilitated" edge-to-edge repair before being secured to an outer surface of the heart with a proximal anchor.

In some embodiments, the suture catch can be coupled in a fixed position relative to the handle of the delivery device, rather than being coupled to the plunger. Thus, the proximal portion of the suture coupled to the suture catch is in a fixed position relative to the handle. In such embodiments, there can be sufficient slack formed in the suture between the distal coiled portion of the suture and the suture lock within the suture catch to allow the distal coiled portion of the suture (i.e., distal anchor) to slide relative to and eventually off the needle, when the plunger is advanced distally. Alternatively or in addition to, providing slack in the suture, a spring can be disposed in the handle and coupled to the suture between the distal coiled portion of the suture (i.e., the distal anchor) and the suture lock, which can expand longitudinally as the plunger is moved distally.

FIGS. 28A-28E described above illustrate one example method and device for deploying a bulky knot distal anchor using a delivery device that utilizes a full forward short throw deployment sequence configured to insert the distal end portion and piercing member of the needle a shorter distance into the left atrium than as shown and described above for the embodiment of FIGS. 6-10. Such a full forward short throw delivery sequence is configured to cause the bulky knot distal anchor to be deployed/formed by moving the pusher distally relative to the needle rather than pulling on the proximal ends of the suture to pull the coils against the distal end of the pusher. In another embodiment, a bulky knot distal anchor can be deployed/formed using a delivery device that utilizes an independent full forward short throw deployment sequence. The independent full forward short throw deployment sequence is similar to the full forward short throw deployment sequence of FIGS. 28A-28E, except the pusher and the needle are configured to move independent of each other (e.g., the pusher and the needle can each be coupled to a different component of the actuator and/or be actuated separately). For example, the pusher and needle can be moved within the handle and the outer tube independently of each other and during varying time periods in response to separate force-providing mechanisms. FIGS. 29A-29E are schematic illustrations of an embodiment of a delivery device for delivering and deploying a distal anchor using an independent full forward short throw deployment sequence.

As shown in FIGS. 29A-29E, a delivery device 630 includes a distal end portion 632, a proximal end portion 636 and a medial portion 634. The distal end portion 632 includes an end effector 633 that can be placed in contact with a leaflet L of a mitral valve as described above with respect to previous embodiments. The end effector 633 is coupled to a distal end portion of an outer tube 631 and a proximal end portion of the outer tube 631 is coupled to a handle 635 at the proximal end portion 636 of the delivery device 630. The end effector 633 can distribute the force of the outer tube 631 over a larger area to prevent/eliminate puncturing of the leaflet with the delivery device 630 during deployment. In some embodiments, the end effector 633 can include a balloon (not shown). An elongate pusher 637 is movably disposed within a lumen of the outer tube 631 and is coupled to a pusher hub 639 that is movably disposed within the handle 635 and coupled to an actuator (not shown). The actuator can be used to actuate or move the pusher hub 639 and the pusher 637 during deployment of a distal anchor 640 and can be movably disposed at least partially within the handle. A needle 641 (see FIG. 29B) is movably disposed within a lumen of the pusher 637 and is coupled to a needle hub 643 that is coupled to an actuator (not shown) and/or energy storage member (not shown). The actuator can be used to actuate or move the needle hub 643 and the needle 641 (both independent of the pusher hub and the pusher) during deployment of the distal anchor 640 and can be movably disposed at least partially within the handle 635. For example, the handle 635 can define a lumen in which the actuator or a portion of the actuator can be actuated and/or moved. The delivery device 630 can also include a locking lever (not shown) that can be used to prevent the actuator(s) and/or one or more of its constituent components from actuating and/or moving within or relative to the handle 635 during, for example, storage and/or prior to performing a procedure to deploy the distal anchor. For example, the locking lever can be similar to or the same as the locking lever 449 described above.

A suture catch 646 (also referred to as "tether catch") can be coupled to a proximal end of the delivery device 630. The suture catch 646 is configured to releasably hold or secure a suture 642 extending through the delivery device 630 during delivery of the distal anchor 640 as described above for previous embodiments. In some embodiments, the suture catch 646 can hold the suture 642 with a friction fit or with a clamping force and can have a lock that can be released after the distal anchor 640 has been deployed/formed into a bulky knot.

As described above for previous embodiments, the suture 642 (also referred to herein as "tether") can be formed into an elongated coiled configuration and is disposed within the outer tube 631 at the distal end portion 632 of the delivery device 630. As described above, for example, for suture 242, two strands of the suture 642 can extend from the distal elongated coiled portion of the suture 642, and extend through the lumen of the needle 641. The distal elongated coiled portion of the suture 642 will be formed into the distal anchor 640 (e.g., bulky knot) upon actuation of the delivery device 630 as described in more detail below. As discussed above for previous embodiments, the distal anchor 640 can be in the form of one or more multi-turn coils of the suture 642 that can be changed from the elongated coiled configuration during delivery to a knot configuration by approximating opposite ends of the coils towards each other, to form one or more loops.

Figure 29A:
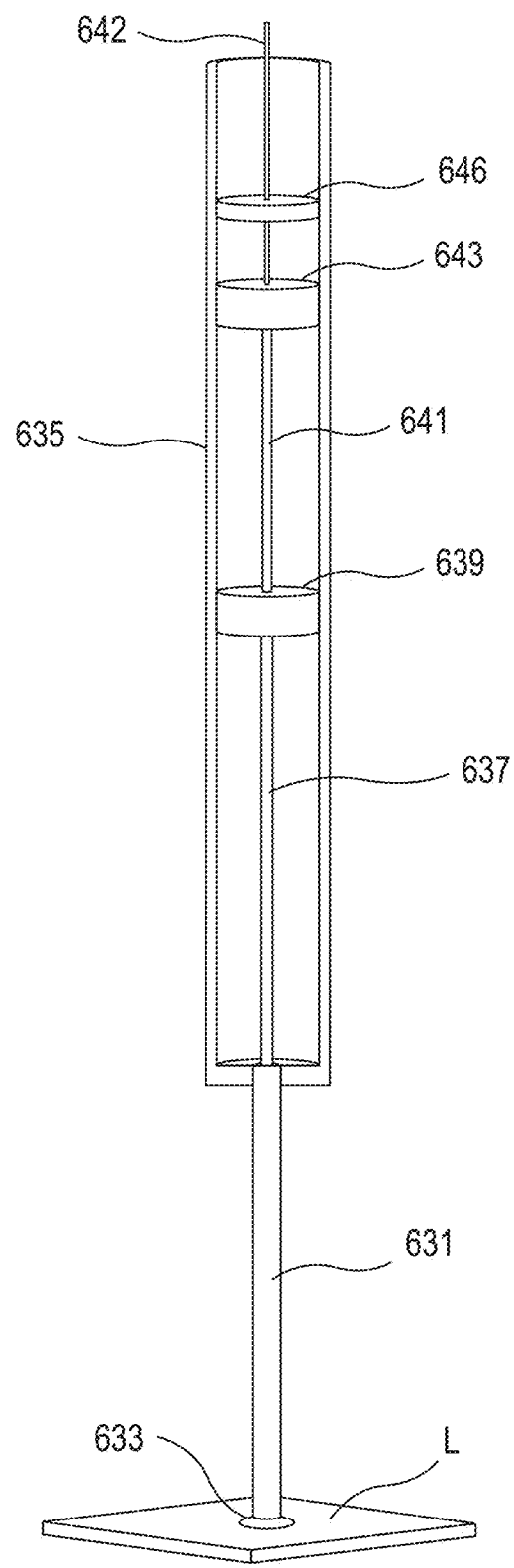
FIG. 29A is a schematic illustration of a side view of a distal anchor delivery device according to another embodiment, shown in a first configuration prior to deployment of a distal anchor through a mitral leaflet of a heart.

To deliver and form the distal anchor 640 within, for example, a left atrium of the heart to repair a mitral valve, the distal end portion of 632 of the delivery device 630 can be inserted through an apex portion of the heart and into the left ventricle until the end effector 633 contacts a proximal side of the mitral valve leaflet L as shown in FIG. 29A. In this embodiment, with the delivery device 630 positioned against only the ventricular side of the mitral leaflet L, and with a proximal end portion of the suture 642 (e.g., two suture strands of suture 642) secured to the suture catch 646, the actuator can be actuated and/or moved to move both the needle hub 643 and the needle 641 distally relative to the handle 635, the pusher hub 639 and the pusher 637. The needle hub 643 and the needle 641 (with the coiled portion of the suture 642 coupled thereto) are moved distally until the needle hub 643 and needle 641 reach a preset location within the handle 635, at which point their travel in the distal direction is stopped.

In some embodiments, the delivery device can also include one or more stop members within the handle that can engage or contact the needle hub to limit or stop the travel of the needle in the distal direction.

Figure 29B:
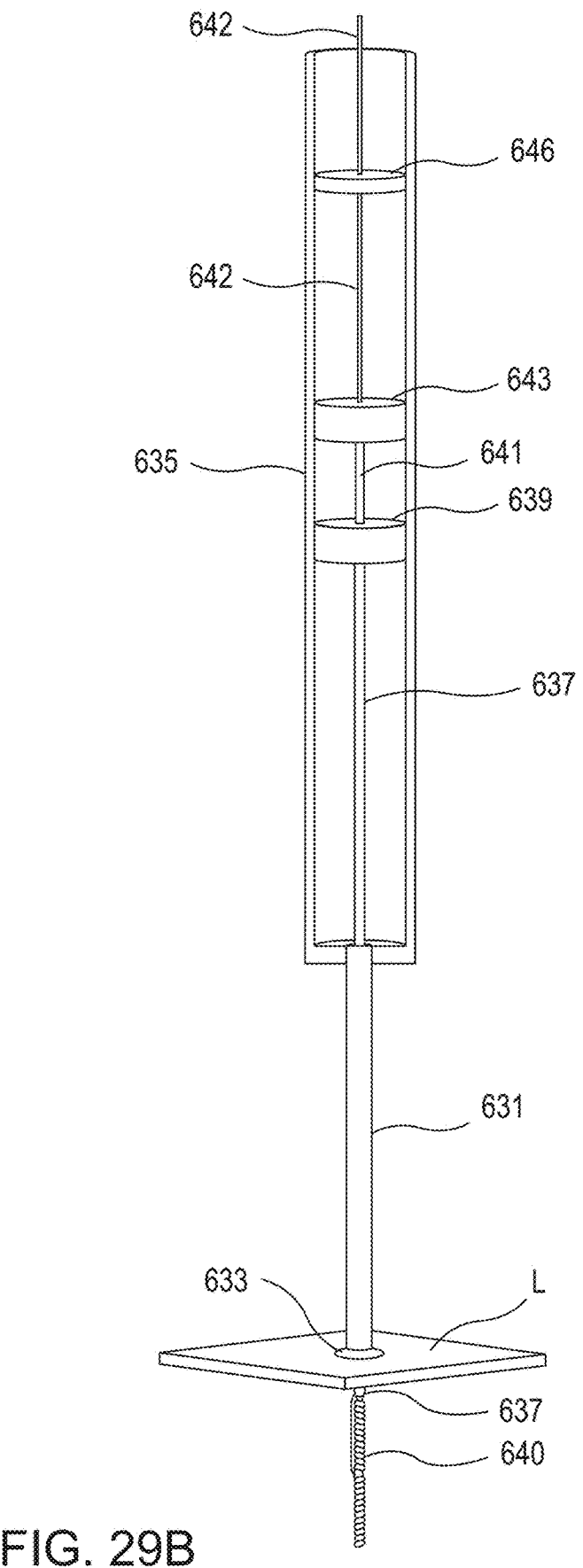
FIG. 29B is a schematic illustration of a side view of the distal anchor delivery device of FIG. 29A, shown in a second configuration during deployment of the distal anchor.

As the needle 641 is advanced distally within the handle 635, a distal piercing portion (not shown) of the needle 641, and in some cases, at least the first wrap of the coiled portion of the suture 642, punctures the leaflet L and forms an opening in the leaflet L (see e.g., FIG. 29B). The distance the distal piercing portion of the needle 641 extends within the left atrium on the distal side of the leaflet L can be determined, for example, by the preset allowed amount of travel of the needle 641 described above (e.g., in some embodiments, the amount of travel can be determined at least in part by a stop member within the handle and/or a mechanism disposed within the handle 635. In some embodiments, the delivery device 630 can be configured to advance the distal piercing portion of the needle 641 a shorter distance into the left atrium than as shown and described above for the embodiment of FIGS. 6-10. For example, in some embodiments, the needle hub 643 can travel about 0.25 inches. In some embodiments, the needle can be extended outside of the distal end of the delivery device (e.g., beyond the end effector) half the distance that is shown and described for the embodiment of FIGS. 6-10. In some embodiments, the needle can be extended outside the delivery device a distance of about 0.2-0.3 inches (e.g., 0.25 inches).

Figure 29C:
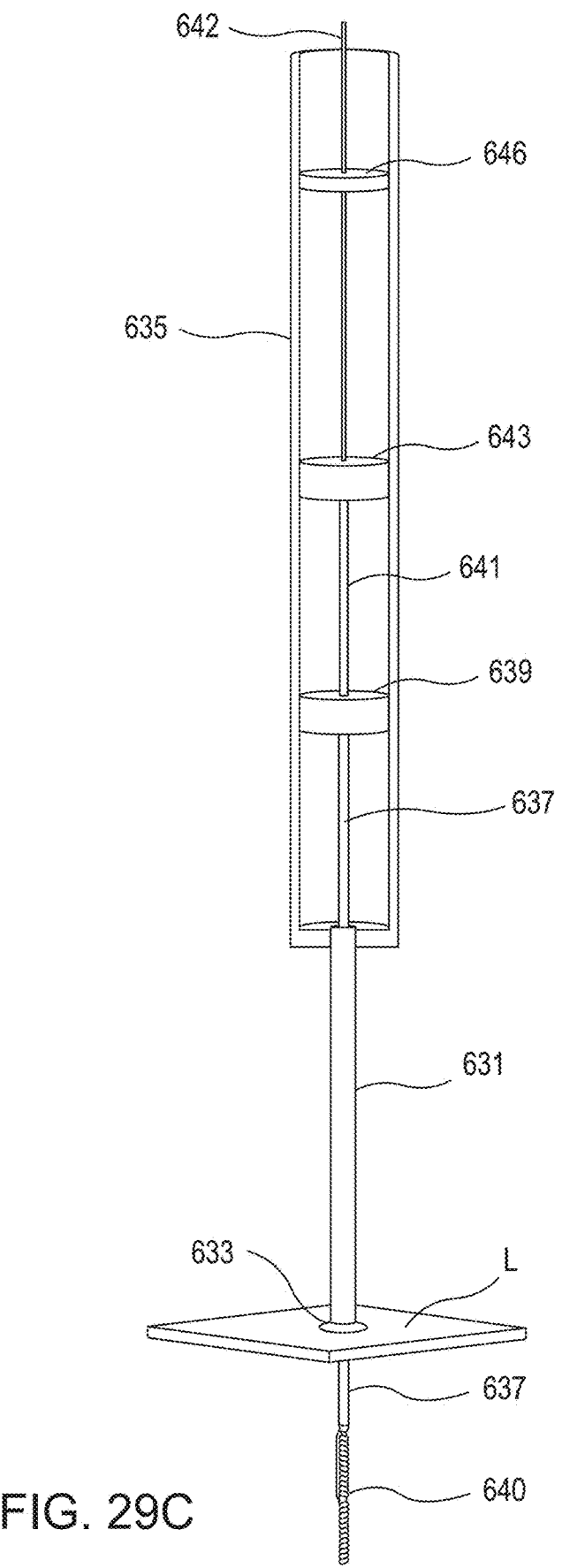
FIG. 29C is a schematic illustration of a side view of the distal anchor delivery device of FIG. 29A, shown in a third configuration during deployment of the distal anchor.

With a portion of the needle 641 disposed within the left atrium, an actuator (not shown) (e.g. a plunger or other type of actuator mechanism) can be actuated and/or moved to cause the pusher hub 639 and in turn the pusher 637 to move distally within the handle 635 and relative to the needle 641 and needle hub 643, as shown by FIG. 29C. In this manner, the pusher 637 can urge the coiled portion of the suture 642 (e.g., the distal anchor 640) further distally relative to the needle 641, as described in further detail herein. For example, in some embodiments, with the end effector 633 in contact with the proximal side of the mitral valve leaflet L, the pusher 637 can be moved distally about 0.65 inches.

Figure 29D:
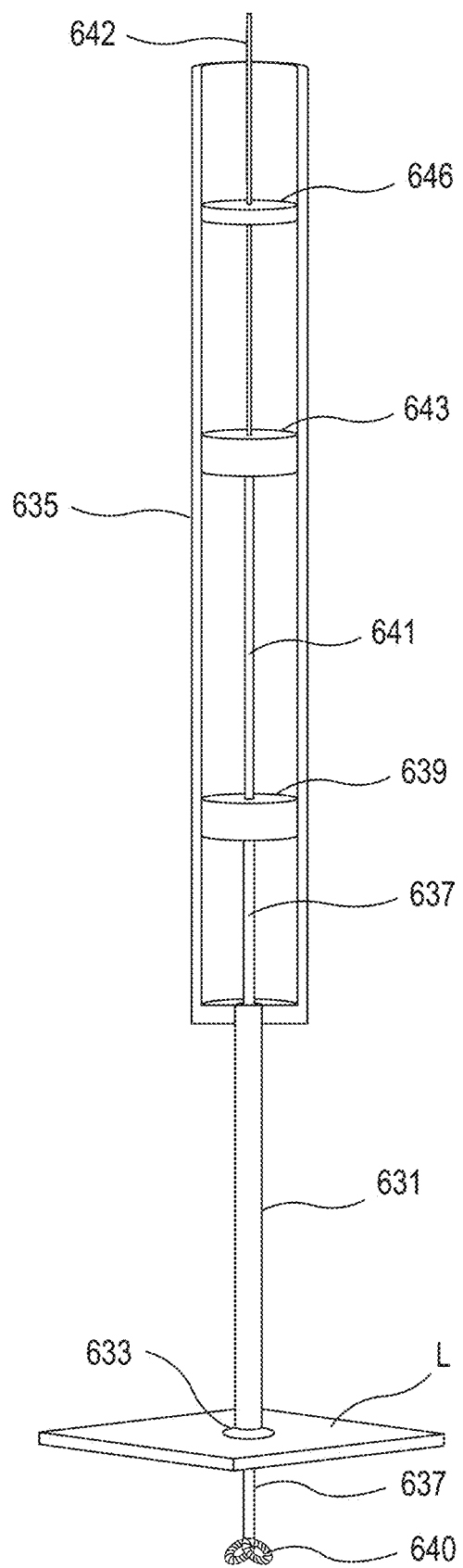
FIG. 29D is a schematic illustration of a side view of the distal anchor delivery device of FIG. 29A, shown in a fourth configuration during deployment of the distal anchor.

As the pusher 637 is moved distally, with the suture catch 646, the needle 641 and the needle hub 643 in fixed positions relative to the pusher 637, a distal end of the pusher 637 moves or pushes the distal coiled portion of the suture 642 (i.e., distal anchor 640) over the distal end of the needle 641 and further within the left atrium of the heart on a distal side of the mitral leaflet (see FIG. 29C). In this manner, the distal end of the pusher 637 pushes the coiled portion of the suture 642 (i.e., distal anchor 640) distally off the needle 641. To allow the distal coiled portion of the suture 642 (i.e., distal anchor 640) to slide relative to and eventually off the needle 641, when the suture 642 is loaded within the delivery device 630, there can be slack formed in the suture 642 between the distal coiled portion of the suture 642 and the suture lock within the suture catch 646. As shown in FIG. 29D, as the pusher 637 continues to move distally relative to the needle 641, the coiled portion of the suture 642 forms the bulky knot configuration of the distal anchor 640 by approximating opposite ends of the coils of the elongated coil portion of the suture 642 towards each other, to form one or more loops (two loops are shown in FIG. 29D). For example, with the opposite end portions of the suture 642 fixed and secured within the suture catch 646, as the pusher 637 moves distally, the coils are forced against the distal end of the pusher 637 to form the knot.

Figure 29E:
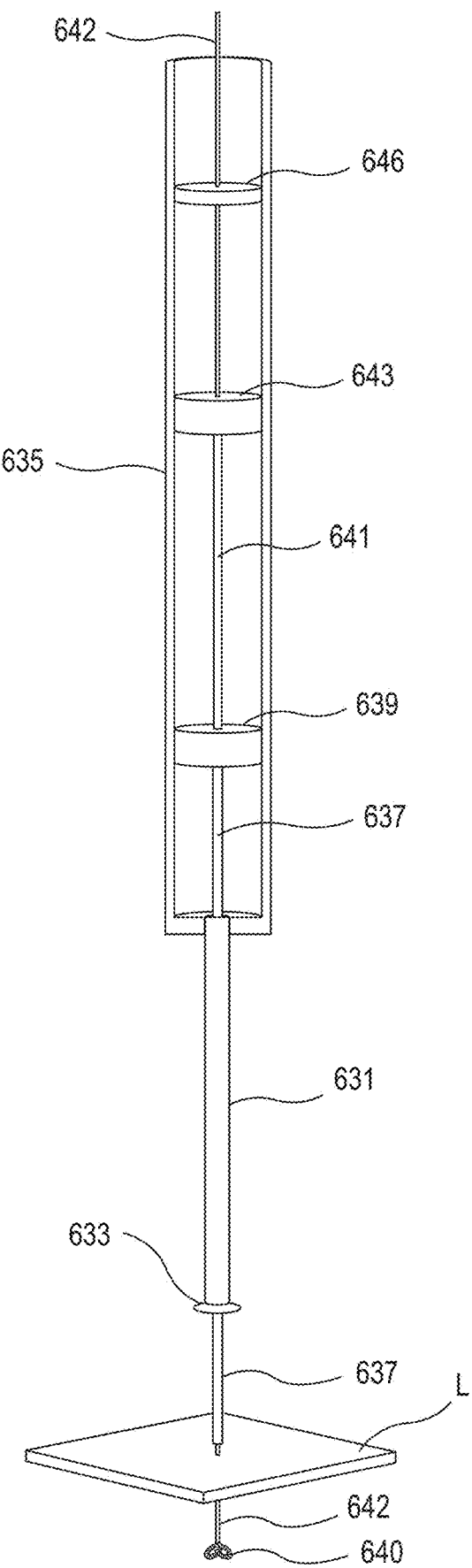
FIG. 29E is a schematic illustration of a side view of the distal anchor delivery device of FIG. 29A, shown in a fifth configuration as the delivery device is being retracted after deployment of the distal anchor.

After the distal anchor 640 has formed a knot, the proximal end portions of the suture 642 can be released from the suture catch 646 and the delivery device 630 can be withdrawn proximally, leaving the distal anchor 640 disposed on the distal side of the leaflet L (as shown in FIG. 29E), and two lengths or strands of the suture 632 extending out of the heart. In other words, with the suture 642 released from the suture catch 646, the delivery device 630 can be slid proximally over the suture 642 for removal. In some embodiments, after the distal anchor 640 has formed a knot, and the proximal end portions of the suture 642 are released from the suture catch 646, the needle 641 and/or the pusher 637 can be withdrawn proximally within and relative to the outer tube 631. In some instances, the needle 641 and/or the pusher 637 are withdrawn proximally into the outer tube 631 before the delivery device 630 is withdrawn proximally, while in other instances, the needle 641 and/or the pusher 637 are withdrawn proximally into the outer tube 631 as the delivery device 630 is withdrawn proximally.

As described above for previous embodiments, the lengths or strands of the suture 642 between the distal anchor 640 and the opening in the heart can be adjusted until the desired length is established. The proximal ends of the suture 642 can then be secured to an outer surface of the heart at, for example, the apex region, with a proximal anchor (not shown). The proximal anchor can be, for example, a pledget, one or more knots, or other suitable anchoring device. As previously described, the above procedure can be performed multiple times on the same leaflet, and/or can be performed on the other mitral valve leaflet in the same manner. Thus, as a result, one or more anchor-tether apparatuses (e.g., anchor-tether apparatus 145) can be anchored on a distal side of a leaflet with a distal anchor 640 and secured to the apex of the heart with a proximal anchor via the tether 642. Alternatively, if one or more anchor-tether apparatus are attached to both mitral valve leaflets, an anchor-tether apparatus attached to each leaflet can be secured together in the heart by tying them together with knots or by another suitable attachment member (not shown), creating an edge-to-edge repair to decrease the septal-lateral distance of the mitral valve orifice. The two attached anchor-tether apparatus can be left loose or tensioned to create a "facilitated" edge-to-edge repair before being secured to an outer surface of the heart with a proximal anchor.

In some embodiments, alternatively or in addition to providing slack in the suture, a spring can be disposed in the handle and coupled to the suture between the distal coiled portion of the suture (i.e., the distal anchor) and the suture lock, which can expand longitudinally as the distal anchor is moved distally relative to the handle as described above.

In another embodiment, a bulky knot distal anchor can be deployed/formed using a delivery device that utilizes an independent short throw deployment sequence. The independent short throw deployment sequence is similar to the independent full forward short throw deployment sequence of FIGS. 29A-29E, except the bulky knot distal anchor is deployed/formed by pulling on the proximal ends of the suture to pull the coils against the distal end of the pusher rather than moving the pusher distally relative to the needle. Similar to the embodiment of FIGS. 29A-29E, for example, the pusher and needle can be moved within the outer tube independently of each other and during varying time periods in response to separate force-providing mechanisms and/or separate energy storage members. Further, similar to the embodiment of FIGS. 14A-14E, the needle can be moved proximally within and relative to the handle, pulling the suture (e.g., suture strands extending from the coiled portion of the suture) proximally through the pusher to form the bulky knot configuration of the distal anchor. FIGS. 30A-30E are schematic illustrations of an embodiment of a delivery device for delivering and deploying a distal anchor and configured to provide such an independent short throw deployment sequence.

As shown in FIGS. 30A-30E, a delivery device 730 includes a distal end portion 732, a proximal end portion 736 and a medial portion 734. The distal end portion 732 includes an end effector 733 that can be placed in contact with a leaflet L of a mitral valve as described above with respect to previous embodiments. The end effector 733 is coupled to a distal end portion of an outer tube 731 and a proximal end portion of the outer tube 731 is coupled to a handle 735 at the proximal end portion 736 of the delivery device 730. The end effector 733 can distribute the force of the outer tube 731 over a larger area to prevent/eliminate puncturing of the leaflet with the delivery device 730 during deployment. In some embodiments, the end effector 733 can include a balloon (not shown). An elongate pusher 737 is movably disposed within a lumen of the outer tube 731 and is coupled to a pusher hub 739 that is movably disposed within the handle 735 and coupled to an actuator (not shown) and/or energy storage member (not shown). The actuator and/or energy storage member can be used to actuate or move the pusher hub 739 and the pusher 737 during deployment of a distal anchor 740 and can be movably disposed at least partially within the handle. A needle 741 (see FIG. 30B) is movably disposed within a lumen of the pusher 737 and is coupled to a needle hub 743 that is coupled to an actuator (not shown). The actuator can be used to actuate or move the needle hub 743 and the needle 741 (both independent of the pusher hub and the pusher) during deployment of the distal anchor 740 and can be movably disposed at least partially within the handle 735. For example, the handle 735 defines a lumen in which the actuator or a portion of the actuator can be actuated and/or moved. The delivery device 730 can also include a locking lever (not shown) that can be used to prevent the actuator and/or one or more of its constituent components from actuating and/or moving within or relative to the handle 735 during storage and prior to performing a procedure or a particular portion thereof to deploy the distal anchor. For example, the locking lever can be similar to or the same as the locking lever 449 described above.

A suture catch 746 (also referred to as "tether catch") can be coupled to a proximal end of the delivery device 730. The suture catch 746 is configured to releasably hold or secure a suture 742 extending through the delivery device 730 during delivery of the distal anchor 740 as described above for previous embodiments. In some embodiments, the suture catch 746 can hold the suture 742 with a friction fit or with a clamping force and can have a lock that can be released after the distal anchor 740 has been deployed/formed into a bulky knot.

As described above for previous embodiments, the suture 742 (also referred to herein as "tether") can be formed into an elongated coiled configuration and is disposed within the outer tube 731 at the distal end portion 732 of the delivery device 730. As described above, for example, for suture 242, two strands of the suture 742 can extend from the distal elongated coiled portion of the suture 742, and extend through the lumen of the needle 741. The distal elongated coiled portion of the suture 742 will be formed into the distal anchor 740 (e.g., bulky knot) upon actuation of the delivery device 730 as described in more detail below. As discussed above for previous embodiments, the distal anchor 740 can be in the form of one or more multi-turn coils of the suture 742 that can be changed from the elongated coiled configuration during delivery to a knot configuration by approximating opposite ends of the coils towards each other, to form one or more loops.

Figure 30A:
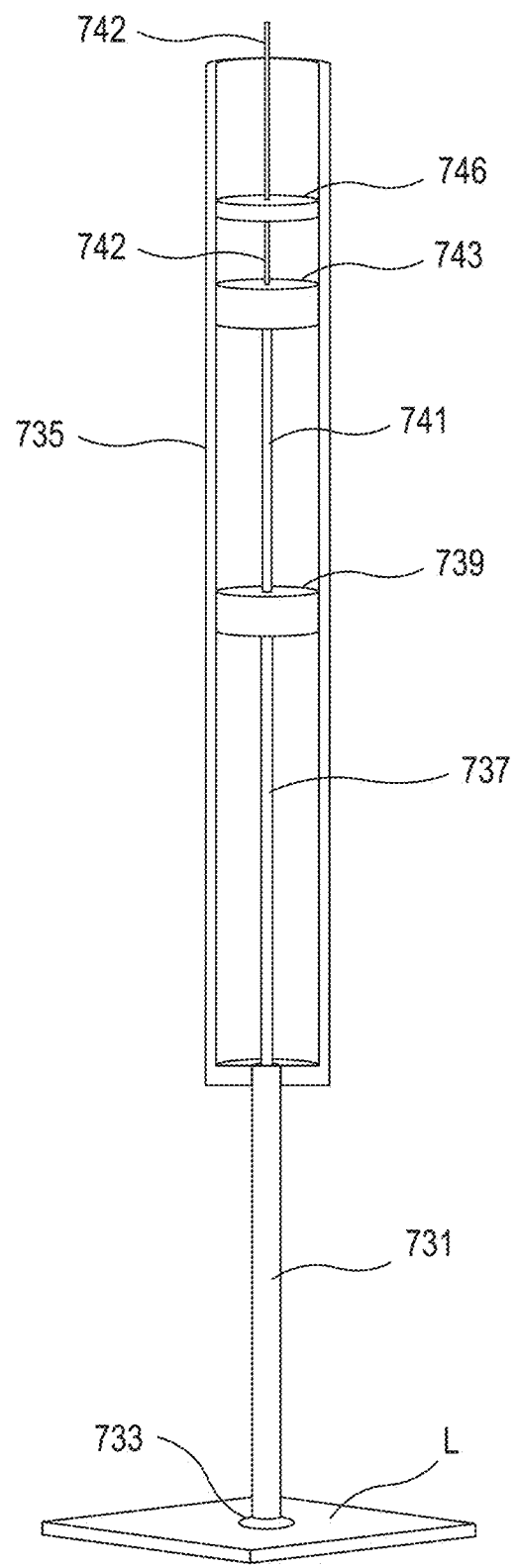
FIG. 30A is a schematic illustration of a side view of a distal anchor delivery device according to another embodiment, shown in a first configuration prior to deployment of a distal anchor through a mitral leaflet of a heart.

To deliver and form the distal anchor 740 within, for example, a left atrium of the heart to repair a mitral valve, the distal end portion of 732 of the delivery device 730 can be inserted through an apex portion of the heart and into the left ventricle until the end effector 733 contacts a proximal side of the mitral valve leaflet L as shown in FIG. 30A. In this embodiment, with the delivery device 730 positioned against only the ventricular side of the mitral leaflet L, and with a proximal end portion of the suture 742 (e.g., two suture strands of suture 742) secured to the suture catch 746, the actuator and/or energy storage member can be actuated and/or moved to move both the needle hub 743 and the needle 741 distally relative to the handle 735, the pusher hub 739 and the pusher 737. The needle hub 743 and the needle 741 (with the coiled portion of the suture 742 coupled thereto) are moved distally until the needle hub 743 and needle 741 reach a preset location within the handle 735, at which point their travel in the distal direction is stopped.

In some embodiments, the delivery device can also include one or more stop members within the handle that can engage or contact the needle hub to limit or stop the travel of the needle in the distal direction.

Figure 30B:
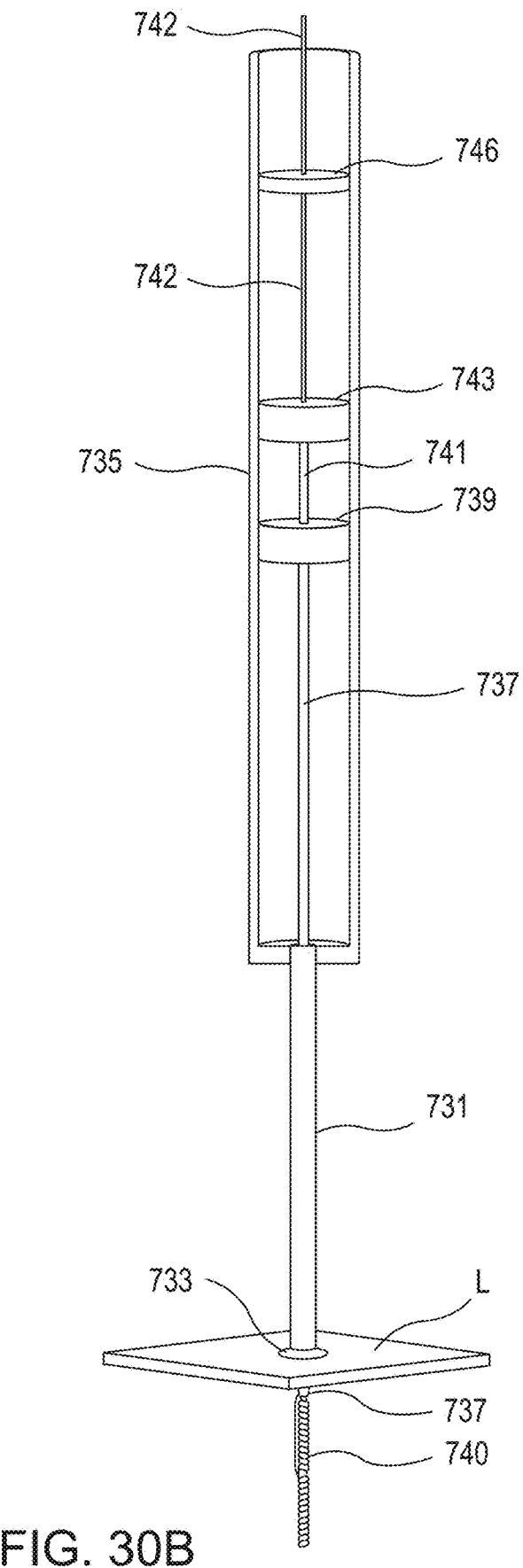
FIG. 30B is a schematic illustration of a side view of the distal anchor delivery device of FIG. 30A, shown in a second configuration during deployment of the distal anchor.

As the needle 741 is advanced distally within the handle 735, a distal piercing portion (not shown) of the needle 741, and in some cases, at least the first wrap of the coiled portion of the suture 742, punctures the leaflet L and forms an opening in the leaflet L (see e.g., FIG. 30B). The distance the distal piercing portion of the needle 741 extends within the left atrium on the distal side of the leaflet L can be determined, for example, by the preset allowed amount of travel of the needle 741 described above (e.g., in some embodiments, the amount of travel can be determined at least in part by a stop member within the handle and/or a mechanism disposed within the handle 735). In some embodiments, the delivery device 730 can be configured to advance the distal piercing portion of the needle 741 a shorter distance into the left atrium than as shown and described above for the embodiment of FIGS. 6-10. For example, in some embodiments, the needle hub 743 can travel about 0.25 inches. In some embodiments, the needle can be extended outside of the distal end of the delivery device (e.g., beyond the end effector) half the distance that is shown and described for the embodiment of FIGS. 6-10. In some embodiments, the needle can be extended outside the delivery device a distance of about 0.2-0.3 inches (e.g., 0.25 inches).

Figure 30C:
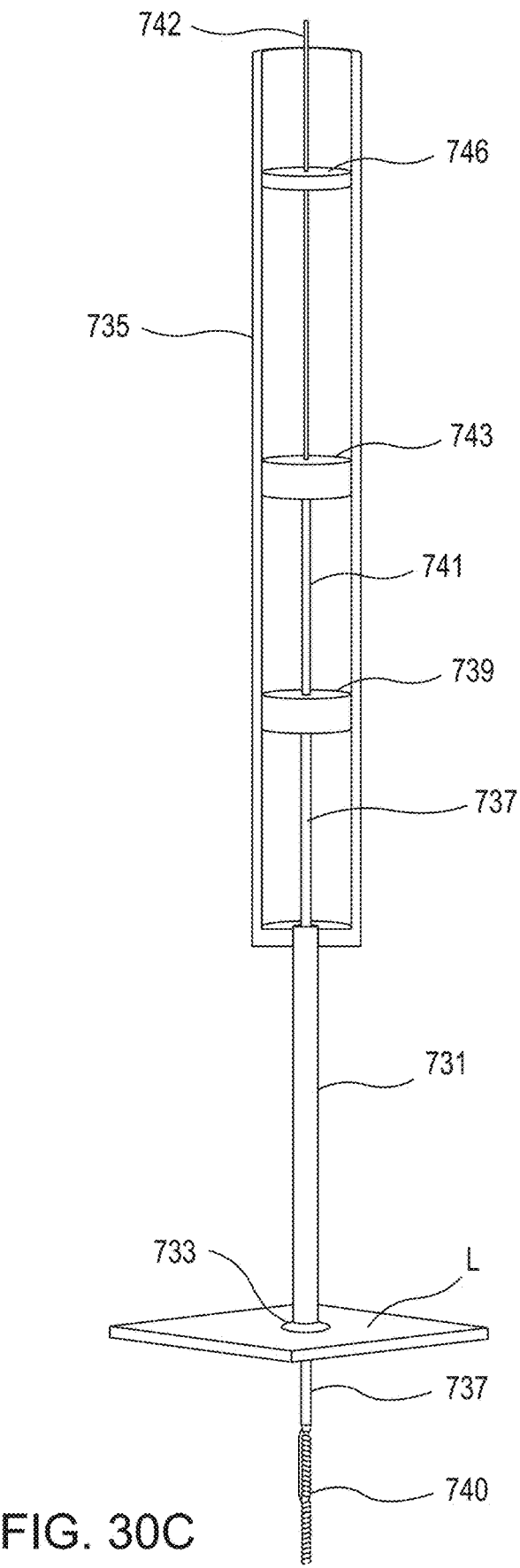
FIG. 30C is a schematic illustration of a side view of the distal anchor delivery device of FIG. 30A, shown in a third configuration during deployment of the distal anchor.

With a portion of the needle 741 disposed within the left atrium, an actuator (not shown) can be actuated and/or moved to cause the pusher hub 739 and in turn the pusher 737 to move distally within the handle 735 and relative to the needle 741 and needle hub 743, as shown by FIG. 30C. In this manner, the distal end portion of the pusher 737 can urge, push, or otherwise move the coiled portion of the suture 742 (e.g., the distal anchor 740) off and distal to the needle 741, as described in further detail herein. For example, in some embodiments, with the end effector 733 in contact with the proximal side of the mitral valve leaflet L, and the needle 741 in a fixed position relative to the pusher 737, the pusher 737 can be moved distally about 0.65 inches.

As the pusher 737 is moved distally, and with the suture catch 746, the needle 741 and the needle hub 743 in fixed positions relative to the pusher 737, a distal end of the pusher 737 moves or pushes the distal coiled portion of the suture 742 (i.e., distal anchor 740) over the distal end of the needle 741 and further within the left atrium of the heart on a distal side of the mitral leaflet (see FIG. 30C). In other words, the distal end of the pusher 737 and the distal coiled portion of the suture 742 extend beyond the distal end of the needle 741. For example, in some embodiments, at least half a length of the distal coiled portion of the suture 742 extends beyond the distal end of the needle 741. In some embodiments, at least three quarters of the length of the distal coiled portion of the suture 742 extends beyond the distal end of the needle 741. In other embodiments, the entire length of the distal coiled portion of the suture 742 extends beyond the distal end of the needle 741. To allow the distal coiled portion of the suture 742 (i.e., distal anchor 740) to slide relative to and eventually off the needle 741, when the suture 742 is loaded within the delivery device 730, there can be slack formed in the suture 742 between the distal coiled portion of the suture 742 and the suture lock within the suture catch 746.

Figure 30D:
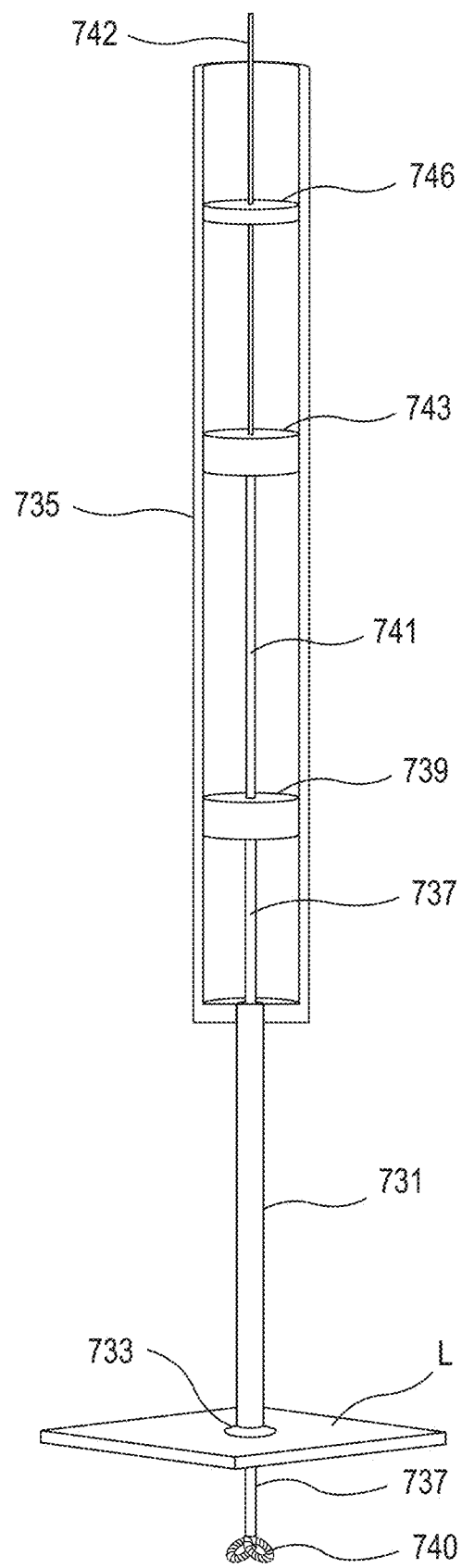
FIG. 30D is a schematic illustration of a side view of the distal anchor delivery device of FIG. 30A, shown in a fourth configuration during deployment of the distal anchor.
Figure 30E:
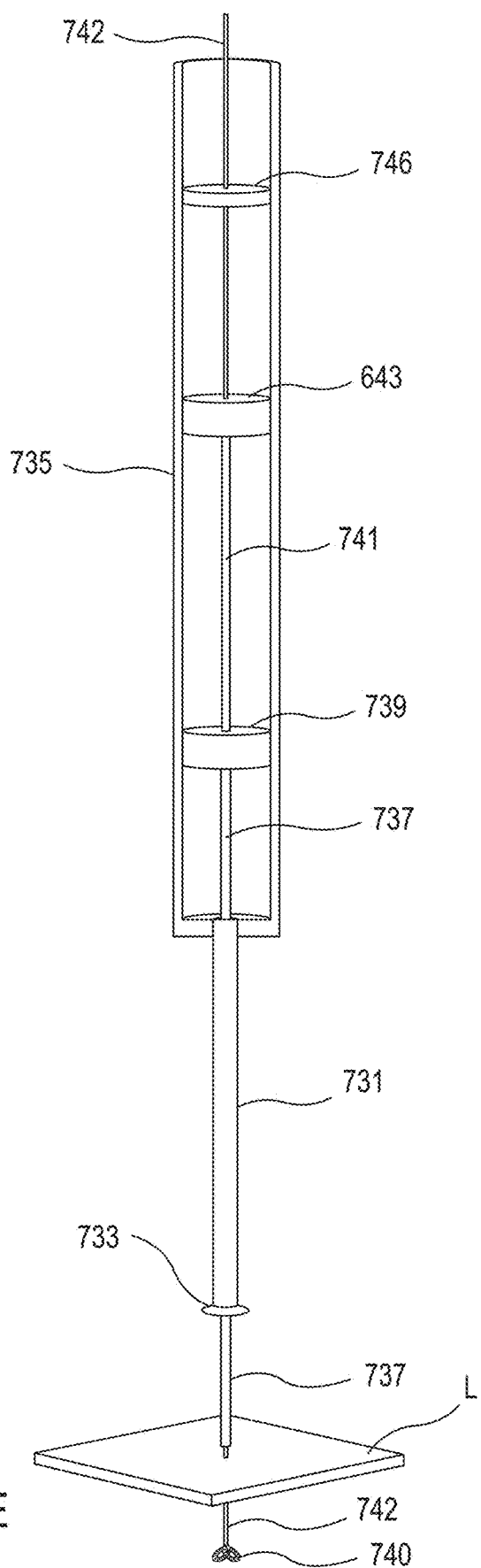
FIG. 30E is a schematic illustration of a side view of the distal anchor delivery device of FIG. 30A, shown in a fifth configuration as the delivery device is being retracted after deployment of the distal anchor.

After the distal coiled portion of the suture 742 is moved to the distal side of the leaflet L, the needle hub 743 and the needle 741 are moved proximally relative to the pusher 737, pulling the suture 742 (e.g., suture strands extending from the coiled portion of the suture 742) through the pusher 737 to form the bulky knot configuration (as shown in FIG. 30D) of the distal anchor 740 by approximating opposite ends of the coils of the elongated coil portion of the suture 742 towards each other, to form one or more loops. As shown in FIG. 30D, by pulling on the proximal ends of the suture 742, the coils are pulled against the distal end of the pusher 737 to form the knot. After the distal anchor 740 has formed a knot, the proximal end portions of the suture 742 can be released from the suture catch 746 and the delivery device 730 can be withdrawn proximally, leaving the distal anchor 740 disposed on the distal side of the leaflet L (as shown in FIG. 30E), and two lengths or strands of the suture 732 extending out of the heart. In other words, with the suture 742 released from the suture catch 746, the delivery device 730 can be slid over the suture 742 for removal.

In some embodiments, after the distal anchor 740 has formed a knot, and the proximal end portions of the suture 742 are released from the suture catch 746, the needle 741 and/or the pusher 737 can be withdrawn proximally within and relative to the outer tube 731. In some instances, the needle 741 and/or the pusher 737 are withdrawn proximally into the outer tube 731 before the delivery device 730 is withdrawn proximally, while in other instances, the needle 741 and/or the pusher 737 are withdrawn proximally into the outer tube 731 as the delivery device 730 is withdrawn proximally.

As described above for previous embodiments, the lengths or strands of the suture 742 between the distal anchor 740 and the opening in the heart can be adjusted until the desired length is established. The proximal ends of the suture 742 can then be secured to an outer surface of the heart at, for example, the apex region, with a proximal anchor (not shown). The proximal anchor can be, for example, a pledget, one or more knots, or other suitable anchoring device. As previously described, the above procedure can be performed multiple times on the same leaflet, and/or can be performed on the other mitral valve leaflet in the same manner. As a result, one or more anchor-tether apparatuses (e.g., anchor-tether apparatus 145) as described above are each anchored on a distal side of a leaflet with a distal anchor 740 and secured to the apex of the heart with a proximal anchor via the tether 742. Alternatively, if one or more anchor-tether apparatus are attached to both mitral valve leaflets, an anchor-tether apparatus attached to each leaflet can be secured together in the heart by tying them together with knots or by another suitable attachment member (not shown), creating an edge-to-edge repair to decrease the septal-lateral distance of the mitral valve orifice. The two attached anchor-tether apparatus can be left loose or tensioned to create a "facilitated" edge-to-edge repair before being secured to an outer surface of the heart with a proximal anchor.

In some embodiments, alternatively or in addition to providing slack in the suture, a spring can be disposed in the handle and coupled to the suture between the distal coiled portion of the suture (i.e., the distal anchor) and the suture lock, which can expand longitudinally as the distal anchor is moved distally relative to the handle as described above.

Figure 31:
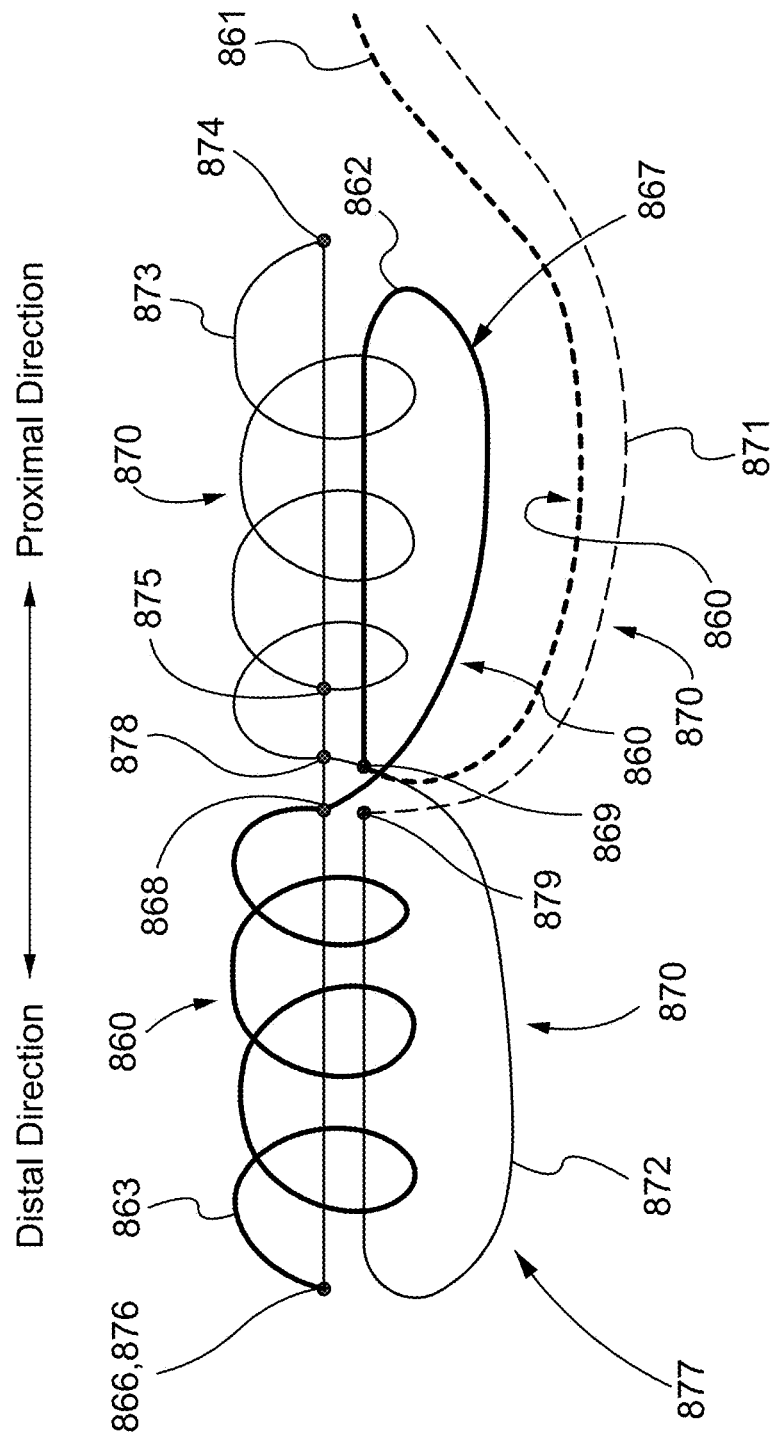
FIG. 31 is a schematic illustration of a distal anchor shown in an elongated configuration, according to an embodiment.

FIG. 31 shows a schematic illustration of a distal anchor 840 shown in an elongated coiled configuration. The distal anchor 840 can be delivered and deployed within a heart using any of the delivery devices described herein. For ease of explanation, the distal anchor 840 is shown and described with reference to a first section 860 of the suture 842 and a second section 870 of the suture 842. The first section 860 has a first portion 861 (as shown in dashed line for ease of illustration) and a second portion 862 including a first coil 863 formed of multiple turns about the exterior of the distal end portion 832 of the delivery device 830. The first coil 863 has a proximal end 864 and a distal end 865. The second portion 862 of the first section 860 has a first end 866 at the distal end 865 of the first coil 863.

The second section 870 has a second portion 872 with a first end 876, and extends proximally from the first end 866 of the first section 860 through an interior of the first coil 863 (and through the lumen of the distal end portion 832 of the deliver device 830) to the proximal end 864 of the first coil 863. The second section 870 also includes a loop forming segment 877 that extends distally from a first end 878 of the loop forming segment 877 at the proximal end 864 of the first coil 863 along the outside of the first coil 863 to the distal end 865 of the first coil 863, and extends proximally through the interior of the first coil 863 (and through the lumen of the distal end portion 832 of the deliver device 830) to the proximal end 864 of the first coil 863 at a second end 879 of the loop forming segment 877.

The second portion 872 of the second section 870 includes a second coil 873 formed of multiple turns about the exterior of the distal end portion 832 of the delivery device 830 proximal to the first coil 863, and has a proximal end 874 and a distal end 875. The second portion 872 of the second section 870 extends proximally from the first end 876 of the second portion 872 through the interior of the second coil 873 (and as shown in FIGS. 32A-32E, e.g., through the lumen of the distal end portion 832 of the deliver device 830) to the proximal end 874 of the second coil 873. The first end 878 of the loop forming segment 877 of the second portion 872 of the second section 870 extends from the distal end 875 of the second coil 873.

The second portion 862 of the first section 860 has a loop forming segment 867 that extends from a first end 868 of the loop forming segment 867 of the second portion 862 of the first section 860 proximally from the proximal end 864 of the first coil 863 along the outside of the second coil 873 to the proximal end 874 of the second coil 873 and extends distally through the interior of the second coil 873 (and as shown in FIGS. 32A-32E, e.g., through the lumen of the distal end portion 832 of the delivery device 830) to the distal end 875 of the second coil 873 at a second end 869 of the loop forming segment 867 of the second portion 862 of the first section 860. The first portion 861 of the first section 860 extends proximally from the second end 869 of the loop forming segment 867 of the second portion 862 of the first section 860.

FIGS. 32A-32E illustrate in sequence the formation of the distal anchor 840 of FIG. 31 about an exterior of a needle 841 of a delivery device (not shown) and in an elongated coiled configuration (FIG. 32E). The needle 841 defines a lumen L therethrough and a slot (not shown) in communication with the lumen L. To form the distal anchor 840 about the needle 841, the second portion 872 of the second section 870 of the suture 842 is routed through the lumen L of the needle 841 (see e.g., FIG. 32A). Next, the second portion 862 of the first section 860 of the suture 842 is wrapped about the needle 841 to form the first coil 863 (see e.g., FIG. 32B). Similarly, the second portion 872 of the second section 870 of the suture 842 is wrapped about the needle 841 proximate to the first coil 863 to form the second coil 873 (see e.g., FIG. 32C).

After formation of the first coil 863 and the second coil 873 about the needle 841, the loop forming segment 867 of the second portion 862 of the first section 860 is formed by routing proximally the section portion 862 of the first section 860 of the suture 842 from the proximal end 864 of and exterior to the first coil 863 towards the proximal end 874 of the second coil 873 (see e.g., FIG. 32C), and then extending distally through the interior of the second coil (see e.g., FIG. 32D). In a similar manner, the loop forming segment 877 of the second portion 872 of the second section 870 is formed by routing distally the second portion 872 of the second section 870 of the suture 842 from the distal end 875 of the second coil 873 towards the distal end 865 of the first coil 863 (see e.g., FIG. 32C), and then extending proximally through the interior of the first coil 863 to the proximal end 864 of the first coil 863 (see e.g., FIG. 32D). The first portion 861 of the first section 860 of the suture 842 and the first portion 871 (as shown in dashed line for ease of illustration) of the second section 870 of the suture 842 extends from the lumen L of the needle 841 through the slot (not shown) of the needle 841 to an area external to the needle 841 such that each portion 861, 871 can be manipulated (e.g., pulled proximally) to form the knot, as described above.

FIGS. 33A-33D illustrate an example method of preparing a delivery device 930 to deliver a distal anchor 940 (e.g., and to form a bulky knot distal anchor) to be disposed on a distal side of a mitral valve leaflet. The delivery device 930 can be constructed the same as or similar to, and function the same as or similar to, for example, the delivery device 430 or any other delivery device described herein. It should be understood that for features and functions not specifically discussed with respect to the delivery device 930, those features and functions can be the same as or similar to the delivery device 430 or any of the delivery devices described herein.

Figure 33A:
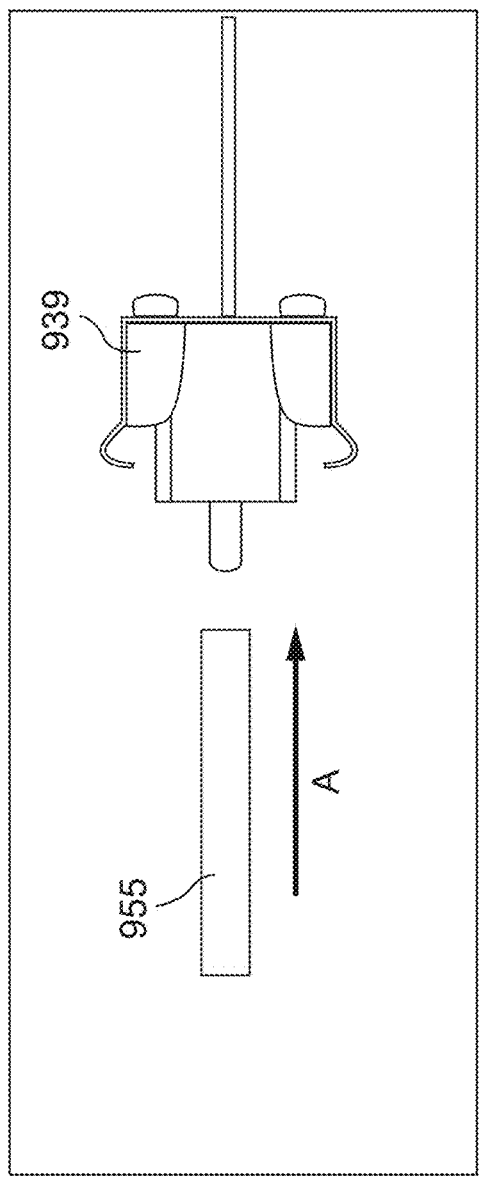
Figure 33B:
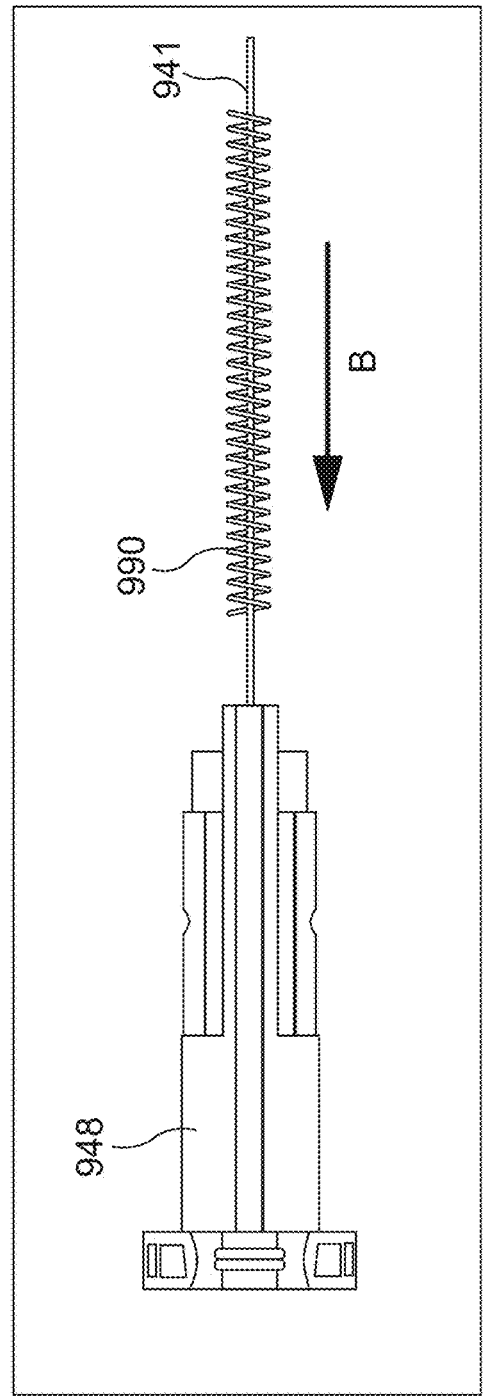

The guide member 955 is configured to be coupled to the proximal end of a pusher hub 939 as illustrated by arrow A in FIG. 33A and disposed within a lumen defined by the biasing member 990 shown in FIG. 30B. As illustrated in FIG. 33B, the biasing member 990 is configured to be slid over the needle 941 that is coupled to a needle hub (not shown) disposed within a plunger 948.

To couple the pusher hub 939 to the plunger 948, the pusher hub 939 is slid over the needle 941 towards the distal end of the plunger 948, as shown by arrow B in FIG. 33C, until the guide member 955 and the biasing member 990 are inserted into a lumen defined by the plunger 948 and the tabs 985 of the pusher hub 939 are aligned with corresponding slots (not shown) defined by the plunger 948. As the pusher hub 939 is slid towards and eventually coupled to the plunger 948, the biasing member 990 is compressed or otherwise loaded with potential energy. Although not shown in FIGS. 33A-33D, the delivery device 930 can include a handle, and similar to as described herein with respect to the tabs 485 and the handle 435 of FIGS. 17A and 18A, when the pusher hub 939 is coupled to the plunger 948 (as shown by FIG. 33D), the tabs are compressed by the inner walls of the handle. As illustrated in detailed view by FIG. 33E, the needle 941 is movably disposed within the lumen defined by the pusher 937.

Figure 34A:
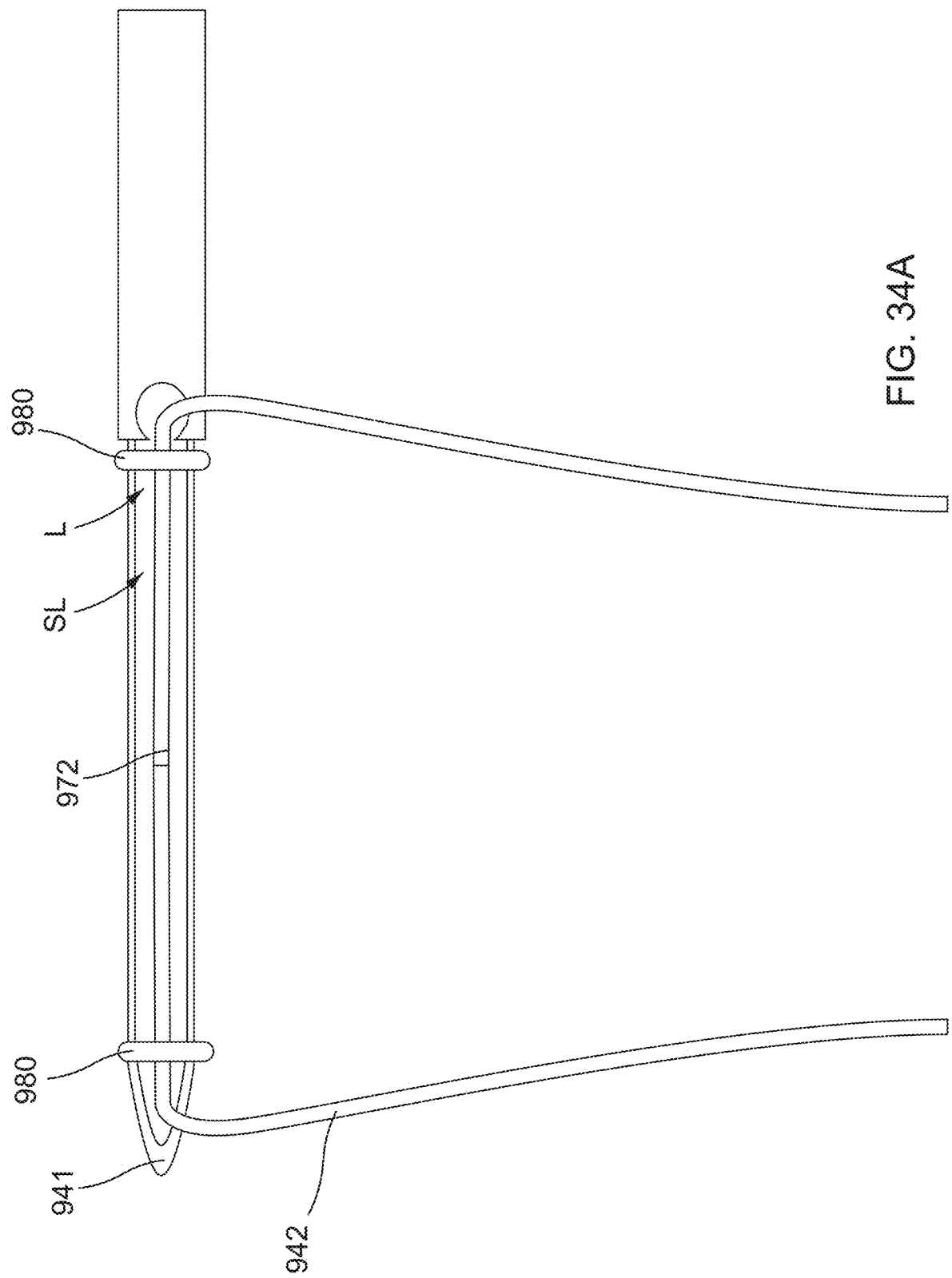

FIGS. 34A-34H illustrate an example method of forming the distal anchor 940 in an elongated coiled configuration (FIG. 34H) about an exterior of the needle 941. The distal anchor 940 (formed of a suture 942) and the needle 941 can be constructed similar to or the same as and function similar to or the same as any of the distal anchors and needles described herein with respect to previous embodiments. The needle 941 defines an interior lumen L, and a distal portion of the needle 941 includes a slot SL in communication with the lumen. As shown in FIG. 34A, the second portion 972 of the second section 970 of the suture 942 is routed through the slot SL of the needle 941 and between the knot rings 980. The knot rings 980 (e.g., silicone O-rings) are disposed about the suture 942 and the needle 941 to secure the suture 942 to and within the slot SL of the needle 941. In this manner, the knot rings 980 define the outer edges (or the distal end 965 of the first coil 963 and the proximal end 974 of the second coil 973) of the distal anchor 940, and can secure the suture 942 such that the first coil 963 and the second coil 973 can be formed about the needle 941.

Figure 34B:
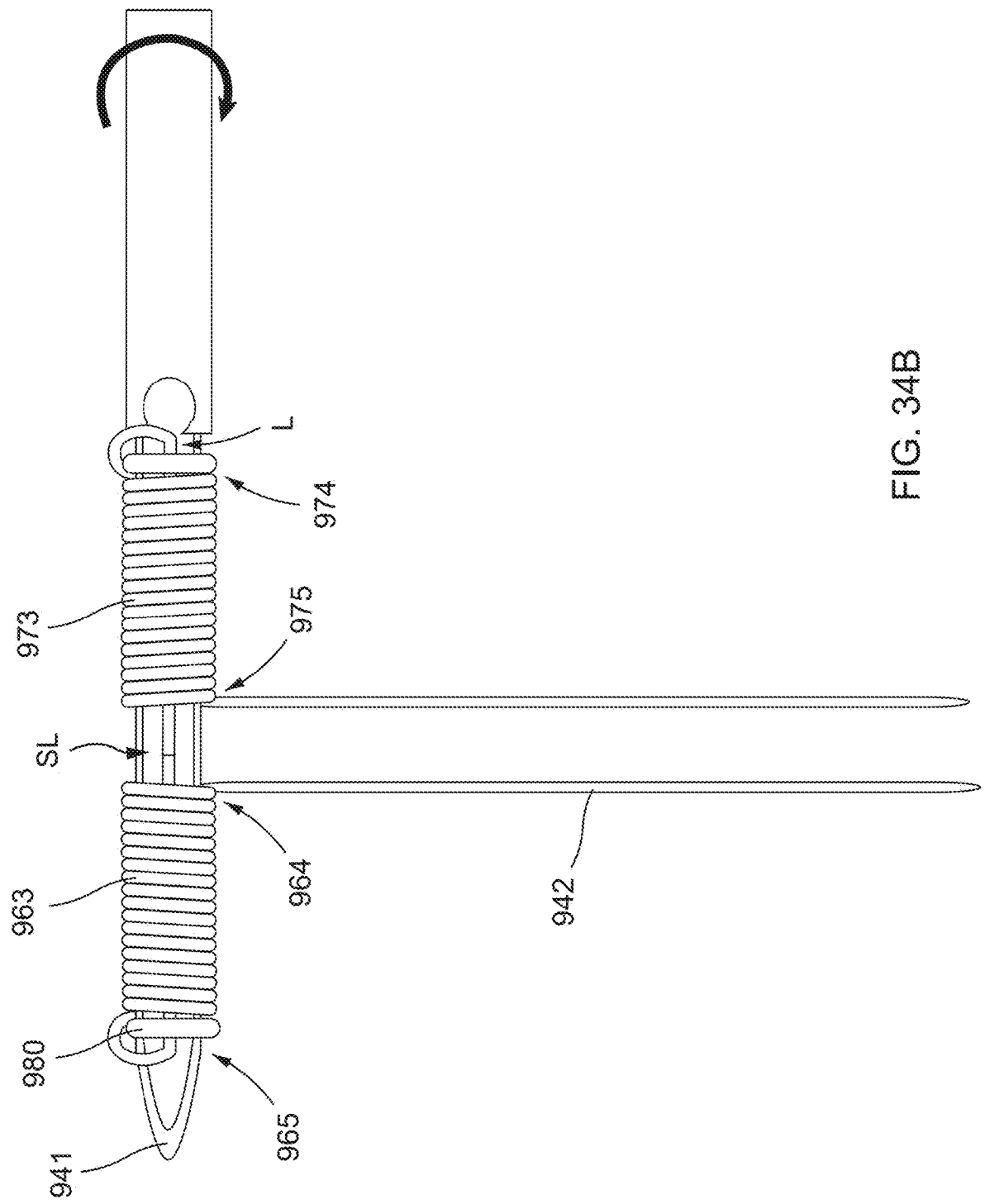

To form the first coil 963 and the second coil 973, the needle 941 is rotated such that the free ends (or the second portion 962 of the first section 960 and the second portion 972 of the second section 970) of the suture 942 form multiple turns about the exterior of the needle 941, as shown in FIG. 34B. Next, the loop forming segment 967 of the second portion 962 of the first section 960 is formed by routing proximally the second portion 962 of the first section 960 of the suture 942 from the proximal end 964 of and exterior to the first coil 963 towards the proximal end 974 of the second coil 973, and then extending distally through the interior of the second coil 973 to the distal end 975 of the second coil 973, as shown in FIG. 34C. In a similar manner, the loop forming segment 977 of the second portion 972 of the second section 970 is formed by routing distally the second portion 972 of the second section 970 of the suture 942 from the distal end 975 of the second coil 973 towards the distal end 965 of the first coil 963, and then extending proximally through the interior of the first coil 963 to the proximal end 964 of the first coil 963, as shown in FIG. 34D.

To further prepare the distal anchor 940 for delivery to a heart, as described in previous embodiments, the loop forming segments can be shortened and/or tightened by pulling the first portion 961 of the first section 960 of the suture 942 and the first portion 971 of the second section 970 of the suture 942. Such a configuration is shown in FIG. 34E. Once the loop forming segments 967, 977 are formed, the knot rings 980 can be removed from the needle 932 and the suture 942. Upon removal of the knot rings 980, the loop forming segments 967, 977 can be further shortened or tightened, as shown in FIGS. 34F and 34G. Next, the first portion 961 of the first section 960 of the suture 942 and the first portion 971 of the second section 970 of the suture 942 can be routed proximally into a distal end of the interior lumen L of the needle 941 and proximally through the interior lumen L, as shown in FIGS. 34G and 34H.

Figure 34D:
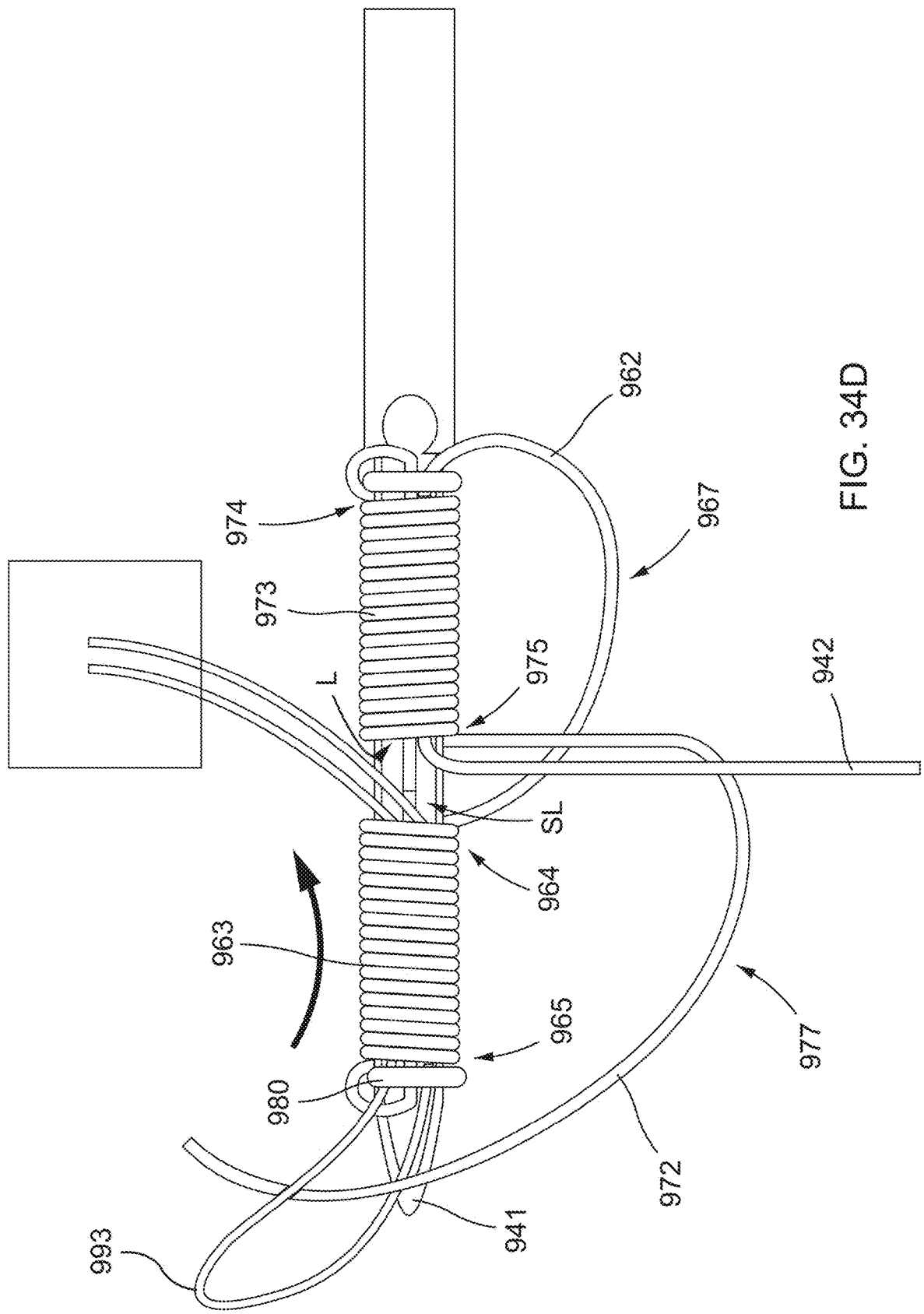
Figure 34E:
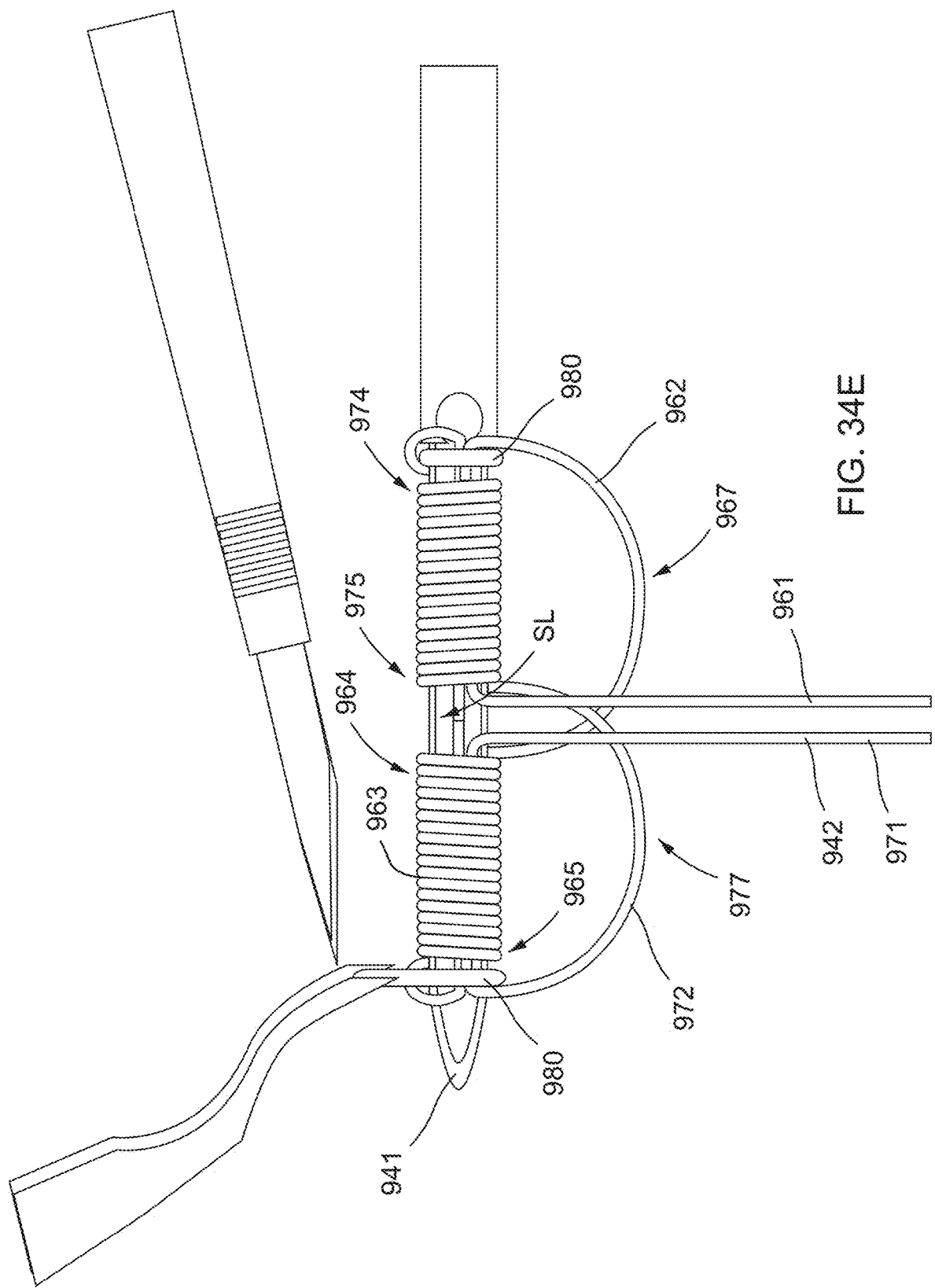
Figure 34F:
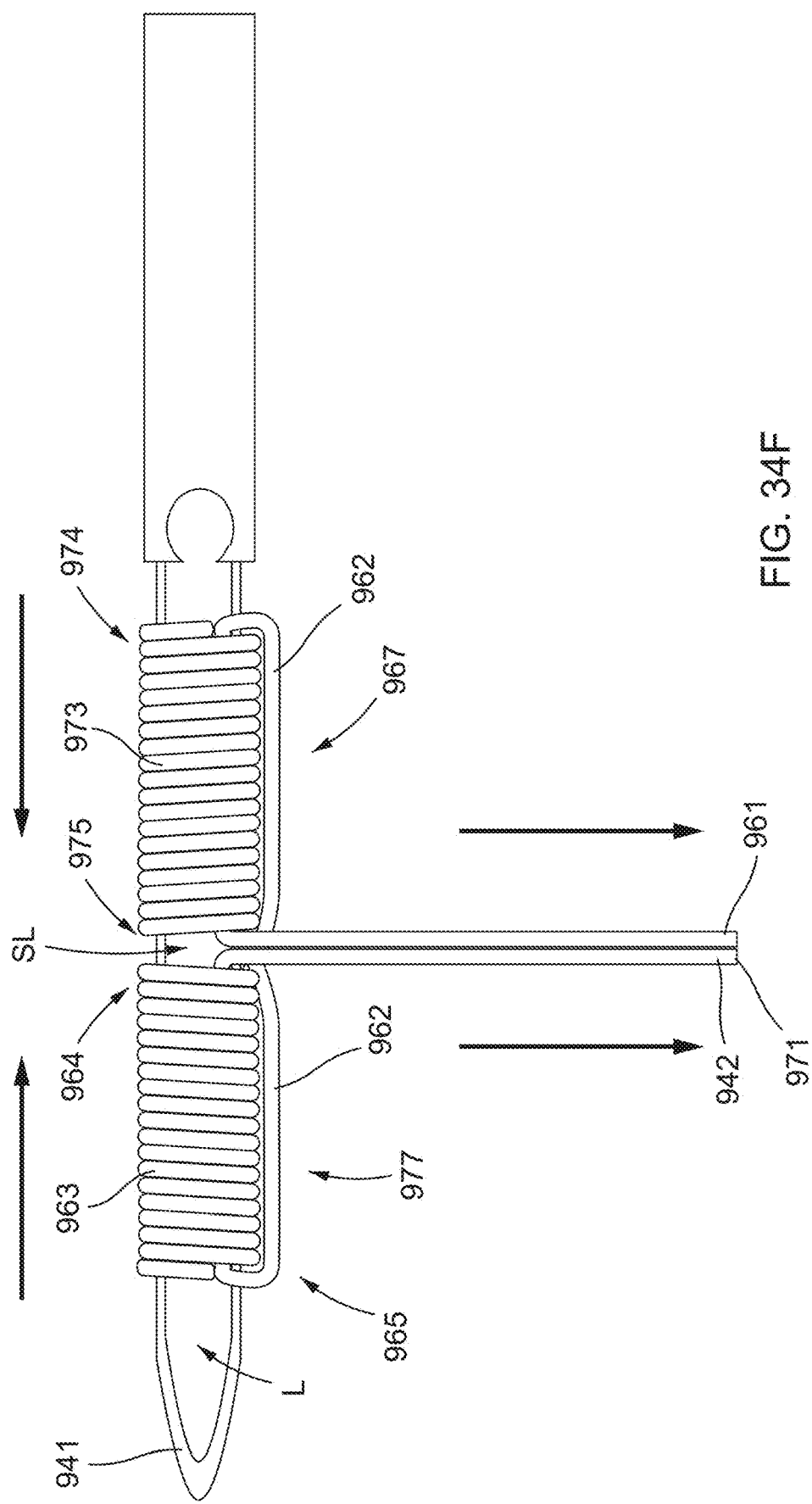
Figure 34G:
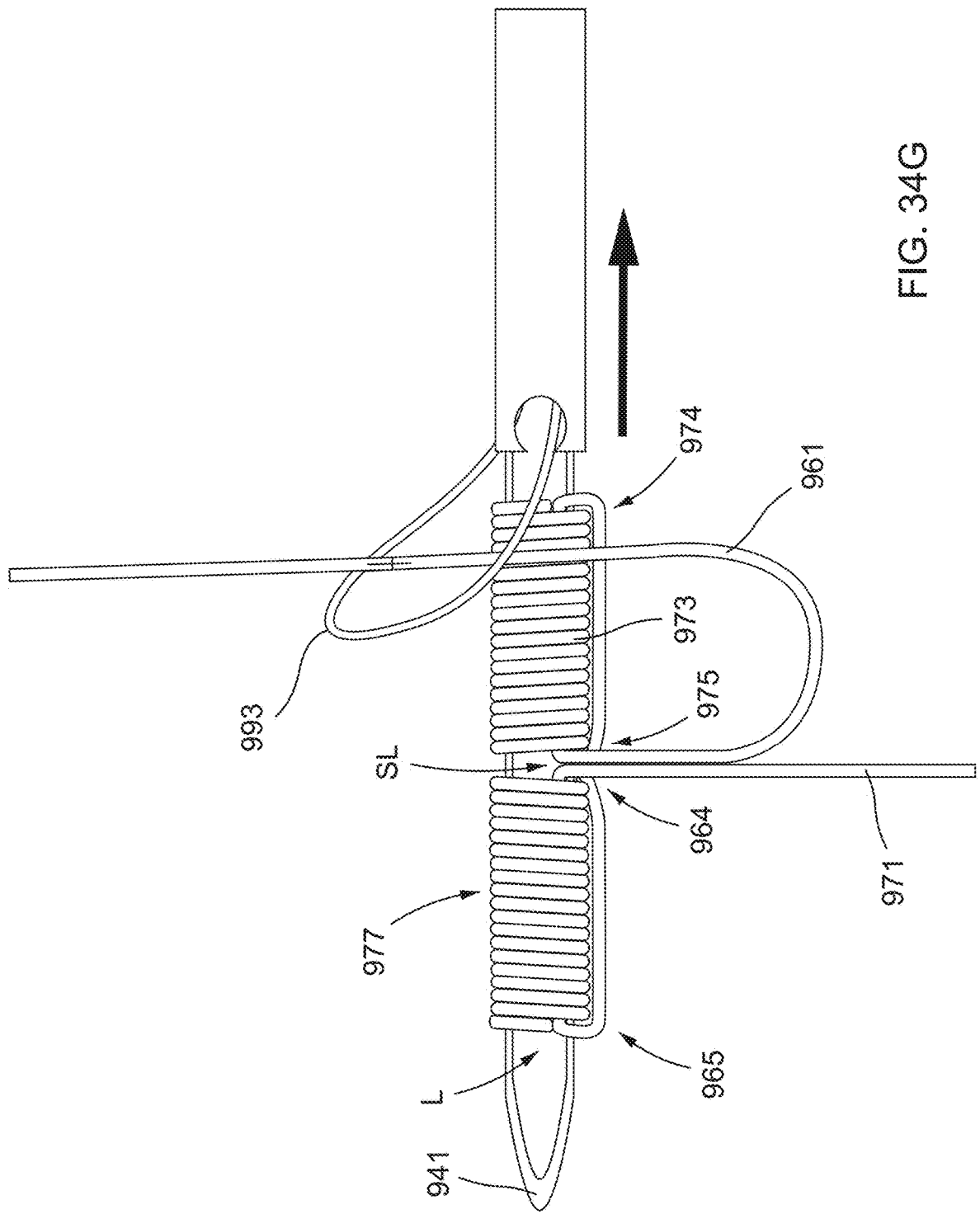
Figure 34H:
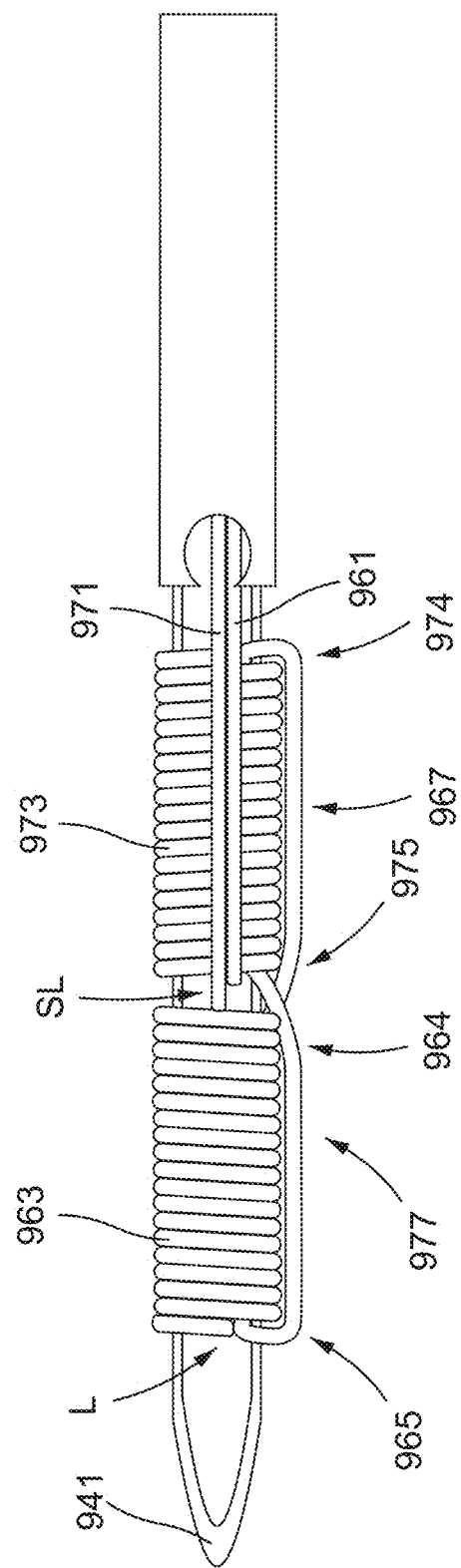

In some embodiments, a snare 993 can be used to facilitate routing of the suture 942 and forming of the distal anchor 942, as illustrated in FIGS. 34C, 34D, and 34 G. For example, the snare 993 can be used to route the first portion 961 of the first section 960 and the first portion 971 of the second section 970 into the interior lumen L of the needle and proximally through the interior lumen L.

Figure 35:
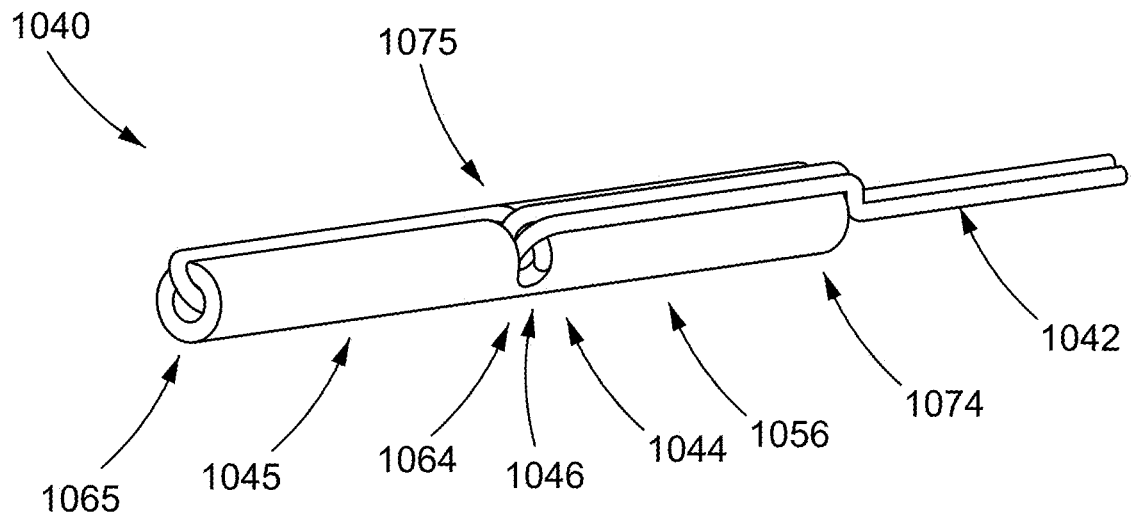
FIG. 35 is a side view of a distal anchor according to another embodiment, shown in a first delivery configuration.
Figure 36:
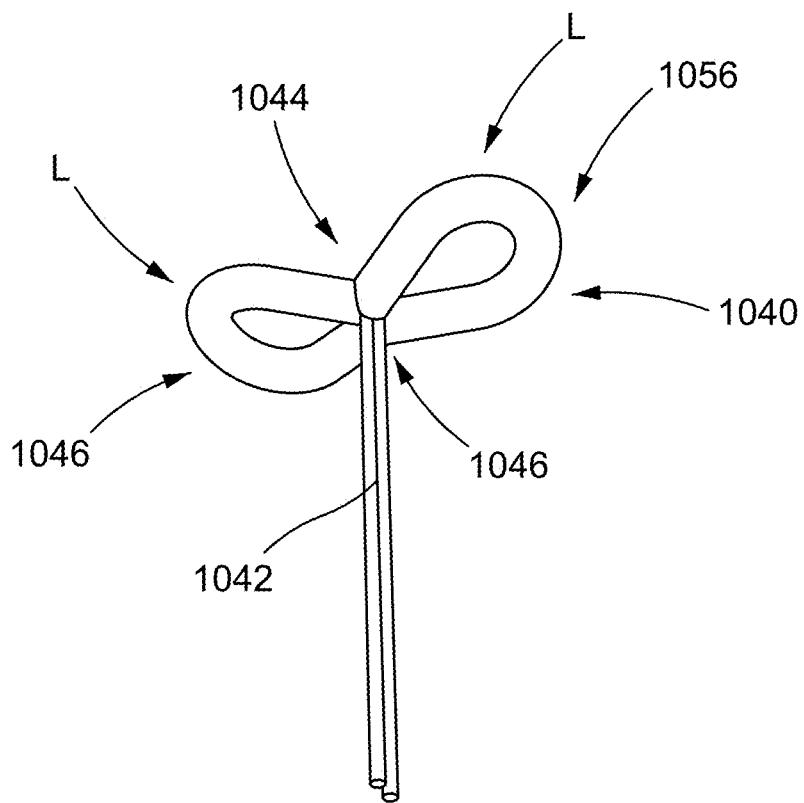
FIG. 36 is a side view of the distal anchor of FIG. 35 shown in a second deployed configuration.

In another embodiment of a distal anchor, the circumferential windings of the knot in the knot distal anchor 940 described above are replaced by a single flexible tube. Such an embodiment of a distal anchor is illustrated in FIGS. 35 and 36. FIG. 35 illustrates a distal anchor 1040 in an elongated delivery configuration, and FIG. 36 illustrates the distal anchor 1040 in a deployed configuration. In this embodiment, the flexible tube 1044 has a distal portion 1045, and a proximal portion 1056, and a slit 1046 separating the distal portion 1045 from the proximal portion 1056. In an alternative embodiment, instead of a single flexible tube 1044, the anchor 1040 can be formed with a separate distal tube and proximal tube (not shown), separated by a gap, rather than a partial circumference slit in a middle portion of a single flexible tube, as shown in FIG. 35. The suture 1043 is routed into and through the slit 1046, into a lumen of the flexible tube 1044, extending distally through the lumen from the slit 1045 towards and through a distal end 1065 of the distal portion 1045, then extending proximally along the exterior of the flexible tube 1044 towards and through a proximal end 1074 of the proximal portion 1056, then extending distally into and through the lumen of the flexible tube 1044 towards and through the distal end 1065 of the distal portion 1045, then extending proximally along the exterior of the flexible tube 1044 towards and through the proximal end 1074 of the proximal portion 1056, and then extending distally through the lumen of the flexible tube 1044 towards and through the slit 1045 and outside of the flexible tube 1044, as shown in FIG. 35.

Similar to the knot distal anchors described above with respect to previous embodiments, the distal anchor 1040 can be deployed in a similar manner using the delivery devices described above with respect to those embodiments. For example, the distal anchor 1040 can be delivered in the elongate configuration (FIG. 35) and moved to the deployed configuration (FIG. 36) by pulling the suture strands 1042 proximally to deflect the distal end 1065 of the distal portion 1045 of the flexible tube 1044 laterally with respect to a proximal end 1064 of the distal portion 1045 of the flexible tube 1044 to draw the proximal end 1064 and the distal end 1065 of the distal portion 1045 of the flexible tube 1044 towards each other to form a loop L as shown in FIG. 36. Similarly, the suture strands 1042 can be pulled proximally to deflect the distal end 1075 of the proximal portion 1056 of the flexible tube 1044 laterally with respect to a proximal end 1074 of the proximal portion 1056 of the flexible tube 1044 to draw the proximal end 1074 and the distal end 1075 of the proximal portion 1056 of the flexible tube 1044 towards each other to form a loop L as shown in FIG. 33.

Figure 37:
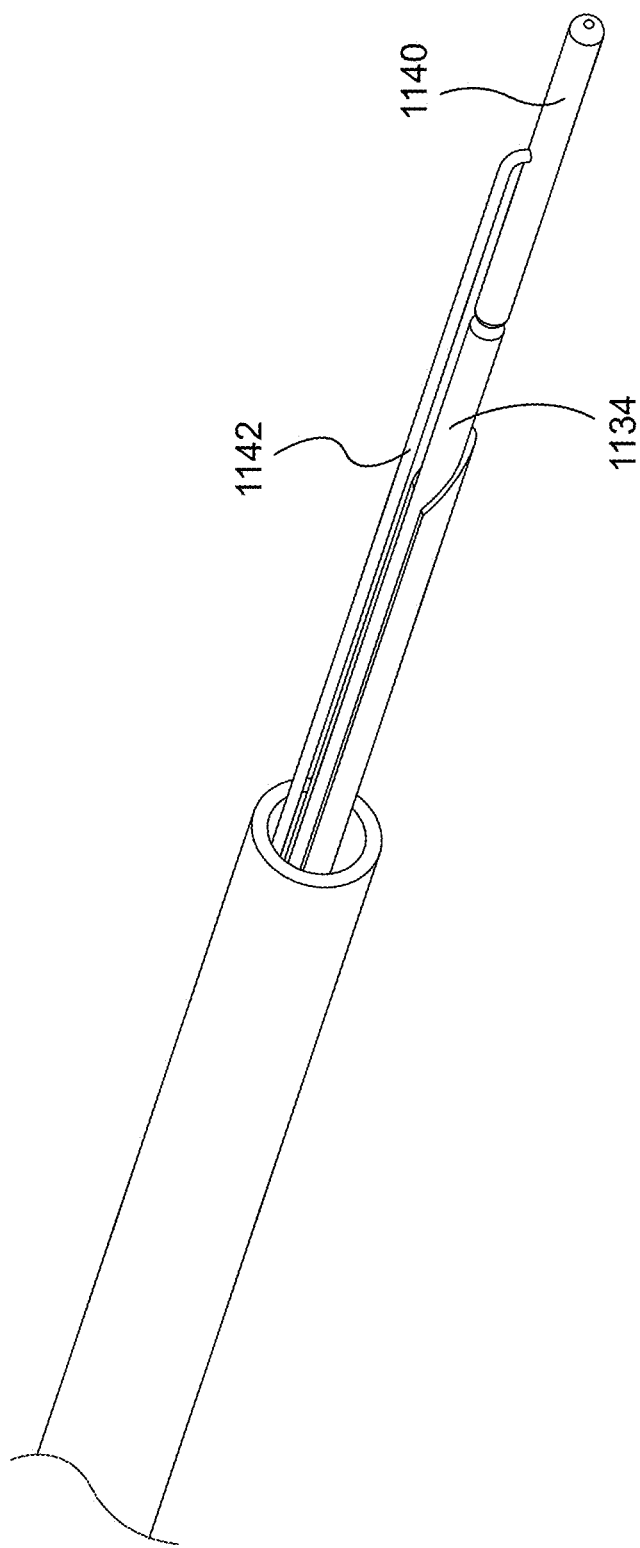
FIG. 37 is a perspective view of a distal anchor according to another embodiment, shown in a delivery configuration.

In another embodiment of a distal anchor, the circumferential windings of the knot in the knot distal anchor 240 described above are replaced by a T-fastener, as shown in an elongated delivery configuration in FIG. 37. Similar to the knot distal anchor 240 described above, the distal anchor (or T-fastener) 1140 can be deployed in a similar manner using any of the delivery devices described above with respect to previous embodiments. For example, the distal anchor 1140 can be coupled to a suture or sutures 1142 and removably coupled to or otherwise in operable contact with a pusher 1134. The distal anchor 1140 can be delivered in the elongate configuration and moved to the deployed configuration by pulling the suture 1142 proximally to rotate the distal anchor 1140 such that the distal anchor 1140 is non-parallel with respect to the pusher 1134, the distal end portion of the delivery device 1130, and/or the suture 1142. Simultaneously, the distal anchor 1140 can be decoupled or otherwise separated from (not shown) the pusher 1134 as the pusher 1134 is moved distally relative to a handle (not shown) of the delivery device and the suture 1142 is pulled proximally.

Figure 38A:
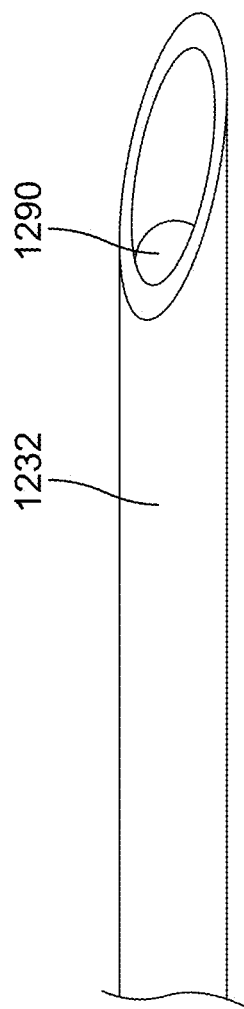
FIG. 38A is a side view of a distal anchor according to another embodiment shown in a first delivery configuration.
Figure 38B:
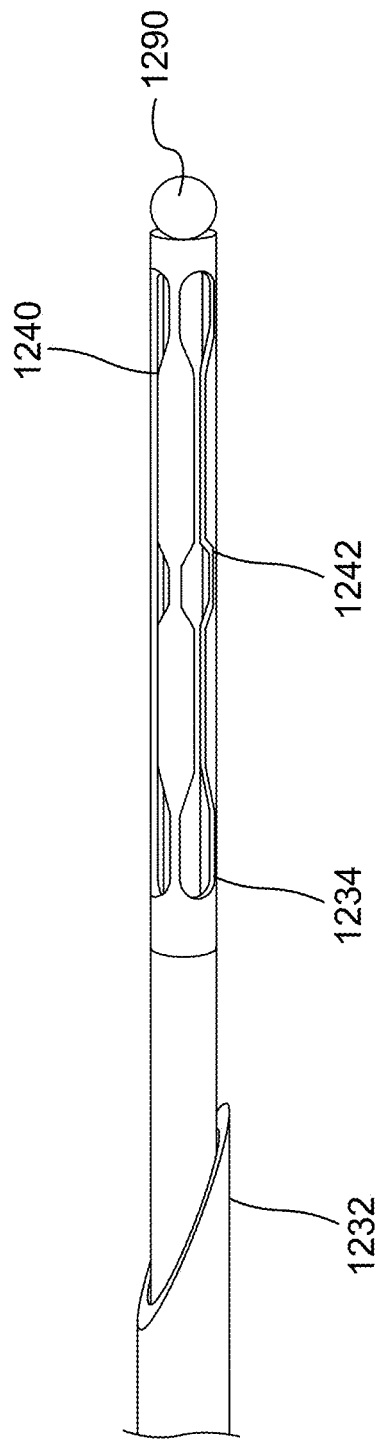
FIG. 38B is a side view of the distal anchor of FIG. 38A shown in a second delivery configuration.
Figure 38C:
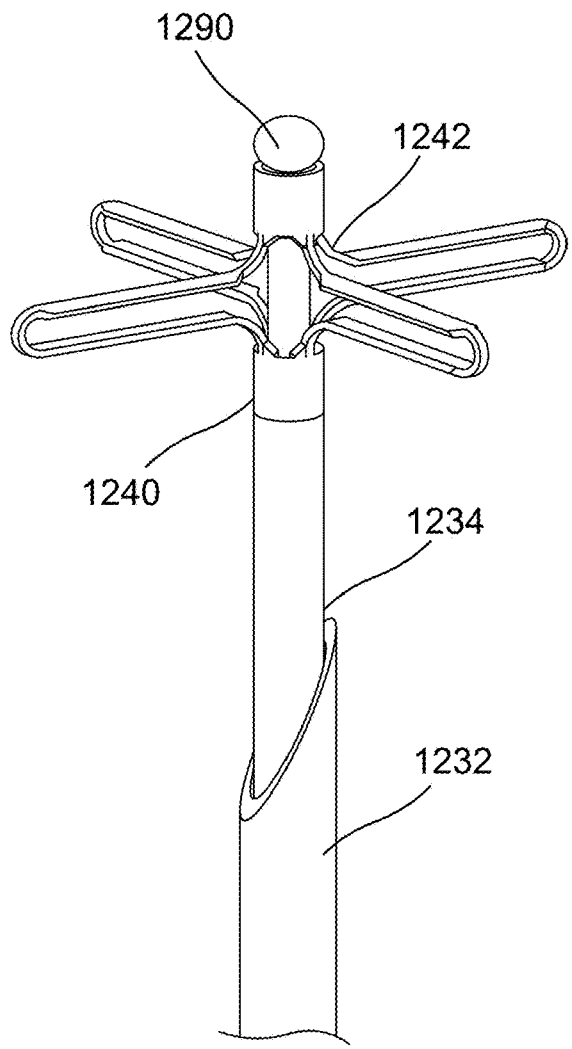
FIGS. 38C and 38D illustrate a side view and a perspective view, respectively, of the distal anchor of FIG. 38A shown in a deployed configuration.
Figure 38D:
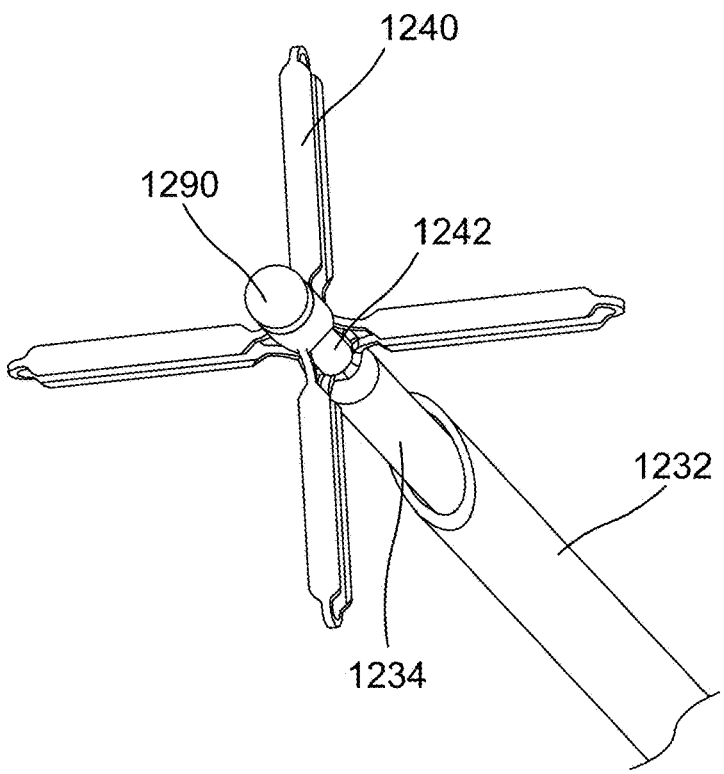

In another embodiment of a distal anchor, the circumferential windings of the knot in the knot distal anchor 240 described above are replaced by an expandable distal anchor, as shown in FIGS. 38A-38D. FIG. 38A illustrates the distal anchor 1240 in an elongated delivery configuration disposed within a lumen defined by and disposed through the distal end portion 1232 of the delivery device. FIG. 38B illustrates the distal anchor 1240 in the elongated deliver configuration and disposed outside of and distal to the distal end portion 1232 of the delivery device. FIGS. 38C and 38D illustrate the distal anchor 1240 in a deployed configuration in side and perspective view, respectively. Similar to the knot distal anchor 240 described above, the distal anchor 1240 can be deployed in a similar manner using any of the delivery devices described above with respect to previous embodiments. For example, the distal anchor 1240 can be coupled to a suture 1242 (or disposed about the suture 1242 such that the suture 1242 extends through a lumen defined by the distal anchor 1240) having a stopper 1290 disposed at a distal end of the suture 1242. The suture 1242 is removably coupled to or otherwise in operable contact with a pusher 1234. The distal anchor 1240 can be delivered in the elongate configuration (see e.g., FIGS. 38A and 38B) and moved to the deployed configuration by pulling the suture 1242 proximally and/or moving the pusher 1234 distally as shown in FIGS. 38C and 38D. In this manner, both the stopper 1290 and the pusher 1234 can collectively facilitate the transition of the distal anchor 1240 from the elongated delivery configuration to the radially expanded deployed configuration.

Figure 39A:
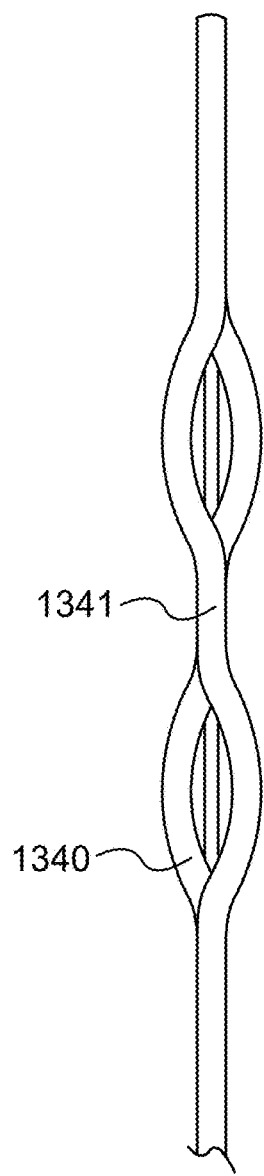
FIG. 39A is a side view of a distal anchor according to another embodiment shown in a delivery configuration.
Figure 39B:
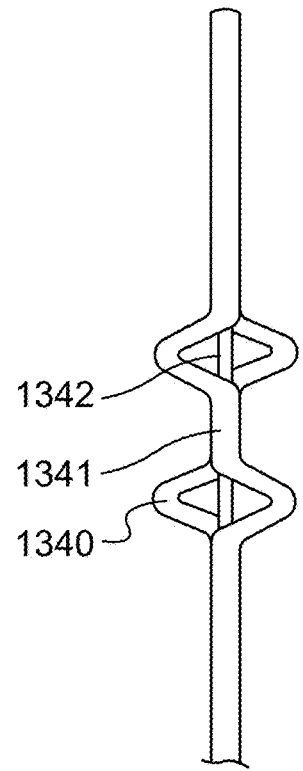
FIG. 39B is a side view of the distal anchor of FIG. 39A shown in a partially deployed configuration.
Figure 39C:
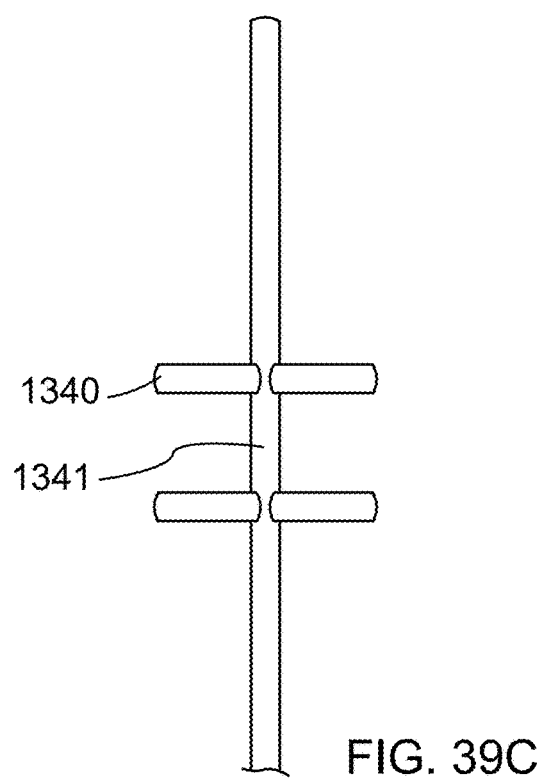
FIG. 39C is a side view of the distal anchor of FIG. 39A in a deployed configuration.

In another embodiment of a distal anchor, the expandable distal anchor 1240 described above is replaced by a double expandable distal anchor, as shown in FIGS. 39A-39C. FIG. 39A illustrates the distal anchor 1340 in an elongated delivery configuration. FIG. 39B illustrates the distal anchor 1340 in a partially deployed configuration. FIG. 39C illustrates the distal anchor 1340 in a deployed configuration. Similar to expandable distal anchor 1240 described above, the distal anchor 1340 can be deployed in a similar manner using, for example, any of the delivery devices described above with respect to previous embodiments. For example, the distal anchor 1340 can be disposed about a suture 1342 such that the suture 1342 extends through a lumen defined by the distal anchor 1340, and removably coupled to or otherwise in operable contact with a pusher (not shown). The distal anchor 1340 can be delivered in the elongate configuration (see e.g., FIG. 39A) and moved to the deployed configuration (see e.g., FIGS. 39B and 39C) by pulling the suture 1342 proximally and/or moving the pusher (not shown) distally. In this embodiment, the distal anchor 1340 includes two slits. As the suture 1342 is pulled proximally and/or the pusher (not shown) is moved distally, the slits facilitate expansion of two portions of the distal anchor 1340, as shown in FIG. 39B. In its deployed configuration, the ends of the first slit and the ends of the second slit are brought into or nearly into contact with one another, as shown in FIG. 39C to maximize the expansion of the two portions of the distal anchor 1340.

In use, in some embodiments, the distal anchor 1340 is delivered in the elongate configuration (see e.g., FIG. 39A) through an opening in a leaflet (e.g., a prolapsed segment of a native mitral valve leaflet) until a medial portion 1341 of the distal anchor 1340 is disposed in the opening of the leaflet and a first slit is disposed in the left atrium of the heart and the second slit is disposed in the left ventricle of the heart. The distal anchor 640 is then moved into its deployed configuration (see e.g., FIGS. 39B and 39C) such that the two portions (defined in part by the slits) expand radially and/or laterally. In this manner, the two portions of the distal anchor 1340 can collectively grab, grasp, sandwich, or otherwise maintain a portion of the native valve leaflet therebetween. In addition to operably coupling the distal anchor 1340 to the native valve leaflet, the distal anchor 1340 when deployed provides a seal across the opening of the leaflet to prevent or otherwise limit any fluid flow through the opening. In some embodiments, the portions of the distal anchor 1340 can be deployed (e.g., expanded) simultaneously, while in other embodiments the portions of the distal anchor 1340 can be deployed sequentially, e.g., the distal portion can be deployed at a first time and the proximal portion can be deployed at a second time after the first time, or vice versa.

In another embodiment of a distal anchor, the circumferential windings of the knot in the knot distal anchor 240 described above are replaced by an expandable distal anchor (or umbrella anchor), as shown in FIGS. 40A-37C. FIG. 40A illustrates the distal anchor 1440 in an elongated collapsed delivery configuration and proximate to a distal end portion 1432 of a delivery device. FIG. 40B illustrates the distal anchor 1440 in a partially deployed configuration. FIG. 40C illustrates the distal anchor 1440 in a deployed or expanded configuration and disposed distal to a valve leaflet VL. In this embodiment, during delivery of the distal anchor 1440, the interior walls of the distal end portion 1432 can retain the distal anchor 1440 in its elongated delivery configuration when the distal anchor 1440 is disposed within a lumen defined by the distal end portion 1432. When in the elongated delivery configuration, an open end portion 1440a of the distal anchor 1440 is disposed proximal to a rounded distal end 1440b of the distal anchor as shown in FIG. 40A. Similar to distal anchor 240 described above, the distal anchor 1440 can be deployed in a similar manner using any of the delivery devices described above with respect to previous embodiments. For example, the distal anchor 1440 can be coupled to a suture 1442 and removably coupled to or otherwise in operable contact with a pusher 1434. The distal anchor 1440 can be delivered in the elongate configuration (see e.g., FIG. 40A), and moved to the deployed configuration (see e.g., FIGS. 40B and 40C) by pulling the suture 1442 proximally and/or moving the pusher 1434 distally. As the distal anchor 1440 is moved distally and the open end portion 1440a exits the distal end portion 1432 of the delivery device, the distal anchor 1440 is allowed to expand (i.e., the open end 1440a opens) towards its deployed or expanded configuration, as shown in FIG. 40B.

In an alternative embodiment, a distal anchor can be configured similar to the distal anchor 1440 except that the distal anchor can be disposed on the suture 1442 such that the open end of the umbrella shaped portion is distal to the rounded distal end of the distal anchor. In such an embodiment, the rounded distal end can define a hole through which the suture can be extended and secured. The distal anchor can be formed with for example a shape-memory material such that the distal anchor has a biased expanded or deployed configuration and an elongated collapsed configuration when constrained within a delivery device. The distal anchor can be pushed or moved out of a delivery device with, for example, a pusher device. As the distal anchor exits a distal end of the delivery device, the distal anchor can transition from its elongated collapsed configuration to its expanded, deployed or biased configuration. Said another way, as the distal anchor exits the distal end of the delivery device, the open end of the distal anchor opens to its expanded or biased configuration. In this manner, the distal anchor can transition from its delivery configuration to its deployed configuration as it exits the delivery device.

Figure 41C:
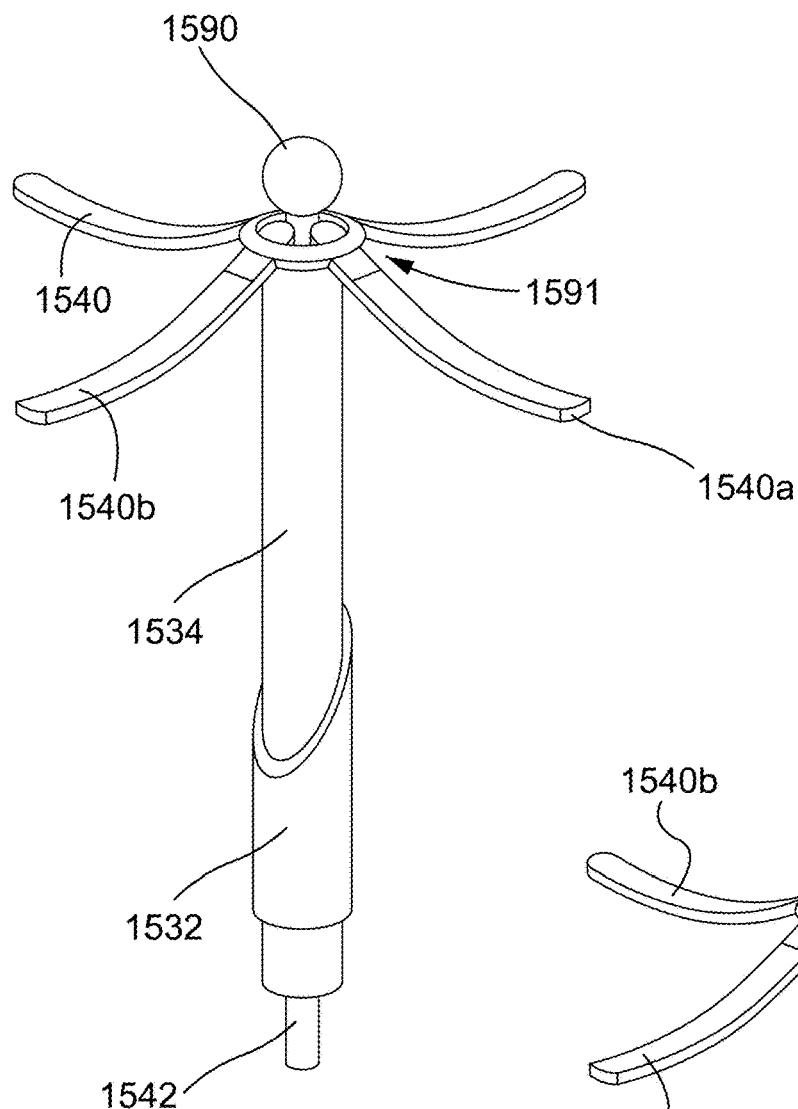
FIG. 41C illustrates the distal anchor of FIG. 41A in a partially deployed configuration.
Figure 41D:
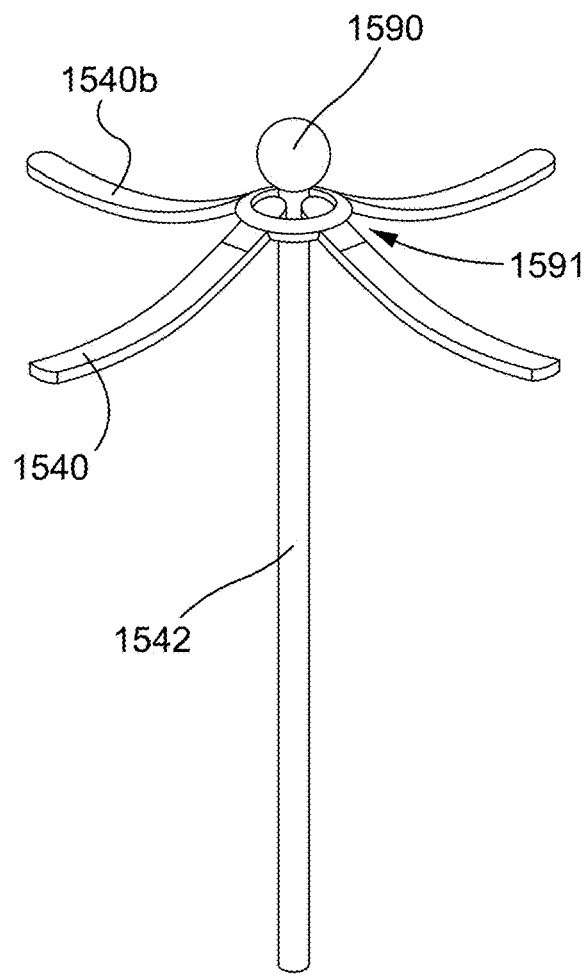
FIG. 41D illustrates the distal anchor of FIG. 41A in a deployed configuration.

In another embodiment of a distal anchor, the circumferential windings of the knot in the knot distal anchor 240 described above are replaced by an expandable distal anchor, as shown in FIGS. 41A-41D. In this embodiment, the distal anchor 1540 includes elongate members 1540b with free ends 1540a and a stopper receiving section 1591. FIG. 41A illustrates the distal anchor 1540 in an elongated delivery configuration and disposed within a lumen defined by a distal end portion 1532 of a delivery device such that the free ends 1540a of elongate members 1540b are disposed proximal to the stopper receiving section 1591 of the distal anchor 1540. FIG. 41B illustrates the distal anchor 1540 in the elongated delivery configuration. FIGS. 41C and 41D illustrate the distal anchor 1540 in a deployed configuration. In this embodiment, a distal end portion of the suture 1542 includes a stopper 1590 and the stopper receiving section 1591 of the distal anchor 1540 is configured to cooperatively mate with the stopper 1590. During delivery of the distal anchor 1540, the interior walls of the distal end portion 1532 can retain the distal anchor 1540 in its elongated delivery configuration when the distal anchor 1540 is disposed within a lumen defined by the distal end portion 1532, as shown in FIG. 38A. Similar to distal anchor 240 described above, the distal anchor 1540 can be deployed in a similar manner using any of the delivery devices described above with respect to previous embodiments. For example, the distal anchor 1540 can be coupled to a suture 1542 and removably coupled to or otherwise in operable contact with a pusher 1534. The distal anchor 1540 can be delivered in the elongated configuration (see e.g., FIG. 41A) and moved to the deployed configuration (see e.g., FIGS. 41B and 41C) by pulling the suture 1542 proximally and/or moving the pusher 1534 distally (see e.g., FIG. 41C). In this manner, the stopper 1590 of the suture 1542 can be moved into contact with the stopper receiving section 1591, and the stopper 1590 and the stopper receiving section 1591 can collectively facilitate the transition of the distal anchor 1540 from the elongated delivery configuration to the expanded deployed configuration.

In an alternative embodiment, a distal anchor can be configured similar to the distal anchor 1540 except that the distal anchor can be disposed on the suture 1542 such that the free ends of the elongate members are distal to the stopper receiving section. In such an embodiment, the distal anchor can be formed with for example a shape-memory material such that the distal anchor has a biased expanded or deployed configuration and an elongated collapsed configuration when constrained within a delivery device. The distal anchor can be pushed or moved out of a delivery device with, for example, a pusher device. As the distal anchor exits the delivery device, a distal end of the distal anchor can transition from its elongated collapsed configuration to its expanded, deployed or biased configuration. Said another way, as the distal anchor exits the distal end of the delivery device, the free ends of the elongate members can extend radially towards the deployed or biased configuration of the distal anchor. In this manner, the distal anchor can transition from its delivery configuration to its deployed configuration as it exits the delivery device.

Figure 42A:
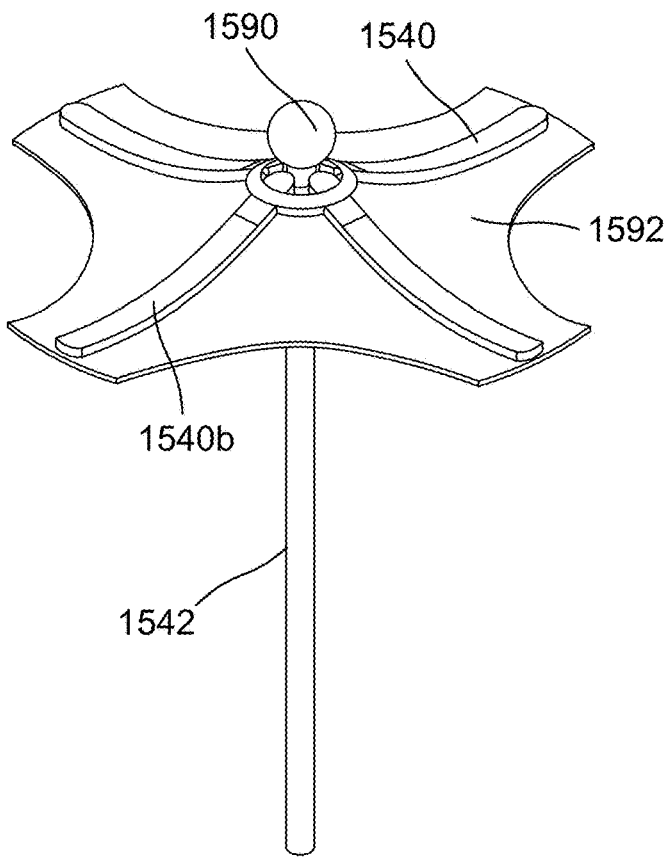
FIGS. 42A and 42B illustrate the distal anchor of FIG. 41A, shown in the deployed configuration.
Figure 42B:
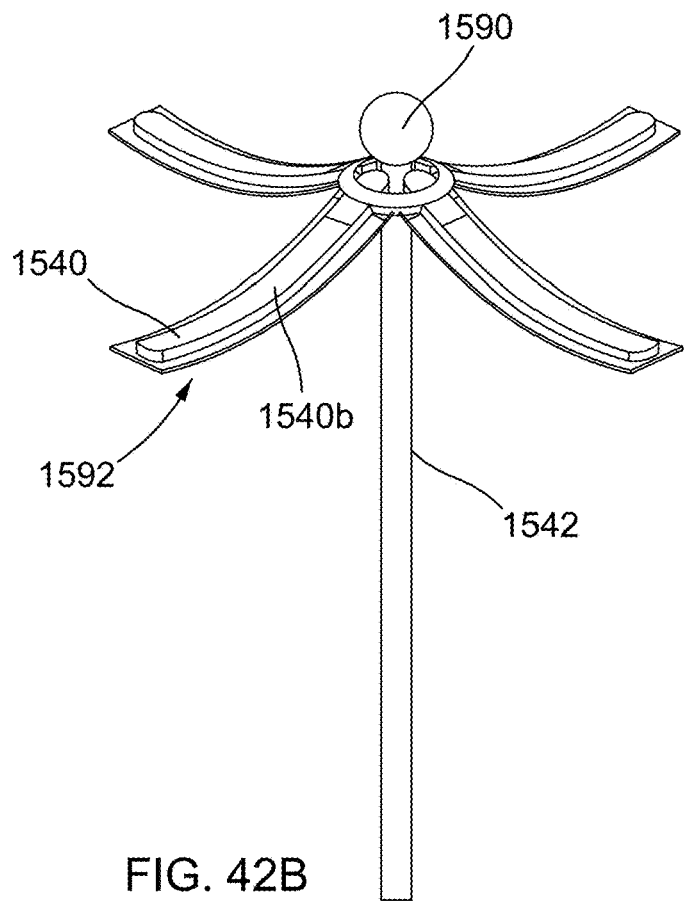

The distal anchor 1540 can be formed of any suitable material, such as, for example a malleable stainless steel, a shape memory or superelastic alloy, or a polymer. One such polymer, for example, can include polyaryletherketones (PAEKs) such as polyetheretherketone (PEEK). Optionally, in some embodiments, a distal anchor can include or be coupled to a material (e.g., a fabric and/or polymer) that is configured to distribute an anchor load, cover and/or seal the hole made in the leaflet, and/or promote ingrowth or an otherwise desirable biological response when the distal anchor is disposed within a heart. For example, as illustrated in FIGS. 42A and 42B, the distal anchor 1540 of FIGS. 41A-41D can have such a material 1592 coupled thereto. For example, in some embodiments, the material 1592 can extend between the elongate members 1540*b* and beyond the free ends 1540*a* of the distal anchor 1540, as shown in FIG. 42A. In some embodiments, the material 1592 can be sized and shaped to replicate or nearly replicate the size and shape of the elongate members 1540*b* of the distal anchor 1540, as shown in FIG. 42B.

Figure 43B:
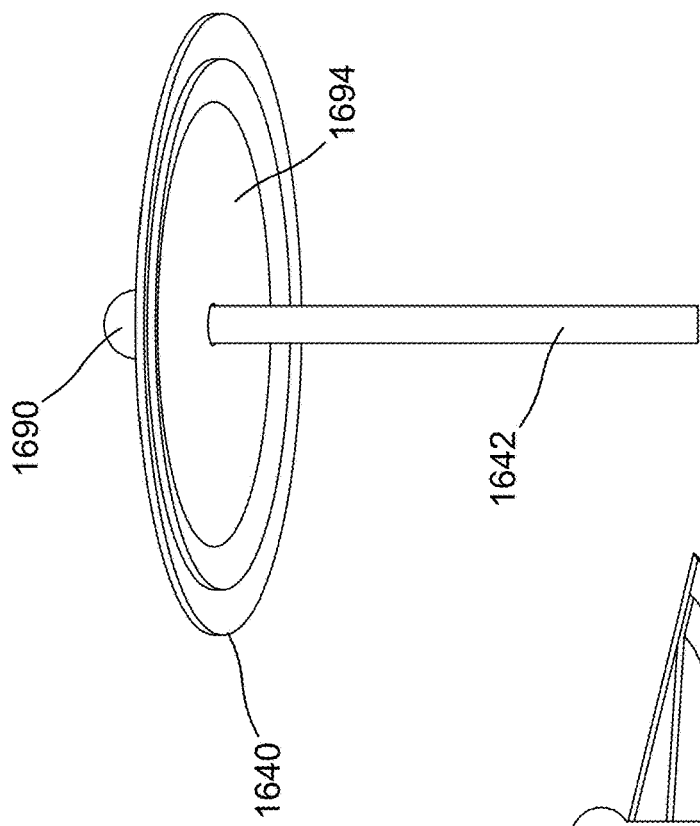
FIGS. 43A-43C illustrate a distal anchor according to another embodiment, shown in a deployed configuration.
Figure 43C:
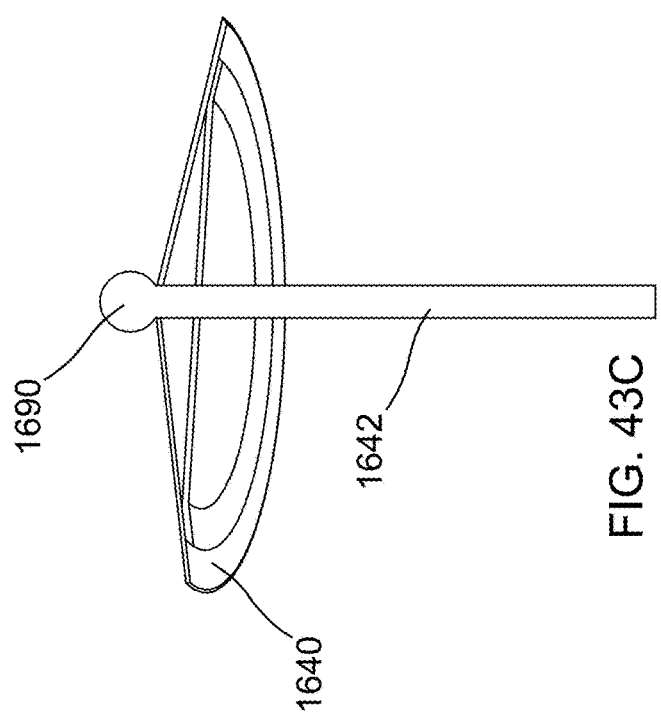
Figure 43A:
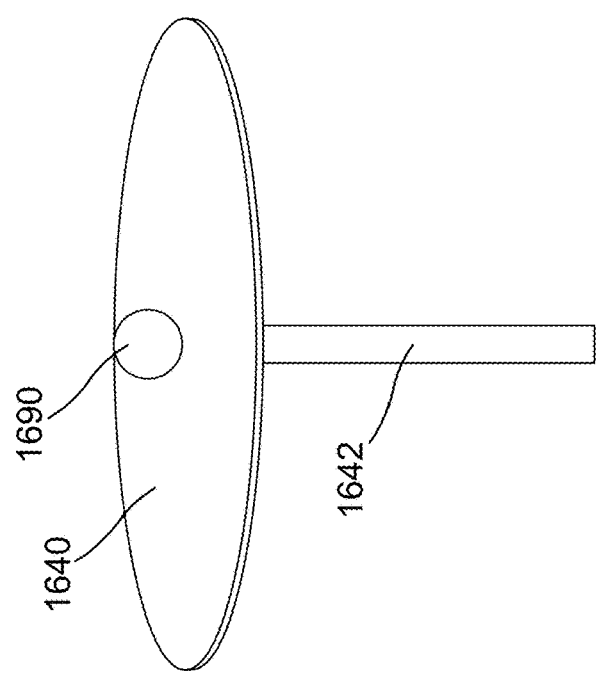

In another embodiment of a distal anchor, the circumferential windings of the knot in the knot distal anchor 240 described above are replaced by an expandable distal anchor, as shown in FIGS. 43A-43C. FIG. 43A illustrates a distal end portion of the distal anchor 1640 in a deployed configuration. FIG. 43B illustrates a proximal end portion of the distal anchor 1640 in the deployed configuration. FIG. 43C illustrates in partial cross-section the distal anchor 1640 in the deployed configuration. In this embodiment, a distal end portion of the suture 1642 includes a stopper 1690. A radial support member 1694 is coupled and disposed proximal to the proximal end portion of the distal anchor 1640. The radial support member 1694 can prevent or otherwise limit the distal anchor 1640 from undesirably flipping or deflecting (1) beyond a plane defined by the stopper 1690, and/or (2) distal to the stopper 1690. The radial support member 1694 can be made of any suitable material sufficient to provide radial support, such as, for example, a non-elastic material. In addition, as shown best in FIG. 43C, the distal anchor 1640 is pre-configured to have a slight angle.

Similar to distal anchor 240 described above, the distal anchor 1640 can be deployed in a similar manner using any of the delivery devices described above with respect to previous embodiments. For example, the distal anchor 1640 can be coupled to the suture 1642 and removably coupled to or otherwise in operable contact with a pusher (not shown). The distal anchor 1640 can be delivered in the elongated configuration (not shown) and moved to the deployed configuration by pulling the suture 1642 proximally and/or moving the pusher (not shown) distally, as shown in FIGS. 43A-43C. In this manner, the stopper 1690 of the suture 1642 can be moved into contact with the distal end portion of the distal anchor 940, and as a result, can collectively facilitate the transition of the distal anchor 1640 from the elongated delivery configuration (not shown) to the expanded deployed configuration. Although not shown, in some embodiments, the distal anchor 1640 can include radial stiffening members in addition to or instead being coupled to the radial support member 1694.

Figure 44C:
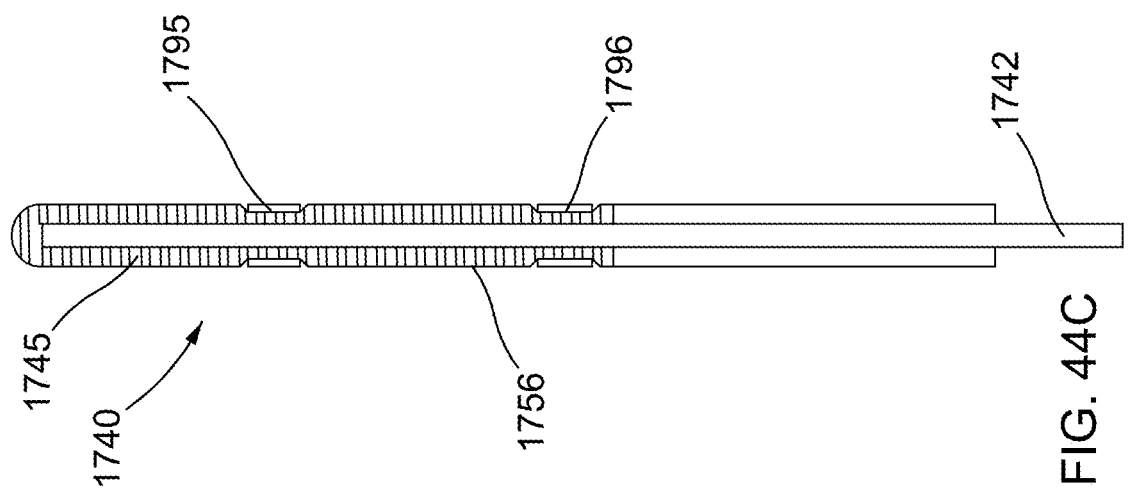
FIG. 44C illustrates in cross-section the distal anchor of FIG. 44A, shown in the delivery configuration.
Figure 44B:
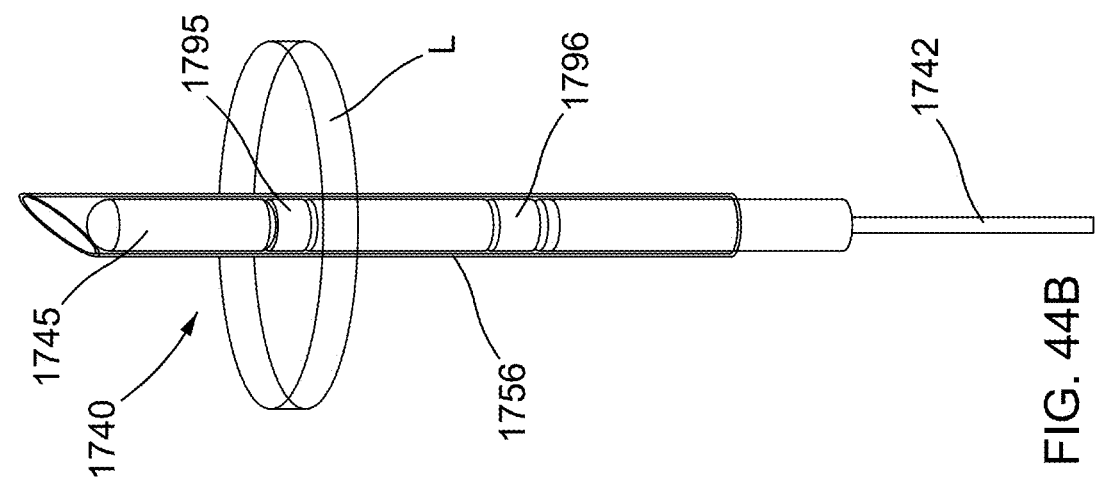
FIG. 44B illustrates the distal anchor of FIG. 44A, shown with reference to a valve leaflet and in the delivery configuration.
Figure 44A:
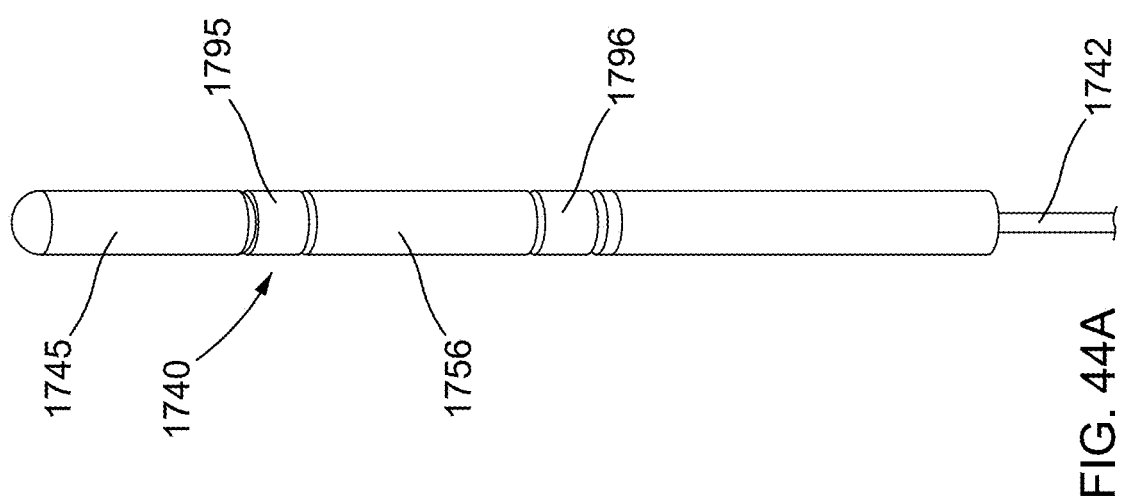
FIG. 44A illustrates a distal anchor according to another embodiment, shown in a delivery configuration.
Figure 44E:
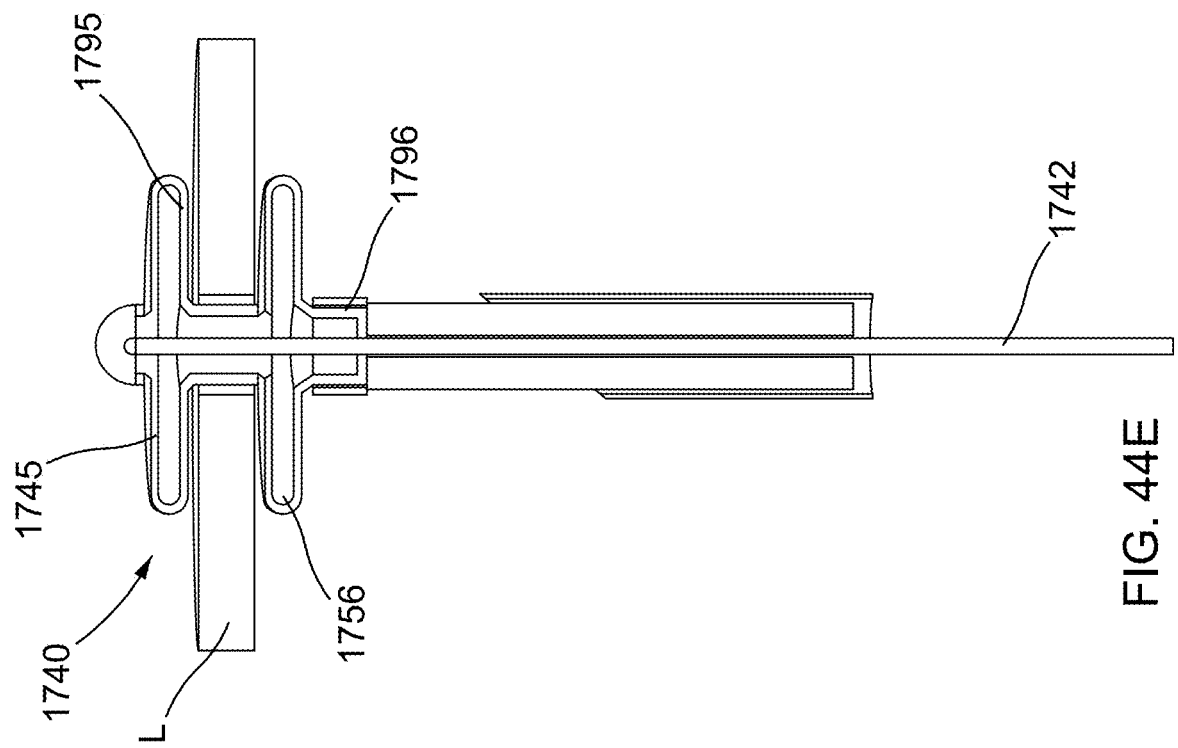
FIG. 44E illustrates in cross-section the distal anchor of FIG. 44A, shown with reference to the valve leaflet and in the deployed configuration.
Figure 44D:
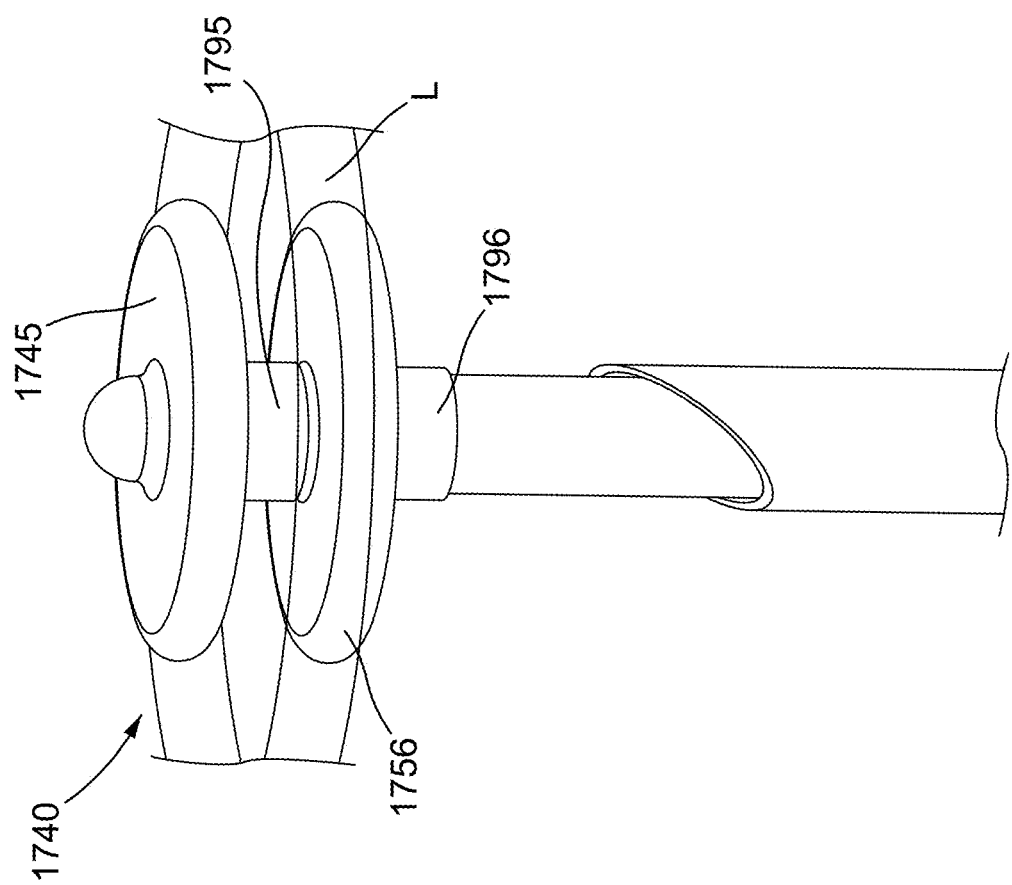
FIG. 44D illustrates the distal anchor of FIG. 44A, shown with reference to the valve leaflet and in a deployed configuration.

In another embodiment of a distal anchor, the circumferential windings of the knot in the knot distal anchor 240 described above are replaced by an expandable braid, as shown in FIGS. 44A-44E. FIG. 44A illustrates the expandable braid distal anchor 1740 in an elongated delivery configuration, FIG. 44B illustrates the distal anchor 1740 in the elongated delivery configuration with reference to a valve leaflet L, and FIG. 44C illustrates the distal anchor 1740 in cross-section in the elongated delivery configuration. FIG. 44D illustrates the distal anchor 1740 in an expanded or deployed configuration with reference to a valve leaflet L, and FIG. 44E illustrates in cross-section the distal anchor 1740 in the deployed configuration. In this embodiment, the expandable braid distal anchor 1740 has a distal portion 1745, a proximal portion 1756, and a distal collar 1795 disposed therebetween. The distal anchor 1740 also includes a proximal collar 1796 disposed proximal to the proximal portion 1756 of the distal anchor 1740. Similar to the knot distal anchor 240 described above, the distal anchor 1740 can be deployed in a similar manner using any of the delivery devices described above with respect to previous embodiments. For example, the distal anchor 1740 can be coupled to a suture 1742. The distal anchor 1740 can be delivered in the elongate configuration and moved to the deployed configuration by pulling the suture strands 1742 proximally to cause the braided distal portion 1745 and the braided proximal portion 1756 to expand radially, as shown in FIGS. 44D and 44E.

Prior to deployment of the expandable braid distal anchor 1740, the distal collar 1795 can be aligned with and disposed at least partially within the hole formed in the leaflet L, as shown in FIG. 44B. In this manner, when deployed (radially expanded), the distal portion 1745 of the distal anchor 1740 will be disposed on the distal side of the leaflet L (e.g., within the atrium of the heart), and the proximal portion 1746 of the distal anchor 1740 will be disposed on the proximal side of the leaflet L (e.g., within the ventricle of the heart), as shown in FIG. 44D. Deployment of the distal portion 1745 and the proximal portion 1746 can be initiated in stages. For example, deployment of the distal portion 1745 can be initiated while the proximal portion 1746 is in the elongated delivery configuration, and deployment of the proximal portion 1746 can be initiated after the distal portion 1745 has transitioned into the deployed configuration.

Further to this example, in use, the distal anchor 1740 can be inserted into the atrium of the heart and the distal portion 1745 can be deployed within the atrium. Next, the suture 1742 can be pulled proximally such that a proximal side surface of the distal portion 1745 of the distal anchor 1740 is brought into contact with an atrial side of the heart valve leaflet L. In this manner, the distal portion 1745 can be manipulated into a desirable position before the proximal portion 1746 of the distal anchor 1740 is deployed. Once the distal portion 1745 is suitable positioned against the valve leaflet L, the proximal portion 1746 of the distal anchor 1740 can be deployed such that a distal side surface of the proximal portion 1746 is brought into contact with a ventricle side of the valve leaflet L, thereby securing the leaflet L between the distal portion 1745 and the proximal portion 1746.

Although not shown, in some embodiments, the distal anchor 1740 can include a locking mechanism configured to lock, bias, or otherwise maintain the distal anchor 1740 in its expanded deployed configuration. Further, in some embodiments, the distal portion 1745 and the proximal portion 1746 can be formed of shape memory or superelastic material such that its expanded deployed configuration is its unbiased configuration.

In another embodiment of a distal anchor, the circumferential windings of the knot in the knot distal anchor 240 described above are replaced by a single flexible tube, as shown in FIGS. 45A-45C. FIG. 45A illustrates the distal anchor 1840 in an elongated delivery configuration, and FIGS. 45B and 45C illustrate the distal anchor 1840 in a deployed configuration, in side view and perspective view, respectively. In this embodiment, the flexible tube 1840 has a distal portion 1845, and a proximal portion 1856, and a medial portion 1846 disposed therebetween. Each portion is separated by a hinge section, i.e., a first hinge section 1897 is disposed between the distal portion 1845 and the medial portion 1846, and a second hinge section 1898 is disposed between the medial portion 1846 and the proximal portion 1856. The suture 1842 includes a stopper 1890 at its distal end, and extends therefrom through a first aperture AP1, a second aperture AP2 and a third aperture AP3, each of which is defined by the flexible tube 1840, as shown in FIGS. 45A-45C.

Similar to the knot distal anchor 240 described above, the distal anchor 1840 can be deployed in a similar manner using any of the delivery devices described above with respect to previous embodiments. The distal anchor 1840 can be delivered in the elongate configuration and moved to the deployed configuration by pulling the suture strand 1842 proximally to deflect the portions 1845, 1846, 1156 about their respective hinge sections 1897, 1898, as shown in FIGS. 45B and 45C. In this manner, the portions 1845, 1846, 1856 are drawn towards each other (or folded onto one another) to form the expanded deployed configuration.

The distal anchor 1840 can be formed of any suitable material, e.g., ePFTE or a similar biocompatible polymer. In an alternative embodiment, instead of a single flexible tube 1844, the anchor 1840 can be formed of separate portions and then coupled together. Further, in an alternative embodiment, instead of three portions (i.e., distal, proximal, medial), the anchor 1840 can include any suitable number of portions (e.g., a single portion or four or more portions).

Figure 46A:
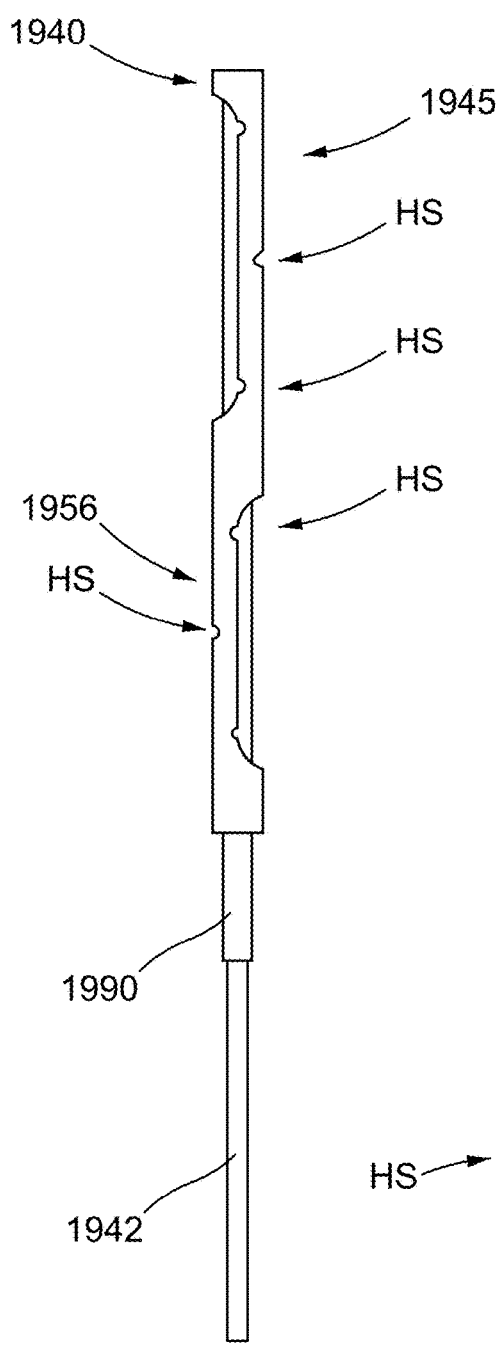
FIG. 46A illustrates a distal anchor according to another embodiment, shown in a in a delivery configuration.
Figure 46B:
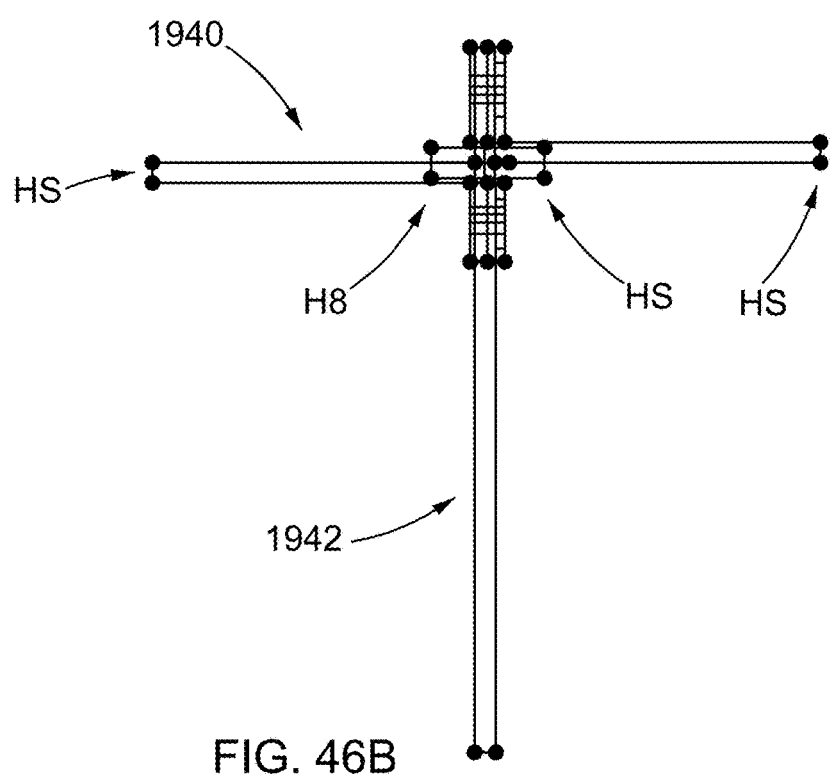
FIG. 46B is a schematic of the distal anchor of FIG. 46A, shown in a deployed configuration.

In another embodiment of a distal anchor, the circumferential windings of the knot in the knot distal anchor 240 described above are replaced by a hinged tube, as shown in FIGS. 46A and 43B. FIG. 46A illustrates the distal anchor 1940 in an elongated delivery configuration, and FIG. 46B illustrates schematically the distal anchor 1940 in a deployed configuration. In this embodiment, the hinged tube 1940 has a distal portion 1945, and a proximal portion 1956, and hinge sections HS to facilitate deployment, deflection or bending of the distal portion 1945 and the proximal portion 1956 at desirable sections of the distal anchor 1940. A distal end portion of an elongated tube 1999 is fixedly coupled to a distal end of the distal portion 1945 of the distal anchor 1940, and extends through a lumen defined by the distal anchor 1940, out a proximal end of the proximal portion 1945 of the distal anchor 1940, and then coupled to a suture 1942, as shown in FIG. 46A. Similar to the knot distal anchor 240 described above, the distal anchor 1940 can be deployed in a similar manner using any of the delivery devices described above with respect to previous embodiments. For example, the distal anchor 1940 can be delivered in the elongate configuration and moved to the deployed configuration by pulling the suture strand 1942 proximally, and thereby similarly moving the elongated tube 1999 proximally with the suture strand 1942, to deflect the hinged tube 1940 laterally with respect to the hinge sections HS to form the deployed or expanded configuration, as shown in FIG. 46B.

While some of the distal anchors described above as being delivered to a left ventricle of a heart, piercing a native mitral valve leaflet from the ventricular side to the atrial side, deploying the distal anchor on the atrial side of the leaflet, and anchoring the distal anchor to an apex region of the heart, in other instances, the distal anchors described above can be delivered and deployed via other suitable methods, e.g., transfemorally, transatrially and/or via an inferior vena cava (IVC). For example, in some embodiments, one or more native valve leaflets can be pierced from the atrial side to the ventricular side, and the distal anchor can be delivered from the atrial side to the ventricular side and deployed in the ventricle. In such embodiments, in some instances, the distal anchor can be attached or otherwise coupled to (e.g., via a suture) a second distal anchor (e.g., deployed at a second leaflet). In some instances, the distal anchor can be anchored to the apical region of the heart by routing a suture attached to the anchor through the area or void between the leaflets from the atrial side to the ventricular side.

It should be understood that the distal anchors described herein can be delivered and deployed using any of the delivery devices described herein or any other suitable delivery device. While some embodiments described herein have included delivery devices configured to deploy a bulky knot distal anchor, in other embodiments, those delivery devices can be configured to deliver and deploy any suitable distal anchor, such as, for example, any of the distal anchors illustrated in FIGS. 35-46B.

It should be understood that although in various embodiments described herein the puncture member was shown and described as defining an internal lumen through which an artificial chorda can extend, in other embodiments, any of the delivery devices described herein can include a puncture member having a solid shaft along which an artificial chorda can extend. In such embodiments, for example, a proximal end portion of the artificial chorda can be coupled to an actuator of the delivery device.

Although in various embodiments described herein, such as, for example, the embodiments described with reference to full forward deployment sequences, a portion of the suture is illustrated and described as being coupled to the actuator and/or a suture catch, in alternative embodiments, a portion (e.g., a proximal end portion) of the suture can be coupled (e.g., fixedly coupled) to any suitable portion of the delivery device. For example, in some embodiments, a proximal end portion of the suture can be fixedly coupled to the handle of the delivery device.

In various embodiments described herein, to allow the distal anchor to slide relative to the actuator, when the suture is loaded within the delivery device, there is slack in the suture between the distal anchor and the suture lock within the suture catch (or other location at which the proximal end portion of the suture is fixedly coupled). In alternative embodiments, in addition to or instead of the slack, any suitable mechanism can be used. For example, in some embodiments, a spring or the like can be coupled to the suture and a portion of the handle of the delivery device such that the distal anchor can slide as discussed in further detail herein.

It should be understood that although in various embodiments described herein the delivery device includes an outer tube and an end effector, in other embodiments, a delivery device can be constructed similar to and can function similar to any of the delivery devices described herein, except the delivery device does not include an outer tube and an end effector. In such embodiments, for example, in some instances, the delivery device can deliver and deploy a distal anchor in cooperation with a separate device or devices configured to function similar to or the same as the outer tube and/or end effectors described herein. For example, in some instances, an introducer valve, sheath, catheter or the like can be used. In such instances, the puncture member and/or pusher device can be movably disposed within the introducer valve as the puncture member and/or pusher device are used to delivery and deploy the distal anchor. In some embodiments, an end effector can be disposed at a distal end portion of the introducer valve.

While various embodiments of delivery devices have been described above with respect to procedures conducted by a human operator (e.g., a surgeon), in some embodiments, the delivery device can be configured to operate in conjunction with robotics used in, for example, robotic assisted surgery. Similarly stated, a robotic assisted procedure can be performed using the delivery devices described above.

While various embodiments have been described above with respect to a trans-apical approach and via a left atrium of a heart, in some embodiments, an anchor-tether apparatus can be delivered transfemorally (e.g., using a catheter). In some instances, for example, native mitral valve leaflets can be pierced from an atrial side to a ventricular side of the leaflets, and the free ends of the sutures can be secured together (e.g., an edge-to-edge repair). In other instances, as another example, after piercing a native mitral valve leaflet from the atrial side to the ventricular side of the leaflet, the free end of the suture can extend beyond the free edge of the leaflet towards the ventricle and be secured to the ventricular wall or through the apex of the heart and secured outside of the heart, as described with respect to previous embodiments. As a further example, in some instances, the anchor-tether apparatus can be delivered transfemorally, and the delivery device can pierce the native mitral valve leaflet from the ventricular side to the atrial side, and the sutures can be secured together or routed into the ventricle and secured to the ventricle wall.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

Depending on the embodiment, certain acts, events, or functions of any of the processes described herein can be performed in a different sequence, may be added, merged, or left out altogether. Thus, in certain embodiments, not all described acts or events are necessary for the practice of the processes. Moreover, in certain embodiments, acts or events may be performed concurrently.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. An apparatus, comprising:
   a handle;
   one or more actuators operably coupled to the handle;
   an elongate outer tube projecting from the handle;
   a pusher device defining a lumen and disposed at least partially within the elongate outer tube and the handle;
   a puncture member coupled to the one or more actuators and at least partially disposed within the lumen of the pusher device; and
   a tissue anchor disposed in a delivery configuration around a distal portion of the puncture member, the tissue anchor being associated with one or more suture tails that are coupled to the handle and extend through a lumen of the puncture member;

wherein the one or more actuators are configured to be actuated to cause (1) the puncture member to move distally to an extended position in which the puncture member projects from a distal opening of the elongate outer tube a preset distance, and (2) the pusher device to move distally such that the tissue anchor is pushed distally off of a distal end of the puncture member by a distal end of the pusher device while the puncture member is in the extended position.

2. The apparatus of claim 1, wherein, when the puncture member is moved distally to the extended position:

the tissue anchor is disposed at least partially within the elongate outer tube in the delivery configuration; and the distal end of the pusher device is disposed in the elongate outer tube.

3. The apparatus of claim 1, further comprising an end effector disposed at a distal end portion of the elongate outer tube, the end effector having a diameter greater than a diameter of the distal end portion of the elongate outer tube.

4. The apparatus of claim 1, wherein:

the tissue anchor is disposed in an elongated coiled configuration when in the delivery configuration;

the one or more actuators are configured such that the one or more suture tails are pulled proximally and the tissue anchor is moved from the elongated coiled configuration to a deployed configuration when the one or more actuators are actuated; and the tissue anchor is disposed in a coiled knot configuration when in the deployed configuration.

5. The apparatus of claim 1, wherein:

the one or more actuators comprise a plunger;

the plunger is movably coupled to the handle; and the puncture member is releasably coupled to the plunger.

6. The apparatus of claim 1, wherein the preset distance is between about 0.2 inches to about 0.3 inches.

7. The apparatus of claim 1, wherein:

the preset distance is a first preset distance;

the one or more actuators are configured to be actuated such that the pusher device is moved distally a second preset distance from the distal opening of the elongate outer tube;

the first preset distance being about 0.2 inches to about 0.3 inches; and the second preset distance being between about 0.6 inches to about 0.7 inches.

8. The apparatus of claim 1, further comprising a lock configured to:

prevent actuation of the one or more actuators when the lock is engaged; and allow actuation of the one or more actuators when the lock is disengaged.

9. The apparatus of claim 1, wherein the one or more actuators are configured to be actuated to cause the pusher device to further advance distally to cause the tissue anchor to transition to a deployed configuration.

10. The apparatus of claim 9, wherein:

in the delivery configuration, the tissue anchor has a first diameter; and in the deployed configuration, the tissue anchor has a second diameter that is greater than the first diameter.

11. The apparatus of claim 9, wherein:

in the delivery configuration, the tissue anchor has a first width; and in the deployed configuration, the tissue anchor has a second width that is greater than the first width.

12. An apparatus, comprising:

a handle;

one or more actuators operably coupled to the handle;

an elongate outer tube projecting from the handle;

a pusher device defining a lumen and disposed at least partially within the elongate outer tube and the handle;

a needle coupled to the one or more actuators and at least partially disposed within the lumen of the pusher device; and an anchor disposed on the needle in a delivery configuration;

wherein:

the anchor is associated with one or more suture strands that extend through a lumen defined by the needle;

the one or more actuators are configured to be actuated at a first time period to cause (1) the needle to advance distally a preset distance beyond a distal end of the elongate outer tube, and (2) the pusher device to advance distally to push the anchor distally beyond a distal end of the needle; and the one or more actuators are configured to be actuated at a second time period after the first time period to cause the anchor to transition from the delivery configuration to a deployed configuration.

13. The apparatus of claim 12, further comprising an end effector disposed at the distal end of the elongate outer tube, the end effector having a diameter greater than a diameter of the elongate outer tube.

14. The apparatus of claim 12, wherein:

in the delivery configuration, the anchor has a first diameter; and in the deployed configuration, the anchor has a second diameter that is greater than the first diameter.

15. The apparatus of claim 12, wherein:

in the delivery configuration, the anchor has a first width; and in the deployed configuration, the anchor has a second width that is greater than the first width.

16. The apparatus of claim 12, wherein the one or more suture strands are configured to function as an artificial chorda.

17. The apparatus of claim 12, wherein the preset distance is about 0.2 inches to about 0.3 inches.

18. The apparatus of claim 12, further comprising a lock configured to:

prevent actuation of the one or more actuators when the lock is engaged; and allow actuation of the one or more actuators when the lock is disengaged.

19. The apparatus of claim 12, wherein when the one or more actuators are actuated at the first time period, both the pusher device and the needle are moved distally through a lumen of the elongate outer tube.

20. The apparatus of claim 12, wherein:

the anchor is disposed in an elongated coiled configuration when in the delivery configuration;

when the one or more actuators are actuated at the second time period, the one or more suture strands are pulled proximally to cause the anchor to transition from the elongated coiled configuration to the deployed configuration; and the anchor is disposed in a coiled knot configuration when in the deployed configuration.

21. The apparatus of claim 20, wherein:
the one or more actuators comprise a needle hub and a pusher hub;
the needle hub and the pusher hub are movably coupled to the handle;
the pusher device is coupled to the pusher hub; and
the needle is coupled to the needle hub.

* * * * *